(12) United States Patent
Satterthwait et al.

(10) Patent No.: US 7,745,574 B2
(45) Date of Patent: Jun. 29, 2010

(54) COMPOUNDS THAT REGULATE APOPTOSIS

(75) Inventors: Arnold Satterthwait, San Diego, CA (US); Xiao-kun Zhang, San Diego, CA (US); Xiuwen Zhu, San Diego, CA (US); Siva Kolluri, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 710 days.

(21) Appl. No.: 11/433,783

(22) Filed: May 11, 2006

(65) Prior Publication Data

US 2007/0054863 A1     Mar. 8, 2007

Related U.S. Application Data

(60) Provisional application No. 60/689,206, filed on Jun. 9, 2005, provisional application No. 60/680,645, filed on May 12, 2005.

(51) Int. Cl.
*C07K 14/00* (2006.01)
*A61K 38/16* (2006.01)

(52) U.S. Cl. ......................................... 530/324; 514/12

(58) Field of Classification Search ...................... 514/2, 514/12, 15, 16; 530/350, 324, 328, 329; 435/69.1
See application file for complete search history.

(56) References Cited

U.S. PATENT DOCUMENTS

| 7,176,277 | B2 * | 2/2007 | Reed et al. | .................. 530/300 |
| 2004/0038902 | A1 * | 2/2004 | Pincus | ......................... 514/14 |
| 2004/0043463 | A1 * | 3/2004 | Rao | ............................. 435/184 |
| 2004/0220097 | A1 | 11/2004 | Reed et al. | |

OTHER PUBLICATIONS

Lundberg et al. A brief introduction to cell-penetraing peptides, 2003, Journal of Molecular Recognition, vol. 16, pp. 227-233.*
Letoha et al. Investigation of penetratin peptides. Part 2. In vitro uptake of penetratin and two of its derivatives, 2005, Journal of Peptide Science, vol. 11, pp. 805-811.*
Turner et al. Cell-penetrating peptide conjugates of peptide nucleic acids (PNA) as inhibitors of HIV-1 Tat-dependnet trans-activation in cells, Nov. 30, 2005, Nucleic Acids Research, vol. 33, No. 21, pp. 6837-6849.*
International Search Report from corresponding PCT application serial No. PCT/US2006/018315.
Korsmeyer, S.J. 1999 "BCL-2 gene family and the regulation of programmed cell death" *Cancer Research Supp.* 59: 1693s-1700s.
Li, H et al. 2000 "Cytochrome c release and apoptosis induced by mitochondrial targeting of nuclear orphan receptor TR3" *Science* 289:1159-1164.
Lin, B. et al. 2004 "Conversion of Bcl-2 from protector to killer by interaction with nuclear orphan receptor Nur77/TR3" *Cell* 116:527-540.
Wilson, A.J. et al. 2003 "TR3/Nur77 in colon cancer cell apoptosis" *Cancer Research* 63:5401-5407.

* cited by examiner

*Primary Examiner*—Andrew D Kosar
(74) *Attorney, Agent, or Firm*—Knobbe Martens Olson & Bear LLP

(57) ABSTRACT

Compounds that modulate the function of anti-apoptotic proteins such as Bcl-2 and related Bcl-2 family members are identified. These compounds have the ability to convert the activity of Bcl-2-family member proteins from anti-apoptotic to pro-apoptotic. Methods for inducing or preventing apoptosis are described, together with methods for identifying molecules that induce or prevent apoptosis through interaction with Bcl-2-family members. Methods for treatment of proliferative diseases and neurodegenerative diseases using the modulators of Bcl-2 and related family members are also disclosed.

13 Claims, 19 Drawing Sheets

GLVLHRLQCARG<u>FGDWIDSILA</u>F<u>SRSL</u>
<u>HSLL</u>VDVPA<u>FACL</u>SA<u>LVL</u>ITDRHGLQE
PRRVEELQNRIASCLKEHVAAVAGEP
QPASCLSRLLGKLPELRTLCTQGLQRI
<u>FYLKLEDLV</u>PPPPIIDKIFMDTLPF

Figure 15

SEQUENCE LISTING

```
<160> NUMBER OF SEQ ID NOS: 67

<210> SEQ ID NO 1
<211> LENGTH: 32
<212> TYPE: PRT
<213> ORGANISM: Artificial Sequence
<220> FEATURE:
<223> OTHER INFORMATION: synthetic peptide, NuBCP-20-r8
<220> FEATURE:
<221> NAME/KEY: MUTAGEN
<222> LOCATION: 24
<223> OTHER INFORMATION: Aminohexanoic acid
<220> FEATURE:
<221> NAME/KEY: MUTAGEN
```

```
<222> LOCATION: (25)...(32)
<223> OTHER INFORMATION: D-amino acid

<400> SEQUENCE: 1

Gly Asp Trp Ile Asp Ser Ile Leu Ala Phe Ser Arg Ser Leu His Ser
 1               5                  10                  15

Leu Leu Val Asp Lys Lys Cys Xaa Arg Arg Arg Arg Arg Arg
            20                  25                  30

<210> SEQ ID NO 2
<211> LENGTH: 25
<212> TYPE: PRT
<213> ORGANISM: Artificial Sequence
<220> FEATURE:
<223> OTHER INFORMATION: synthetic peptide NuBCP-15
<220> FEATURE:
<221> NAME/KEY: MUTAGEN
<222> LOCATION: 17
<223> OTHER INFORMATION: Aminohexanoic acid
<220> FEATURE:
<221> NAME/KEY: MUTAGEN
<222> LOCATION: (18)...(25)
<223> OTHER INFORMATION: D-amino acid

<400> SEQUENCE: 2

Ser Ile Leu Ala Phe Ser Arg Ser Leu His Ser Leu Leu Val Asp Gly
 1               5                  10                  15

Xaa Arg Arg Arg Arg Arg Arg Arg Arg
            20                  25

<210> SEQ ID NO 3
<211> LENGTH: 24
<212> TYPE: PRT
<213> ORGANISM: Artificial Sequence
<220> FEATURE:
<223> OTHER INFORMATION: synthetic peptide, NuBCP-14
<220> FEATURE:
<221> NAME/KEY: MUTAGEN
<222> LOCATION: 16
<223> OTHER INFORMATION: Aminohexanoic acid
<220> FEATURE:
<221> NAME/KEY: MUTAGEN
<222> LOCATION: (17)...(24)
<223> OTHER INFORMATION: D-amino acid

<400> SEQUENCE: 3

Ile Leu Ala Phe Ser Arg Ser Leu His Ser Leu Leu Val Asp Gly Xaa
 1               5                  10                  15

Arg Arg Arg Arg Arg Arg Arg Arg
            20

<210> SEQ ID NO 4
<211> LENGTH: 23
<212> TYPE: PRT
<213> ORGANISM: Artificial Sequence
<220> FEATURE:
<223> OTHER INFORMATION: synthetic peptide, NuBCP-13
<220> FEATURE:
<221> NAME/KEY: MUTAGEN
<222> LOCATION: 15
<223> OTHER INFORMATION: Aminohexanoic acid
<220> FEATURE:
<221> NAME/KEY: MUTAGEN
<222> LOCATION: (16)...(23)
<223> OTHER INFORMATION: D-amino acid

<400> SEQUENCE: 4

Leu Ala Phe Ser Arg Ser Leu His Ser Leu Leu Val Asp Gly Xaa Arg
 1               5                  10                  15
```

```
Arg Arg Arg Arg Arg Arg Arg
            20

<210> SEQ ID NO 5
<211> LENGTH: 22
<212> TYPE: PRT
<213> ORGANISM: Artificial Sequence
<220> FEATURE:
<223> OTHER INFORMATION: synthetic peptide, NuBCP-12
<220> FEATURE:
<221> NAME/KEY: MUTAGEN
<222> LOCATION: 14
<223> OTHER INFORMATION: Aminohexanoic acid
<220> FEATURE:
<221> NAME/KEY: MUTAGEN
<222> LOCATION: (15)...(22)
<223> OTHER INFORMATION: D-amino acid

<400> SEQUENCE: 5

Ala Phe Ser Arg Ser Leu His Ser Leu Leu Val Asp Gly Xaa Arg Arg
 1               5                  10                  15

Arg Arg Arg Arg Arg Arg
            20

<210> SEQ ID NO 6
<211> LENGTH: 21
<212> TYPE: PRT
<213> ORGANISM: Artificial Sequence
<220> FEATURE:
<223> OTHER INFORMATION: synthetic peptide, NuBCP-11
<220> FEATURE:
<221> NAME/KEY: MUTAGEN
<222> LOCATION: 13
<223> OTHER INFORMATION: Aminohexanoic acid
<220> FEATURE:
<221> NAME/KEY: MUTAGEN
<222> LOCATION: (14)...(21)
<223> OTHER INFORMATION: D-amino acid

<400> SEQUENCE: 6

Phe Ser Arg Ser Leu His Ser Leu Leu Val Asp Gly Xaa Arg Arg Arg
 1               5                  10                  15

Arg Arg Arg Arg Arg
            20

<210> SEQ ID NO 7
<211> LENGTH: 20
<212> TYPE: PRT
<213> ORGANISM: Artificial Sequence
<220> FEATURE:
<223> OTHER INFORMATION: synthetic peptide, NuBCP-10
<220> FEATURE:
<221> NAME/KEY: MUTAGEN
<222> LOCATION: 12
<223> OTHER INFORMATION: Aminohexanoic acid
<220> FEATURE:
<221> NAME/KEY: MUTAGEN
<222> LOCATION: (13)...(20)
<223> OTHER INFORMATION: D-amino acid

<400> SEQUENCE: 7

Ser Arg Ser Leu His Ser Leu Leu Val Asp Gly Xaa Arg Arg Arg Arg
 1               5                  10                  15

Arg Arg Arg Arg
            20

<210> SEQ ID NO 8
<211> LENGTH: 20
```

```
<212> TYPE: PRT
<213> ORGANISM: Artificial Sequence
<220> FEATURE:
<223> OTHER INFORMATION: synthetic peptide, NuBCP-N10
<220> FEATURE:
<221> NAME/KEY: MUTAGEN
<222> LOCATION: 12
<223> OTHER INFORMATION: Aminohexanoic acid
<220> FEATURE:
<221> NAME/KEY: MUTAGEN
<222> LOCATION: (13)...(20)
<223> OTHER INFORMATION: D-amino acid

<400> SEQUENCE: 8

Phe Ser Arg Ser Leu His Ser Leu Leu Val Gly Xaa Arg Arg Arg Arg
 1               5                  10                  15

Arg Arg Arg Arg
            20

<210> SEQ ID NO 9
<211> LENGTH: 19
<212> TYPE: PRT
<213> ORGANISM: Artificial Sequence
<220> FEATURE:
<223> OTHER INFORMATION: synthetic peptide, NuBCP-9-r8
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 9

Phe Ser Arg Ser Leu His Ser Leu Leu Gly Xaa Arg Arg Arg Arg Arg
 1               5                  10                  15

Arg Arg Arg

<210> SEQ ID NO 10
<211> LENGTH: 18
<212> TYPE: PRT
<213> ORGANISM: Artificial Sequence
<220> FEATURE:
<223> OTHER INFORMATION: synthetic peptide, NuBCP-8
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(19)
<223> OTHER INFORMATION: D-amino acid

<400> SEQUENCE: 10

Phe Ser Arg Ser Leu His Ser Leu Gly Xaa Arg Arg Arg Arg Arg Arg
 1               5                  10                  15

Arg Arg

<210> SEQ ID NO 11
<211> LENGTH: 17
<212> TYPE: PRT
<213> ORGANISM: Artificial Sequence
<220> FEATURE:
<223> OTHER INFORMATION: synthetic peptide, NuBCP-7
<220> FEATURE:
<221> NAME/KEY: MUTAGEN
<222> LOCATION: 9
<223> OTHER INFORMATION: Aminohexanoic acid
<220> FEATURE:
```

```
<221> NAME/KEY: MUTAGEN
<222> LOCATION: (10)...(17)
<223> OTHER INFORMATION: D-amino acid

<400> SEQUENCE: 11

Phe Ser Arg Ser Leu His Ser Gly Xaa Arg Arg Arg Arg Arg Arg
 1               5                  10                  15

Arg

<210> SEQ ID NO 12
<211> LENGTH: 19
<212> TYPE: PRT
<213> ORGANISM: Artificial Sequence
<220> FEATURE:
<223> OTHER INFORMATION: synthetic peptide, NuBCP-9/AA
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (13)...(20)
<223> OTHER INFORMATION: D-amino acid

<400> SEQUENCE: 12

Ala Ser Arg Ser Leu His Ser Leu Ala Gly Xaa Arg Arg Arg Arg
 1               5                  10                  15

Arg Arg Arg

<210> SEQ ID NO 13
<211> LENGTH: 19
<212> TYPE: PRT
<213> ORGANISM: Artificial Sequence
<220> FEATURE:
<223> OTHER INFORMATION: synthetic peptide, D-NuBCP-9-r8
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (1)...(9)
<223> OTHER INFORMATION: D-amino acid
<220> FEATURE:
<221> NAME/KEY: MUTAGEN
<222> LOCATION: (12)...(19)
<223> OTHER INFORMATION: D-amino acid

<400> SEQUENCE: 13

Phe Ser Arg Ser Leu His Ser Leu Leu Gly Xaa Arg Arg Arg Arg
 1               5                  10                  15

Arg Arg Arg

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide, Nur77/1 (inverso)
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 14
```

Leu Leu Ser His Leu Ser Arg Ser Phe Gly Xaa Arg Arg Arg Arg
1               5                   10                  15

Arg Arg Arg

<210> SEQ ID NO 15
<211> LENGTH: 19
<212> TYPE: PRT
<213> ORGANISM: Artificial Sequence
<220> FEATURE:
<223> OTHER INFORMATION: Synthetic peptide, Nur77/1 (retroinverso)
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (1)...(9)
<223> OTHER INFORMATION: D-amino acid
<220> FEATURE:
<221> NAME/KEY: MUTAGEN
<222> LOCATION: (12)...(19)
<223> OTHER INFORMATION: D-amino acid

<400> SEQUENCE: 15

Leu Leu Ser His Leu Ser Arg Ser Phe Gly Xaa Arg Arg Arg Arg
1               5                   10                  15

Arg Arg Arg

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide, Nur77/2
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 16

Phe Gly Asp Trp Ile Asp Ser Ile Leu Gly Xaa Arg Arg Arg Arg
1               5                   10                  15

Arg Arg Arg

<210> SEQ ID NO 17
<211> LENGTH: 19
<212> TYPE: PRT
<213> ORGANISM: Artificial Sequence
<220> FEATURE:
<223> OTHER INFORMATION: Synthetic peptide, Nur77/3
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 17

Phe Ala Ala Leu Ser Ala Leu Val Leu Gly Xaa Arg Arg Arg Arg
1               5                   10                  15

Arg Arg Arg

```
<210> SEQ ID NO 18
<211> LENGTH: 19
<212> TYPE: PRT
<213> ORGANISM: Artificial Sequence
<220> FEATURE:
<223> OTHER INFORMATION: Synthetic peptide, Nur77/4
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 18

Phe Tyr Leu Lys Leu Glu Asp Leu Val Gly Xaa Arg Arg Arg Arg
1               5                   10                  15

Arg Arg Arg

<210> SEQ ID NO 19
<211> LENGTH: 24
<212> TYPE: PRT
<213> ORGANISM: Artificial Sequence
<220> FEATURE:
<223> OTHER INFORMATION: Synthetic peptide, Nor1
<220> FEATURE:
<221> NAME/KEY: MUTAGEN
<222> LOCATION: (17)...(24)
<223> OTHER INFORMATION: D-amino acid

<400> SEQUENCE: 19

Ser Ile Lys Asp Phe Ser Leu Asn Leu Gln Ser Leu Asn Leu Asp Gly
1               5                   10                  15

Arg Arg Arg Arg Arg Arg Arg Arg
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic peptide, NOT
<220> FEATURE:
<221> NAME/KEY: MUTAGEN
<222> LOCATION: (17)...(24)
<223> OTHER INFORMATION: D-amino acid

<400> SEQUENCE: 20

Ser Ile Val Glu Phe Ser Ser Asn Leu Gln Asn Met Asn Ile Asp Gly
1               5                   10                  15

Arg Arg Arg Arg Arg Arg Arg Arg
            20

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide, Nur77/1 (embedded)
<220> FEATURE:
<221> NAME/KEY: MUTAGEN
<222> LOCATION: 1, 2, 3, 5, 6, 7, 9, 10
<223> OTHER INFORMATION: D-amino acid

<400> SEQUENCE: 21

Arg Arg Arg Phe Arg Arg Arg Leu Arg Arg Leu Leu
1               5                   10
```

```
<210> SEQ ID NO 22
<211> LENGTH: 12
<212> TYPE: PRT
<213> ORGANISM: Artificial Sequence
<220> FEATURE:
<223> OTHER INFORMATION: Synthetic peptide, Nur77/1 (D/embedded)
<220> FEATURE:
<221> NAME/KEY: MUTAGEN
<222> LOCATION: (1)...(12)
<223> OTHER INFORMATION: D-amino acid

<400> SEQUENCE: 22

Arg Arg Arg Phe Arg Arg Arg Leu Arg Arg Leu Leu
 1               5                  10

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 1, 3, 5, 7, 9
<223> OTHER INFORMATION: D-amino acid
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 23

Phe Ser Arg Ser Leu His Ser Leu Leu Gly Xaa Arg Arg Arg Arg
 1               5                  10                  15

Arg Arg Arg

<210> SEQ ID NO 24
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 1, 4, 5, 8, 9
<223> OTHER INFORMATION: D-amino acid
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 24

Phe Ser Arg Ser Leu His Ser Leu Leu Gly Xaa Arg Arg Arg Arg
 1               5                  10                  15

Arg Arg Arg

<210> SEQ ID NO 25
<211> LENGTH: 19
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 25

Phe Ala Arg Ser Leu His Ser Leu Leu Gly Xaa Arg Arg Arg Arg
1               5                   10                  15

Arg Arg Arg

<210> SEQ ID NO 26
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 26

Phe Ser Ala Ser Leu His Ser Leu Leu Gly Xaa Arg Arg Arg Arg
1               5                   10                  15

Arg Arg Arg

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 27

Phe Ser Arg Ala Leu His Ser Leu Leu Gly Xaa Arg Arg Arg Arg
1               5                   10                  15

Arg Arg Arg

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 28
```

```
Phe Ser Arg Ser Leu Ala Ser Leu Leu Gly Xaa Arg Arg Arg Arg
1               5                   10                  15

Arg Arg Arg

<210> SEQ ID NO 29
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 29

Phe Ser Arg Ser Leu His Ala Leu Leu Gly Xaa Arg Arg Arg Arg
1               5                   10                  15

Arg Arg Arg

<210> SEQ ID NO 30
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(18)
<223> OTHER INFORMATION: D-amino acid

<400> SEQUENCE: 30

Phe Arg Ser Leu His Ser Leu Leu Gly Xaa Arg Arg Arg Arg Arg
1               5                   10                  15

Arg Arg

<210> SEQ ID NO 31
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(18)
<223> OTHER INFORMATION: D-amino acid

<400> SEQUENCE: 31

Phe Ser Ser Leu His Ser Leu Leu Gly Xaa Arg Arg Arg Arg Arg
1               5                   10                  15

Arg Arg

<210> SEQ ID NO 32
<211> LENGTH: 18
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(18)
<223> OTHER INFORMATION: D-amino acid

<400> SEQUENCE: 32

Phe Ser Arg Leu His Ser Leu Leu Gly Xaa Arg Arg Arg Arg Arg
 1               5                  10                  15

Arg Arg

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(18)
<223> OTHER INFORMATION: D-amino acid

<400> SEQUENCE: 33

Phe Ser Arg Ser Leu Ser Leu Leu Gly Xaa Arg Arg Arg Arg Arg
 1               5                  10                  15

Arg Arg

<210> SEQ ID NO 34
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(18)
<223> OTHER INFORMATION: D-amino acid

<400> SEQUENCE: 34

Phe Ser Arg Ser Leu His Leu Leu Gly Xaa Arg Arg Arg Arg Arg
 1               5                  10                  15

Arg Arg

<210> SEQ ID NO 35
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 9
<223> OTHER INFORMATION: Aminohexanoic acid
<220> FEATURE:
<221> NAME/KEY: MUTAGEN
<222> LOCATION: (10)...(17)
<223> OTHER INFORMATION: D-amino acid
```

<400> SEQUENCE: 35

Phe Ser Leu His Ser Leu Leu Gly Xaa Arg Arg Arg Arg Arg Arg
1               5                   10                  15

Arg

<210> SEQ ID NO 36
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (1)...(8)
<223> OTHER INFORMATION: D-amino acid
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(17)
<223> OTHER INFORMATION: D-amino acid

<400> SEQUENCE: 36

Phe Arg Ser Leu His Ser Leu Leu Gly Xaa Arg Arg Arg Arg Arg
1               5                   10                  15

Arg Arg

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 2, 10
<223> OTHER INFORMATION: Aminohexanoic acid
<220> FEATURE:
<221> NAME/KEY: MUTAGEN
<222> LOCATION: (11)...(17)
<223> OTHER INFORMATION: D-amino acid

<400> SEQUENCE: 37

Phe Xaa Ser Leu His Ser Leu Leu Gly Xaa Arg Arg Arg Arg Arg
1               5                   10                  15

Arg Arg

<210> SEQ ID NO 38
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid

<400> SEQUENCE: 38

Phe Ser Arg Ser Leu His Ser Leu Leu Gly Xaa Cys Gly Asn Lys Arg
1               5                   10                  15

Thr Ala Cys

<210> SEQ ID NO 39

```
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid

<400> SEQUENCE: 39

Phe Ser Arg Ser Leu His Ser Leu Leu Gly Xaa Ala Lys Val Lys Asp
 1               5                  10                  15

Glu Pro Gln Arg Arg Ser Ala Arg Leu Ser Ala Lys Pro Ala Pro Pro
            20                  25                  30

Lys Pro Glu Pro Lys Pro Lys Lys Ala Pro Ala Lys Lys
        35                  40                  45

<210> SEQ ID NO 40
<211> LENGTH: 14
<212> TYPE: PRT
<213> ORGANISM: Artificial Sequence
<220> FEATURE:
<223> OTHER INFORMATION: Synthetic peptide, Nur77/short
<220> FEATURE:
<221> NAME/KEY: MUTAGEN
<222> LOCATION: 6
<223> OTHER INFORMATION: Aminohexanoic acid
<220> FEATURE:
<221> NAME/KEY: MUTAGEN
<222> LOCATION: (7)...(14)
<223> OTHER INFORMATION: D-amino acid

<400> SEQUENCE: 40

Phe Leu Leu Leu Gly Xaa Arg Arg Arg Arg Arg Arg Arg Arg
 1               5                  10

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide, Nur77/short D
<220> FEATURE:
<221> NAME/KEY: MUTAGEN
<222> LOCATION: (1)...(4)
<223> OTHER INFORMATION: D-amino acid
<220> FEATURE:
<221> NAME/KEY: MUTAGEN
<222> LOCATION: 6
<223> OTHER INFORMATION: Aminohexanoic acid
<220> FEATURE:
<221> NAME/KEY: MUTAGEN
<222> LOCATION: (7)...(14)
<223> OTHER INFORMATION: D-amino acid

<400> SEQUENCE: 41

Phe Leu Leu Leu Gly Xaa Arg Arg Arg Arg Arg Arg Arg Arg
 1               5                  10

<210> SEQ ID NO 42
<211> LENGTH: 27
<212> TYPE: PRT
<213> ORGANISM: Artificial Sequence
<220> FEATURE:
<223> OTHER INFORMATION: Synthetic peptide, Nur77/1 Ant

<400> SEQUENCE: 42

Phe Ser Arg Ser Leu His Ser Leu Leu Cys Cys Arg Gln Ile Lys Ile
 1               5                  10                  15
```

```
Trp Phe Gln Asn Arg Arg Met Lys Trp Lys Lys
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic peptide, Nur77/1 Ant (D)
<220> FEATURE:
<221> NAME/KEY: MUTAGEN
<222> LOCATION: (1)...(27)
<223> OTHER INFORMATION: D-amino acid

<400> SEQUENCE: 43

Phe Ser Arg Ser Leu His Ser Leu Leu Cys Cys Arg Gln Ile Lys Ile
1               5                   10                  15

Trp Phe Gln Asn Arg Arg Met Lys Trp Lys Lys
            20                  25

<210> SEQ ID NO 44
<211> LENGTH: 18
<212> TYPE: PRT
<213> ORGANISM: Artificial Sequence
<220> FEATURE:
<223> OTHER INFORMATION: Synthetic p53
<220> FEATURE:
<221> NAME/KEY: MUTAGEN
<222> LOCATION: 10
<223> OTHER INFORMATION: Aminohexanoic acid
<220> FEATURE:
<221> NAME/KEY: MUTAGEN
<222> LOCATION: (11)...(17)
<223> OTHER INFORMATION: D-amino acid

<400> SEQUENCE: 44

Phe Ser Asp Leu Trp Lys Leu Leu Gly Xaa Arg Arg Arg Arg Arg
1               5                   10                  15

Arg Arg

<210> SEQ ID NO 45
<211> LENGTH: 29
<212> TYPE: PRT
<213> ORGANISM: Artificial Sequence
<220> FEATURE:
<223> OTHER INFORMATION: Synthetic peptide, Nur77 (embedded2)
<220> FEATURE:
<221> NAME/KEY: MUTAGEN
<222> LOCATION: (22)...(29)
<223> OTHER INFORMATION: D-amino acid

<400> SEQUENCE: 45

Asn Phe Gln His Ala Leu Gln Glu Val Leu Gln Ala Leu Lys Gln Val
1               5                   10                  15

Gln Ala Arg Cys Cys Arg Arg Arg Arg Arg Arg Arg
            20                  25

<210> SEQ ID NO 46
<211> LENGTH: 19
<212> TYPE: PRT
<213> ORGANISM: Artificial Sequence
<220> FEATURE:
<223> OTHER INFORMATION: Synthetic peptide, Nur77/1 (D/L)
<220> FEATURE:
<221> NAME/KEY: MUTAGEN
<222> LOCATION: 1, 3, 5, 7, 9
<223> OTHER INFORMATION: D-amino acid
<220> FEATURE:
```

```
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 46

Phe Ser Arg Ser Leu His Ser Leu Leu Gly Xaa Arg Arg Arg Arg
 1               5                  10                  15

Arg Arg Arg

<210> SEQ ID NO 47
<211> LENGTH: 19
<212> TYPE: PRT
<213> ORGANISM: Artificial Sequence
<220> FEATURE:
<223> OTHER INFORMATION: Synthetic peptide, Nur77/1 (DD/LL)
<220> FEATURE:
<221> NAME/KEY: MUTAGEN
<222> LOCATION: 1, 4, 5, 8, 9
<223> OTHER INFORMATION: D-amino acid
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 47

Phe Ser Arg Ser Leu His Ser Leu Leu Gly Xaa Arg Arg Arg Arg
 1               5                  10                  15

Arg Arg Arg

<210> SEQ ID NO 48
<211> LENGTH: 27
<212> TYPE: PRT
<213> ORGANISM: Artificial Sequence
<220> FEATURE:
<223> OTHER INFORMATION: Synthetic peptide, NuBCP-9- Penetratin

<400> SEQUENCE: 48

Phe Ser Arg Ser Leu His Ser Leu Leu Cys Cys Arg Gln Ile Lys Ile
 1               5                  10                  15

Trp Phe Gln Asn Arg Arg Met Lys Trp Lys Lys
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic peptide, Nu77/1 (D) Penetratin (D)
<220> FEATURE:
<221> NAME/KEY: MUTAGEN
<222> LOCATION: (1)...(7)
<223> OTHER INFORMATION: D-amino acid

<400> SEQUENCE: 49

Phe Ser Arg Ser Leu His Ser Leu Leu Cys Cys Arg Gln Val Lys Ile
 1               5                  10                  15

Trp Phe Gln Asn Arg Arg Met Lys Trp Lys Lys
            20                  25
```

<210> SEQ ID NO 50
<211> LENGTH: 32
<212> TYPE: PRT
<213> ORGANISM: Artificial Sequence
<220> FEATURE:
<223> OTHER INFORMATION: Synthetic peptide, Nu77/1 Transportan10

<400> SEQUENCE: 50

Phe Ser Arg Ser Leu His Ser Leu Leu Cys Cys Ala Gly Tyr Leu Leu
1               5                   10                  15

Gly Lys Ile Asn Leu Lys Ala Leu Ala Ala Leu Ala Lys Lys Ile Leu
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Synthetic peptide, Nu77/1 (D)Transportan10 (D)
<220> FEATURE:
<221> NAME/KEY: MUTAGEN
<222> LOCATION: (1)...(32)
<223> OTHER INFORMATION: D-amino acid

<400> SEQUENCE: 51

Phe Ser Arg Ser Leu His Ser Leu Leu Cys Cys Ala Gly Tyr Leu Leu
1               5                   10                  15

Gly Lys Val Asn Leu Lys Ala Leu Ala Ala Leu Ala Lys Lys Val Leu
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic peptide, Nu77/1 (L/D)Transportan10
      (L/D)
<220> FEATURE:
<221> NAME/KEY: MUTAGEN
<222> LOCATION: 2, 4, 6, 8, 10, 12, 14, 16, 18, 20, 22, 24, 26, 28, 30,
      32
<223> OTHER INFORMATION: D-amino acid

<400> SEQUENCE: 52

Phe Ser Arg Ser Leu His Ser Leu Leu Cys Cys Ala Gly Tyr Leu Leu
1               5                   10                  15

Gly Lys Ile Asn Leu Lys Ala Leu Ala Ala Leu Ala Lys Lys Ile Leu
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic peptide, Nu77/1 (LLDD)Transportan10
      (LLDD)
<220> FEATURE:
<221> NAME/KEY: MUTAGEN
<222> LOCATION: 3, 4, 7, 8, 11, 12, 15, 16, 19, 20, 23, 24, 27, 28, 31,
      32
<223> OTHER INFORMATION: D-amino acid

<400> SEQUENCE: 53

Phe Ser Arg Ser Leu His Ser Leu Leu Cys Cys Ala Gly Tyr Leu Leu
1               5                   10                  15

Gly Lys Val Asn Leu Lys Ala Leu Ala Ala Leu Ala Lys Lys Val Leu
            20                  25                  30

-continued

<210> SEQ ID NO 54
<211> LENGTH: 37
<212> TYPE: PRT
<213> ORGANISM: Artificial Sequence
<220> FEATURE:
<223> OTHER INFORMATION: Synthetic peptide, NuBCP-9-Transportan

<400> SEQUENCE: 54

Phe Ser Arg Ser Leu His Ser Leu Leu Cys Cys Gly Trp Thr Leu Asn
 1               5                  10                  15

Ser Ala Gly Tyr Leu Leu Gly Lys Ile Asn Lys Ala Leu Ala Ala Leu
            20                  25                  30

Ala Lys Lys Ile Leu
        35

<210> SEQ ID NO 55
<211> LENGTH: 598
<212> TYPE: PRT
<213> ORGANISM: Homo sapiens

<400> SEQUENCE: 55

Met Pro Cys Ile Gln Ala Gln Tyr Gly Thr Pro Ala Pro Ser Pro Gly
 1               5                  10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Ala Pro Ala Ala Pro Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
            100                 105                 110

Pro Gly Pro Leu Ser Gly Pro Val Asp Glu Ala Leu Ser Ser Ser Gly
        115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Gln Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Pro Ser Glu Gly Arg Cys Ala Val Cys Gly Asp
            260                 265                 270

Asn Ala Ser Cys Gln His Tyr Gly Val Arg Thr Cys Glu Gly Cys Lys

-continued

```
            275                 280                 285
Gly Phe Phe Lys Arg Thr Val Gln Lys Asn Ala Lys Tyr Ile Cys Leu
    290                 295                 300
Ala Asn Lys Asp Cys Pro Val Asp Lys Arg Arg Arg Asn Arg Cys Gln
305                 310                 315                 320
Phe Cys Arg Phe Gln Lys Cys Leu Ala Val Gly Met Val Lys Glu Val
                325                 330                 335
Val Arg Thr Asp Ser Leu Lys Gly Arg Arg Gly Arg Leu Pro Ser Lys
                340                 345                 350
Pro Lys Gln Pro Pro Asp Ala Ser Pro Ala Asn Leu Leu Thr Ser Leu
            355                 360                 365
Val Leu Ala His Leu Asp Ser Gly Pro Ser Thr Ala Lys Leu Asp Tyr
    370                 375                 380
Ser Lys Phe Gln Glu Leu Val Leu Pro His Phe Gly Lys Glu Asp Ala
385                 390                 395                 400
Gly Asp Val Gln Gln Phe Tyr Asp Leu Leu Ser Gly Ser Leu Glu Val
                405                 410                 415
Ile Arg Lys Trp Ala Glu Lys Ile Pro Gly Phe Ala Glu Leu Ser Pro
                420                 425                 430
Ala Asp Gln Asp Leu Leu Leu Glu Ser Ala Phe Leu Glu Leu Phe Ile
            435                 440                 445
Leu Arg Leu Ala Tyr Arg Ser Lys Pro Gly Glu Gly Lys Leu Ile Phe
    450                 455                 460
Cys Ser Gly Leu Val Leu His Arg Leu Gln Cys Ala Arg Gly Phe Gly
465                 470                 475                 480
Asp Trp Ile Asp Ser Ile Leu Ala Phe Ser Arg Ser Leu His Ser Leu
                485                 490                 495
Leu Val Asp Val Pro Ala Phe Ala Cys Leu Ser Ala Leu Val Leu Ile
                500                 505                 510
Thr Asp Arg His Gly Leu Gln Glu Pro Arg Arg Val Glu Glu Leu Gln
            515                 520                 525
Asn Arg Ile Ala Ser Cys Leu Lys Glu His Val Ala Ala Val Ala Gly
    530                 535                 540
Glu Pro Gln Pro Ala Ser Cys Leu Ser Arg Leu Leu Gly Lys Leu Pro
545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Pro Ile Ile Asp Lys Ile Phe
                580                 585                 590
Met Asp Thr Leu Pro Phe
        595

<210> SEQ ID NO 56
<211> LENGTH: 17
<212> TYPE: PRT
<213> ORGANISM: Artificial Sequence
<220> FEATURE:
<223> OTHER INFORMATION: Synthetic peptide, Smac-peptide-r8
<220> FEATURE:
<221> NAME/KEY: MUTAGEN
<222> LOCATION: 9
<223> OTHER INFORMATION: Aminohexanoic acid
<220> FEATURE:
<221> NAME/KEY: MUTAGEN
<222> LOCATION: (10)...(17)
<223> OTHER INFORMATION: D-amino acid

<400> SEQUENCE: 56
```

Ala Val Pro Ile Ala Gln Lys Cys Xaa Arg Arg Arg Arg Arg Arg
1               5                   10                  15

Arg

<210> SEQ ID NO 57
<211> LENGTH: 30
<212> TYPE: PRT
<213> ORGANISM: Artificial Sequence
<220> FEATURE:
<223> OTHER INFORMATION: Synthetic peptide, t-Bid BH3 peptide-r8
<220> FEATURE:
<221> NAME/KEY: MUTAGEN
<222> LOCATION: 22
<223> OTHER INFORMATION: Aminohexanoic acid
<220> FEATURE:
<221> NAME/KEY: MUTAGEN
<222> LOCATION: (23)...(30)
<223> OTHER INFORMATION: D-amino acid

<400> SEQUENCE: 57

Glu Asp Ile Ile Arg Asn Ile Ala Arg His Leu Ala Gln Val Gly Asp
1               5                   10                  15

Ser Met Asp Arg Cys Xaa Arg Arg Arg Arg Arg Arg Arg
            20                  25                  30

<210> SEQ ID NO 58
<211> LENGTH: 43
<212> TYPE: PRT
<213> ORGANISM: Artificial Sequence
<220> FEATURE:
<223> OTHER INFORMATION: Synthetic peptide, Bad BH3 peptide-CC-Ant

<400> SEQUENCE: 58

Asn Leu Trp Ala Ala Gln Arg Tyr Gly Arg Glu Leu Arg Arg Met Ala
1               5                   10                  15

Asp Glu Phe Val Asp Ala Phe Lys Lys Cys Cys Arg Gln Ile Lys Ile
            20                  25                  30

Trp Phe Gln Asn Arg Arg Met Lys Trp Lys Lys
        35                  40

<210> SEQ ID NO 59
<211> LENGTH: 43
<212> TYPE: PRT
<213> ORGANISM: Artificial Sequence
<220> FEATURE:
<223> OTHER INFORMATION: Synthetic peptide, D-Bad BH3 peptide-CC-Ant
<220> FEATURE:
<221> NAME/KEY: MUTAGEN
<222> LOCATION: (1)...(25)
<223> OTHER INFORMATION: D-amino acid

<400> SEQUENCE: 59

Asn Leu Trp Ala Ala Gln Arg Tyr Gly Arg Glu Leu Arg Arg Met Ala
1               5                   10                  15

Asp Glu Phe Val Asp Ala Phe Lys Lys Cys Cys Arg Gln Ile Lys Ile
            20                  25                  30

Trp Phe Gln Asn Arg Arg Met Lys Trp Lys Lys
        35                  40

<210> SEQ ID NO 60
<211> LENGTH: 132
<212> TYPE: PRT
<213> ORGANISM: Homo sapiens

<400> SEQUENCE: 60

-continued

```
Gly Leu Val Leu His Arg Leu Gln Cys Ala Arg Gly Phe Gly Asp Trp
1               5                   10                  15

Ile Asp Ser Ile Leu Ala Phe Ser Arg Ser Leu His Ser Leu Leu Val
            20                  25                  30

Asp Val Pro Ala Phe Ala Cys Leu Ser Ala Leu Val Leu Ile Thr Asp
        35                  40                  45

Arg His Gly Leu Gln Glu Pro Arg Arg Val Glu Leu Gln Asn Arg
    50                  55                  60

Ile Ala Ser Cys Leu Lys Glu His Val Ala Ala Val Ala Gly Glu Pro
65              70                  75                  80

Gln Pro Ala Ser Cys Leu Ser Arg Leu Leu Gly Lys Leu Pro Glu Leu
                85                  90                  95

Arg Thr Leu Cys Thr Gln Gly Leu Gln Arg Ile Phe Tyr Leu Lys Leu
            100                 105                 110

Glu Asp Leu Val Pro Pro Pro Ile Ile Asp Lys Ile Phe Met Asp
        115                 120                 125

Thr Leu Pro Phe
    130
```

<210> SEQ ID NO 61
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 61

```
Ala Ser Arg Ser Leu His Ser Leu Leu Gly Xaa Arg Arg Arg Arg
1               5                   10                  15

Arg Arg Arg
```

<210> SEQ ID NO 62
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 62

```
Phe Ser Arg Ser Ala His Ser Leu Leu Gly Xaa Arg Arg Arg Arg
1               5                   10                  15

Arg Arg Arg
```

<210> SEQ ID NO 63
<211> LENGTH: 19
<212> TYPE: PRT
<213> ORGANISM: Artificial Sequence

```
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 63

Phe Ser Arg Ser Leu His Ser Ala Leu Gly Xaa Arg Arg Arg Arg
 1               5                  10                  15

Arg Arg Arg

<210> SEQ ID NO 64
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: 11
<223> OTHER INFORMATION: Aminohexanoic acid
<220> FEATURE:
<221> NAME/KEY: MUTAGEN
<222> LOCATION: (12)...(19)
<223> OTHER INFORMATION: D-amino acid

<400> SEQUENCE: 64

Phe Ser Arg Ser Leu His Ser Leu Ala Gly Xaa Arg Arg Arg Arg
 1               5                  10                  15

Arg Arg Arg

<210> SEQ ID NO 65
<211> LENGTH: 16
<212> TYPE: PRT
<213> ORGANISM: Artificial Sequence
<220> FEATURE:
<223> OTHER INFORMATION: Synthetic peptide, penetratin

<400> SEQUENCE: 65

Arg Gln Ile Lys Ile Trp Phe Gln Asn Arg Arg Met Lys Trp Lys Lys
 1               5                  10                  15

<210> SEQ ID NO 66
<211> LENGTH: 21
<212> TYPE: PRT
<213> ORGANISM: Artificial Sequence
<220> FEATURE:
<223> OTHER INFORMATION: Synthetic peptide, transportan10

<400> SEQUENCE: 66

Ala Gly Tyr Leu Leu Gly Lys Ile Asn Leu Lys Ala Leu Ala Ala Leu
 1               5                  10                  15

Ala Lys Lys Ile Leu
                20

<210> SEQ ID NO 67
<211> LENGTH: 18
<212> TYPE: DNA
<213> ORGANISM: Artificial Sequence
```

```
-continued

<220> FEATURE:
<223> OTHER INFORMATION: Synthetic oligonucleotide

<400> SEQUENCE: 67
caguccagcc augcuccu                                                    18
```

COMPOUNDS THAT REGULATE APOPTOSIS

RELATED APPLICATIONS

This application claims the benefit of priority of U.S. Provisional Application No. 60/680,645, filed May 12, 2005, and U.S. Provisional Application No. 60/689,206, filed Jun. 9, 2005, both of which are hereby expressly incorporated by reference in their entireties.

STATEMENT REGARDING FEDERALLY SPONSORED R&D

This invention was made in part with United States government support under grant numbers NIH CA87000, awarded by the National Institutes of Health, DAMD 17-03-1-0427 awarded by the US Army, and both BCRP 8WB-017 and TRDRP 11RT-0081 awarded by the State of California. The U.S. Government has certain rights in this invention.

FIELD OF THE INVENTION

Compounds are provided herein that bind to Bcl-2-family member proteins and alter their apoptosis regulatory function. More specifically, the compounds are peptides, peptide analogs and small molecules based on the Nur77 protein or functionally related proteins that mimic the effects of Nur77 by binding Bcl-2 or related anti-apoptotic Bcl-2 family members, converting them to pro-apoptotic or neutral states resulting in apoptosis.

DESCRIPTION OF THE RELATED ART

Apoptosis, also known as programmed cell death, is a physiological process through which the body disposes of unneeded or undesirable native cells. The process of apoptosis is used during development to remove cells from areas where they are no longer required, such as the interior of blood vessels or the space between digits. Apoptosis is also important in the body's response to disease. Cells that are infected with some viruses can be stimulated to undergo apoptosis, thus preventing further replication of the virus in the host organism.

Impaired apoptosis due to blockade of the cell death-signaling pathways is involved in tumor initiation and progression, since apoptosis normally eliminates cells with increased malignant potential such as those with damaged DNA or aberrant cell cycling (White, 1996 *Genes Dev* 10:1-15). The majority of solid tumors are protected by at least one of the two cell death antagonists, Bcl-2 or Bcl-$X_L$. Members of the Bcl-2-family are known to modulate apoptosis in different cell types in response to various stimuli. Some members of the family act to inhibit apoptosis, such as Bcl-2 and Bcl-$X_L$, while others, such as BAX, BAK, Bid, and Bad, promote apoptosis. The ratio at which these proteins are expressed can decide whether a cell undergoes apoptosis or not. For instance, if the Bcl-2 level is higher than the BAX level, apoptosis is suppressed. If the opposite is true, apoptosis is promoted. Bcl-2 overexpression contributes to cancer cell progression by preventing normal cell turnover caused by physiological cell death mechanisms, and has been observed in a majority of cancers (Reed, 1997 *Sem Hematol* 34:9-19; Buolamwini, 1999 *Curr Opin Chem Biol* 3:500-509). The expression levels of Bcl-2 proteins often correlate with resistance to a wide spectrum of chemotherapeutic drugs and γ-radiation therapy. Paradoxically, high levels of Bcl-2 also associate with favorable clinical outcomes for patients with some types of cancers.

Biological approaches targeted at reducing Bcl-2 levels using antisense oligonucleotides have been shown to enhance tumor cell chemosensitivity. Antisense oligonucleotides targeted to Bcl-2 in combination with chemotherapy are currently in phase II/III clinical trials for the treatment of patients with lymphoma and malignant melanoma, and further trials with patients with lung, prostate, renal, or breast carcinoma are ongoing or planned (Reed, 1997 *Sem Hematol* 34:9-19; Piche et al. 1998 *Cancer Res* 2134-2140; Webb et al. 1997 *Lancet* 349:1137-1141; Jansen et al. 1998 *Nat Med* 4:232-234; Waters et al. 2000 *J Clin Oncol* 18:1812-1823). Recently, cell-permeable Bcl-2 binding peptides and chemical inhibitors that target Bcl-2 have been developed, and some of them have been shown to induce apoptosis in vitro and in vivo (Finnegan et al. 2001 *Br J Cancer* 85:115-121; Enyedy et al. 2001 *J Med Chem* 44:4313-4324; Tzung et al. 2001 *Nat Cell Biol* 3:183-191; Degterev et al. 2001 *Nat Cell Bio* 3:173-182; Walensky et al. 2004 *Science* 305: 1466-1470; Oltersdorf et al. 2005 *Nature* 435: 677-681).).

One well-established apoptotic pathway involves mitochondria (Green and Reed, 1998 *Science* 281:1309-1312; Green and Kroemer, 1998 *Trends Cell Biol* 8:267-271). Cytochrome C is exclusively present in mitochondria and is released from mitochondria in response to a variety of apoptotic stimuli. Many Bcl-2-family proteins reside on the mitochondrial outer membrane. Bcl-2 prevents mitochondrial disruption and the release of cytochrome C from mitochondria, while BAX and BAK create pores in mitochondrial membranes and induce cytochrome C release. Recent evidence has indicated, however, that Bcl-2 under certain conditions can function as a pro-apoptotic molecule (Finnegan et al. 2001 *Br J Cancer* 85:115-121; Fujita et al. 1998 *Biochem Biophys Res Commun* 246:484-488; Fadeel et al. 1999 *Leukemia* 13:719-728; Grandgirard et al. 1998 *EMBO J* 17:1268-1278; Cheng et al. 1997 *Science* 278:1966-1968; Del Bello et al. 2001 *Oncogene* 20:4591-4595). Bcl-2 can be cleaved by caspase-3 and thus be converted to a pro-apoptotic protein similar to BAX (Cheng et al. 1997 *Science* 278:1966-1968). Conversely, BAX has also been shown to inhibit neuronal cell death when infected with Sinbis virus (Lewis et al. 1999 *Nat Med* 5:832-835). These observations suggest that members of the Bcl-2-family have reversible roles in the regulation of apoptosis and have the potential to function either as a pro-apoptotic or anti-apoptotic molecule.

Members of the Bcl-2-family of proteins are highly related in one or more specific regions, commonly referred to as Bcl-2 homology (BH) domains. BH domains contribute at multiple levels to the function of these proteins in cell death and survival. The BH3 domain, an amphipathic α-helical domain, was first delineated as a stretch of 16 amino acids in Bak that is required for this protein to heterodimerize with anti-apoptotic members of the Bcl-2-family and to promote cell death. All proteins in the Bcl-2-family contain a BH3 domain, and this domain can have a death-promoting activity that is functionally important. The BH3 domain acts as a potent "death domain" and there is a family of pro-apoptotic proteins that contain BH3 domains which dimerize via those BH3 domains with Bcl-2, Bcl-$X_L$ and other anti-apoptotic members of the Bcl-2 family. Structural studies revealed the presence of a hydrophobic pocket on the surface of Bcl-$X_L$ and Bcl-2 that binds the BH3 peptide. Interestingly, the anti-apoptotic proteins Bcl-$X_L$ and Bcl-2 also possess BH3 domains, but in these anti-apoptotic proteins, the BH3 domain is buried in the core of the protein and not exposed for dimerization (Kelekar and Thompson 1998 *Trends Cell Biol* 8:324). NMR structural analysis of the Bcl-$X_L$/BAK BH3 peptide complex showed that the Bak BH3 domain binds to the hydrophobic cleft formed in part by the BH1, BH2 and BH3 domains of Bcl-$X_L$ (Sattler 1997 *Science* 275:983; Degterev 2001 *Nature Cell Biol* 3:173-182). BH3-domain-mediated homodimerizations and heterodimerizations have a key role in regulating apoptotic functions of the Bcl-2-family (Diaz et al. 1997 *J Biol Chem* 272:11350; Degterev 2001 *Nature Cell Biol* 3:173-182).

The orphan receptor Nur77 (also known as TR3 or nerve growth factor-induced clone B NGFI-B, GenBank Accession No.: L13740, SEQ ID NO: 55) (Chang and Kokontis 1988 *Biochem Biophys Res Commun* 155:971; Hazel et al. 1988 *PNAS USA* 85:8444) functions as a nuclear transcription factor in the regulation of target gene expression (Zhang and Pfahl 1993 *Trends Endocrinol Metab* 4:156-162; Tsai and O'Malley 1994 *Annu Rev Biochem* 63:451; Kastner et al. 1995 *Cell* 83:859; Mageldorf and Evens 1995 *Cell* 83:841). Nur77 was originally isolated as an immediate-early gene rapidly expressed in response to serum or phorbol ester stimulation of quiescent fibroblasts (Hazel et al. 1988 *PNAS USA* 85:8444; Ryseck, et al. 1989 *EMBO J.* 8:3327; Nakai et al. 1990 *Mol Endocrinol* 4:1438; Herschman 1991 *Annul Rev Biochem* 60:281). Other diverse signals, such as membrane depolarization and nerve growth factor, also increase Nur77 expression (Yoon and Lau 1993 *J Biol Chem* 268:9148). Nur77 is also involved in the regulation of apoptosis in different cell types (Woronicz et al. 1994 *Nature* 367:277; Liu et al. 1994 *Nature* 367:281; Weih et al. *PNAS USA* 93:5533; Chang et al, 1997 *EMBO J*16:1865; Li et al. 1998 *Mol Cell Biol* 18:4719; Uemura and Chang 1998 *Endocrinology* 129:2329; Young et al. 1994 *Oncol Res* 6:203). It is rapidly induced during apoptosis of immature thymocytes and T-cell hybridomas (Woronicz et al. 1994 *Nature* 367:277; Liu et al. 1994 *Nature* 367:281), in lung cancer cells treated with the synthetic retinoid 6-[3-(1-adamantyl)-4-hydroxyphenyl]-2-naphthalene carboxylic acid (AHPN) (Li et al. 1998 *Mol Cell Biol* 18:4719) (also called CD437), and in prostate cancer cells treated with different apoptosis inducers (Uemura and Chang 1998 *Endocrinology* 129:2329; Young et al. 1994 *Oncol Res* 6:203). Inhibition of Nur77 activity by overexpression of dominant-negative Nur77 or its antisense RNA inhibits apoptosis, whereas constitutive expression of Nur77 results in massive apoptosis (Weih et al. *PNAS USA* 93:5533; Chang et al, 1997 *EMBO J.* 16:1865).

Further studies of Nur77 have yielded a better understanding of its mechanism of action in apoptosis (Li et al. 2000 *Science* 289:1159). First, several apoptosis inducing agents which also induced Nur77 expression in human prostate cancer cells were identified. These included the AHPN analog 6-[3-(1-adamantyl)-4-hydroxyphenyl]-3-chloro-2-naphthalenecarboxylic acid (MM11453), the retinoid (Z)-4-[2-bromo-3-(5,6,7,8-tetrahydro-3,5,5,8,8-pentamethyl-2-naphthalenyl)propenoyl]benzoic acid (MM11384), the phorbol ester 12-O-tetradecanoyl phorbol-13-acetate (TPA), the calcium ionophore A23187, and the etoposide VP-16. Second, it was found that the transactivation activity of Nur77 was not required for its role in inducing apoptosis, as demonstrated by an experiment that showed that apoptosis inducing agents blocked the expression of a Nur77 target reporter gene. This was further supported by the finding that a Nur77 mutant deprived of its DNA binding domain (DBD) was still competent for inducing apoptosis. Third, Nur77 was found to relocalize to the outer surface of the mitochondria in response to some apoptotic stimuli, and mitochondrial association of Nur77 is essential for its apoptotic effects.

Nur77, visualized in vivo by tagging with Green Fluorescent Protein (GFP), was shown to relocalize from the nucleus to the mitochondria in response to apoptosis-inducing agents. Fractionation studies showed that Nur77 was associating with the mitochondria-enriched heavy membrane fraction, and proteolysis accessibility studies on purified mitochondria confirmed that Nur77 was associating with the outer surface of the mitochondria, where Bcl-2-family members are also found. Fourth, Nur77 was show to be involved in the regulation of cytochrome c release from the mitochondria. Inhibition of Nur77 activity by expression of Nur77 antisense RNA blocked the release of cytochrome c and mitochondrial membrane depolarization in cells stimulated with TPA and NM11453. Furthermore, incubating purified mitochondria with recombinant Nur77 protein resulted in cytochrome c release.

Li et al. (2000 *Science* 289:1159) further explored the function of Nur77 through mutation of the protein. A Nur77 mutant which had the DNA binding domain (amino acid residues 168-467) removed (Nur77/$\Delta$DBD) no longer localized in the nucleus in non-stimulated cells, but instead was consistently found in mitochondria. This localization phenotype was accompanied by a constant release of cytochrome c from the mitochondria. Three other deletion mutants were also generated and assayed: an amino-terminal deletion of 152 amino acids referred to as Nur77/$\Delta$1, a 26 amino acid carboxy-terminal deletion referred to as Nur77/$\Delta$2, and a 120 amino acid carboxy-terminal deletion referred to as Nur77/$\Delta$3. The Nur77/$\Delta$1 protein did not relocalize to the mitochondria in response to TPA, but maintained a nuclear localization. Nur77/$\Delta$1 had a dominant negative effect, preventing the relocalization of full-length Nur77 to the mitochondria and inhibiting apoptosis. Mitochondrial targeting was still observed in Nur77/$\Delta$2 protein expressing cells, but not in Nur77/$\Delta$3 protein cells in response to TPA treatment. These results indicated that carboxy-terminal and amino-terminal sequences are crucial for mitochondrial targeting of Nur77 and its regulation.

Experiments designed to alter the localization of Nur77/$\Delta$DBD by fusing it to various cellular localization signals showed that Nur77 must have access to the mitochondria in order to induce its pro-apoptotic effect. When Nur77/$\Delta$DBD was fused to a nuclear localization sequence, a plasma membrane targeting sequence, or an ER-targeting sequence, Nur77/$\Delta$DBD was not targeted to the mitochondria and no induction of cytochrome c release was observed.

SUMMARY OF THE INVENTION

One aspect of the invention pertains to the discovery of molecules that modulate the activity of Bcl-2-family members in their regulation of apoptosis. More specifically, this aspect relates to regulators of apoptosis which inhibit proteins such as Bcl-2 and related Bcl-2 family members and induce a conformational change in these proteins resulting in pro-apoptotic properties. In this embodiment, the pro-apoptotic modulators of Bcl-2 and related Bcl-2 family members have the formula: Phe-$Xaa_n$-Leu-$Xaa_n$-Leu-$Xaa_n$-Leu, or the formula Leu-$Xaa_n$-Leu-$Xaa_n$-Leu-$Xaa_n$-Phe, where n is between 0 and 3, Xaa can be any amino acid, the compound has 30 or fewer amino acids and wherein the compound induces apoptosis in a mammalian cell expressing Bcl-2 or a Bcl-2 related protein. Any amino acid in the compound of the above formula can be an L- or D-amino acid, or a non-naturally occurring amino acid.

Still another embodiment is a compound that has an amino acid sequence Phe-$Xaa_n$-Leu-$Xaa_n$-Leu-$Xaa_n$-Leu, or Leu-$Xaa_n$-Leu-$Xaa_n$-Leu-$Xaa_n$-Phe, wherein n is between 0 and 3, Xaa is any amino acid, and the compound has one or more D amino acids and wherein the compound induces apoptosis of mammalian cells expressing Bcl-2 or Bcl-2 related proteins.

Another embodiment is a compound that has an amino acid sequence Phe-Xaa$_n$-Leu-Xaa$_n$-Leu-Xaa$_n$-Leu, or Leu-Xaa$_n$-Leu-Xaa$_n$-Leu-Xaa$_n$-Phe, wherein n is between 0 and 3 and Xaa is any amino acid; and a cell-penetrating-peptide, wherein the compound induces apoptosis of mammalian cells expressing Bcl-2 or Bcl-2 related proteins.

Yet another embodiment of the invention is a method of inducing apoptosis in a mammalian cell. The method includes providing the non-naturally occurring compound described above, and then contacting the mammalian cell with an effective amount of the compound, wherein contacting results in apoptosis of said mammalian cell.

Still another embodiment is a method of treating a proliferative disease in a patient, that includes selecting a patient suffering from a proliferative disease; and administering to the patient a therapeutically effective amount of the compound described above.

One other embodiment is the use of the compound descrbed above in the preparation of a medicament for the treatment of a proliferative disease.

The scope of the compositions and methods described herein includes the use of peptides, peptide analogs, and small molecules to regulate the apoptotic effect of Bcl-2-family members.

The scope of the compositions and methods described herein includes the use of antagonists of peptides, peptide analogs, and small molecules to regulate the apoptotic effect of Bcl-2-family members.

Yet another embodiment of the invention is a method of inducing apoptosis in a mammalian cell, comprising contacting the cell with an effective amount of a compound which binds to Bcl-2 and modulates the activity of Bcl-2 so as to be inductive of apoptosis.

Yet another embodiment of the invention is a method of preventing apoptosis in a mammalian cell, comprising contacting the cell with an effective amount of a compound which binds to Bcl-2 and modulates the activity of Bcl-2 so as to be preventive of apoptosis.

BRIEF DESCRIPTION OF THE DRAWINGS

FIG. 15 shows a sequence of a Nur77 fragment, DC-3 (SEQ ID NO: 60). Underlined sequences identify pro-apoptotic sequences that share pro-apoptotic motif.

DETAILED DESCRIPTION

Figure 1:
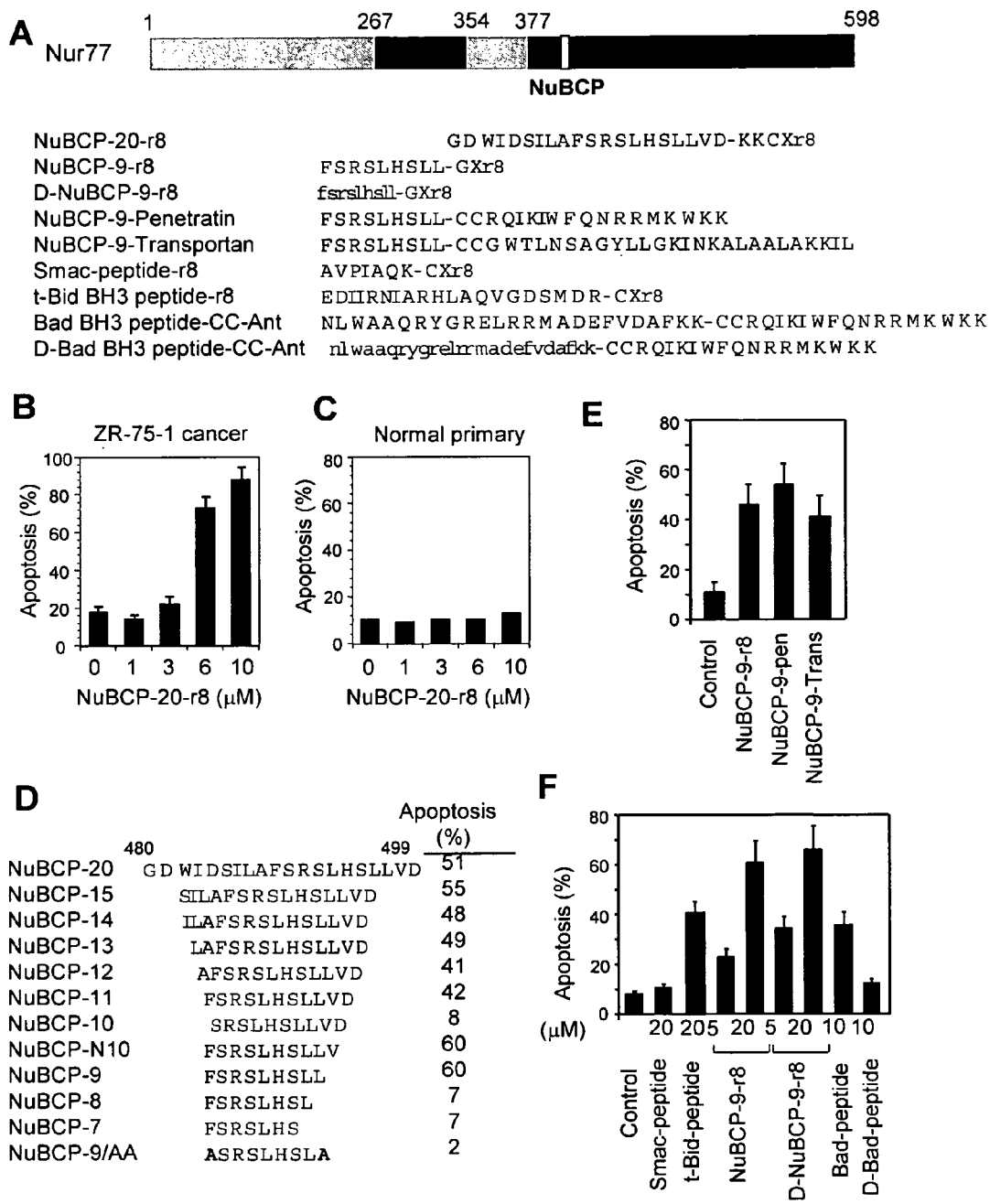
FIG. 1A is a schematic representation of location of Nur77-derived Bcl-2-converting peptides (NuBCP in Nur77) and peptide sequences. NuBCP-20-r8 (SEQ ID NO: 1); NuBCP-9-r8 (SEQ ID NO: 9); D-NuBCP-9-r8 (SEQ ID NO: 13); NuBCP-9-Penetratin (SEQ ID NO: 48); NuBCP-9-Transportan (SEQ ID NO: 54); Smac-peptide-r8 (SEQ ID NO: 56); t-Bid BH3 peptide-r8 (SEQ ID NO: 57); Bad BH3 peptide-CC-Ant (SEQ ID NO: 58); D-Bad BH3 peptide-CC-Ant (SEQ ID NO: 59). Single letter code for amino acid with upper case for L-amino acid and lower case for D-amino acid. X—6-Aminohexanoic acid; CX—covalent linkage between cysteine thiol and acetyl group; CC—disulfide link. Bad peptides were modified by replacing Ser with Ala.
FIG. 1B is a bar graph showing that NuBCP-20-9-r8 causes apoptosis in ZR-75-1 cancer cells. The bars represent means±SD from three independent experiments.
FIG. 1C is a bar graph showing that NuBCP-20-9-r8 does not induce apoptosis in normal primary mammary epithelial cells.
FIG. 1D is a list of NuBCP peptides created by serial deletion analysis of NuBCP-20 and the apoptotic effect of the peptides conjugated with polyarginine (10 μM) in H460 lung cancer cells. NuBCP-20 (SEQ ID NO: 1); NuBCP-15 (SEQ ID NO: 2); NuBCP-14 (SEQ ID NO: 3); NuBCP-13 (SEQ ID NO: 4); NuBCP-12 (SEQ ID NO: 5); NuBCP-11 (SEQ ID NO: 6); NuBCP-10 (SEQ ID NO: 7); NuBCP-N10 (SEQ ID NO: 8); NuBCP-9 (SEQ ID NO:9); NuBCP-8 (SEQ ID NO: 10); NuBCP-7 (SEQ ID NO: 11); NuBCP-9/AA (SEQ ID NO: 12).
FIG. 1E is a bar graph showing apoptotic effect of NuBCP-9-r8 conjugated with CPPs (10 μM) in H460 cells. The bars represent means±SD from three independent experiments.
FIG. 1F is a bar graph showing that apoptotic effect of NuBCP-9-r8 is retained with D-analog in H460 cells. The bars represent means±SD from three independent experiments.

Embodiments of the invention relate to the discovery that Nur77 interaction with Bcl-2 converts Bcl-2 from an anti-apoptotic to a pro-apoptotic molecule by inducing a Bcl-2 conformational change. This finding provides novel and effective approaches to induce cancer cell apoptosis by targeting Bcl-2, as the majority of solid tumors are protected from apoptosis by Bcl-2. Bcl-2 overexpression also contributes to resistance of cancer cells to chemotherapeutic drugs and γ-radiation therapy. Results presented here demonstrated that relatively short Nur77-peptides derived from the Bcl-2-interacting domain in the Nur77 mimic the effect of Nur77 by their ability to induce cancer cell apoptosis through their binding to Bcl-2, targeting mitochondria, and inducing Bcl-2 conformational change. Nur77 was also found to bind other anti-apoptotic Bcl-2 family members, such as Bcl-B and Bfl-1. Nur77 peptides also interacted with these anti-apoptotic proteins.

Nur77-derived peptides induced cellular apoptosis at micro molar concentrations, which is comparable to the currently available peptides derived from the Bcl-2-family protein. Significantly, a peptide with only 9 amino acid residues (NuBCP-9) was sufficient to retain the pro-apoptotic Nur77 function in tumor cells. In addition, the D-enantiomer of NuBCP-9, D-NuBCP-9, was also found to mimic the function of Nur77. Because the NuBCP-9 and D-NuBCP-9 peptides effectively regressed tumor growth in animal models of cancer, they are useful agents for treating Bcl-2-overexpressing cancers.

NuBCP-9 was found to bind to Bcl-2, inducing a Bcl-2 conformational change and extensive apoptosis of cancer cells in vitro and in an in vivo mouse xenograft model. The apoptotic effect of NuBCP-9 was not inhibited but rather potentiated by Bcl-2 overexpression. Furthermore, the functional activities of NuBCP-9 are retained in its all D-amino acid analog. These properties distinguish NuBCP peptides from BH3 peptides and small molecules whose activities are attenuated by Bcl-2, identifying a new approach to target Bcl-2 for cancer treatment.

Several pieces of evidence show that the short Nur77 peptide mimics Nur77 activities. First, a green fluorescent protein (GFP)-fusion Nur77 peptide migrates to mitochondria as visualized by fluorescent spectroscopy. Second, GFP-Nur77 fusion peptide but not GFP binds Bcl-2 directly or indirectly in vivo as shown using immunoprecipitation assays. Third, the cell-permeable Nur77 peptide induces a conformational change in Bcl-2 in vivo as detected by exposure of the Bcl-2 BH3 domain to BH3 antibodies. It was also shown that Nur77 peptide induced apoptosis was Bcl-2 dependent utilizing Bcl-2 siRNA and by comparing activities in matched pairs of cells that either express or do not express Bcl-2.

The Nur77 9-mer peptide was scanned for critical amino acids by substituting each amino acid with alanine and assessing the effect on peptide activity. The critical amino acids mapped to the hydrophobic face of a putative amphipathic alpha helix on Nurr 1. This implies that Nur77 can undergo a conformational change while converting Bcl-2 into a proapoptotic form. Based on the Nur77 9-mer motif, additional Nur77 9-mer peptides, peptides based on homologous Nur-family proteins and additional human cancer related proteins such as p53 were identified that also induce apoptosis in breast cancer cells.

According to one embodiment of the invention, the pro-apoptotic modulator of Bcl-2 is a non-naturally occurring peptide. The peptide can be attached to a carrier group through an amino group of a native amino acid in the peptide, or is attached through the side chain of a lysine amino acid added onto the peptide. It can be appreciated that by providing a linking group —NH—, the carrier can be attached through the carboxylic acid side chain of an aspartic acid or glutamic acid residue by formation of an amide bond; by providing an oxygen linking group on the carrier, the carrier can be attached to the peptide through the carboxylic acid side chain of an aspartic acid or glutamic acid residue, forming an ester bond. Also, the peptides can be terminated with Cys and linked by forming a disulfide bond.

By "non-naturally occurring", it is meant that the compound and/or peptide is artificially produced by chemical synthesis, genetic recombinant methods or enzymatic digestion of isolated polypeptides, and that the compound does not comprise a full length Nur77 polypeptide. The non-naturally occurring peptide may be modified, wherein such modifications include glycosylation, lipidation, amidation, phosphorylation, acetylation, PEGylation (the addition of polyethylene glycol to stabilize the peptide) and albumination (the conjugation of an albumin moiety to increase the biological half-life of the peptide).

According to this embodiment, the amino acid sequence of the peptide inhibitor of Bcl-2 function is identical to the native amino acid sequence of a segment of an endogenous polypeptide inhibitor of Bcl-2, which segment has inhibitory activity to Bcl-2. Wherein said endogenous inhibitor of Bcl-2 has a sequence of e.g., SEQ ID NO: 55. Alternatively, one or more positions of the corresponding native amino acid sequence of the inhibitory peptide can be substituted with other amino acids. The substitutions may include conservative amino acid substitutions. A conservative amino acid substitution is a substitution made within a group of amino acids which are categorized based upon the nature of the amino acid side chain. The seven groups are as follows: (1) non-polar M, I, L and V; (2) aromatic: F, Y and W; (3) basic: K, R and H; (4) non-polar A and G; (5) polar with aliphatic side chains: S and T; (6) polar Q and N; (7) acidic: E and D. According to one embodiment of the invention, each segment has at least 50%, preferably at least 70%, more preferably at least 80%, most preferably at least 90%, sequence identity with the corresponding native segment of the same length. By "sequence identity" is meant the same amino acids in the same relative positions.

In one embodiment, the pro-apoptotic modulator of Bcl-2 has the following general formula: F $Xaa_n$ L $Xaa_n$ L $Xaa_n$ L, wherein n is 0-3, and Xaa is any amino acid. The amino acids can be substituted for synthetic or non-naturally occurring amino acids as described herein. For example, any L-amino acid can be replaced with an equivalent D-amino acid. Alanine can replace any interior (Xaa) amino acid. Any alanine substitutable interior amino acid (Xaa) can be removed, i.e. SRS and HS can be deleted one by one or in any combination thereof. Alanine-substitutable amino acids can be replaced with spatially equivalent linkers.

The pro-apoptotic modulator of Bcl-2 can be linked to cell-penetrating peptide sequences such as penetratin, transportan or tat either directly or though intervening sequences. In addition, they can be linked to peptides that target cancer cells direction or through intervening sequences. For example, the pro-apoptotic modulator of Bcl-2 can be linked through GX to a cyclic disulfide loop peptide, Lyp-1, that binds specifically to breast cancer cells. Alternatively, the pro-apoptotic modulator of Bcl-2 can be linked through GX to F3, a 31-residue peptide that binds specifically to breast cancer cells. The additional examples of cell-permeability enhancers that can be conjugated to the pro-apoptotic modulator of Bcl-2 are provided below. The peptides can also have the inverso-configuration.

A compound of the invention may have the following length prior to being conjugated to a cell-permeability enhancer: 4-597 amino acids, preferably 4-400 amino acids, preferably 4-300 amino acids, preferably 4-200 amino acids, preferably 4-100 amino acids, preferably 4-50 amino acids, preferably 4-40 amino acids, preferably 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4 amino acids. In one embodiment, the compound has fewer than 30, 25, 20, 15 or 10 amino acids.

Exemplary pro-apoptotic modulators of Bcl-2 as well as the previous nomenclature of the peptides are listed below. As shown in Table 1, the peptide labels have changed over time. Table 1 lists the previous names of each peptide, and the current name of the same peptide.

TABLE 1

Exemplary pro-apoptotic modulators of Bcl-2

| Previous Name | Current Name | Pro-apoptotic modulator of Bcl-2 Sequence | SEQ ID NO: |
|---|---|---|---|
| TR3 peptide; Nur77 peptide | NuBCP-20-r8 | acetyl---GDWIDSILAFSRSLHSLLVDKKC-X-rrrrrrrr | 1 |
| Nur77-15 | NuBCP-15 | acetyl--------SILAFSRSLHSLLVDGXrrrrrrrr-amide | 2 |
| Nur77-14 | NuBCP-14 | acetyl---------ILAFSRSLHSLLVDGXrrrrrrrr-amide | 3 |
| Nur77-13 | NuBCP-13 | acetyl----------LAFSRSLHSLLVDGXrrrrrrrr-amide | 4 |
| Nur77-12 | NuBCP-12 | acetyl-----------AFSRSLHSLLVDGXrrrrrrrr-amide | 5 |
| Nur77-11 | NuBCP-11 | acetyl------------FSRSLHSLLVDGXrrrrrrrr-amide | 6 |
| Nur77-10 | NuBCP-10 | acetyl-------------SRSLHSLLVDGXrrrrrrrr-amide | 7 |
| Nur77-N10 | NuBCP-N10 | acetyl------------FSRSLHSLLVGXrrrrrrrr-amide | 8 |
| TR3/1; Nur77-9 | NuBCP-9-r8, Nur77/1 | acetyl------------FSRSLHSLLGXrrrrrrrr-amide | 9 |
| Nur77-8 | NuBCP-8 | acetyl------------FSRSLHSLGXrrrrrrrr-amide | 10 |
| Nur77-7 | NuBCP-7 | acetyl------------FSRSLHSGXrrrrrrrr-amide | 11 |
| Nur77-9/AA | NuBCP-9/AA | acetyl------------ASRSLHSLAGXrrrrrrrr-amide | 12 |

TABLE 1-continued

Exemplary pro-apoptotic modulators of Bcl-2

| Pro-apoptotic modulator of Bcl-2 | | | SEQ ID NO: |
|---|---|---|---|
| Previous Name | Current Name | Sequence | |
| TR3/1(D) | D-NuBCP-9-r8 | acetyl------------fsrslhsllGXrrrrrrrr-amide | 13 |
| TR3/1 (inverso) | Nur77/1 (inverso) | acetyl------------LLSHLSRSFGXrrrrrrrr-amide | 14 |
| TR3/1(retro-inverso) | Nur77/1(retro-inverso) | acetyl------------llshlsrsfGXrrrrrrrr-amide | 15 |
| TR3/2 | Nur77/2 | acetyl------------FGDWIDSILGXrrrrrrrr-amide | 16 |
| TR3/3 | Nur77/3 | acetyl------------FAALSALVLGXrrrrrrrr-amide | 17 |
| TR3/4 | Nur77/4 | acetyl------------FYLKLEDLVGXrrrrrrrr-amide | 18 |
| NOR1 peptide | Nor1 peptide | acetyl--------SIKDFSLNLQSLNLDG rrrrrrrr-amide | 19 |
| Nurr1 | NOT peptide | acetyl---SIVEFSSNLQNMNIDG rrrrrrrr-amide | 20 |
| TR3/1 (embedded) | Nur77/1 (embedded) | acetyl----rrrFrrrLrrLL-amide | 21 |
| TR3/1: (D/embedded) | Nur77/1 (D/embedded) | acetyl----rrrfrrrlrrll-amide | 22 |
| | | acetyl-------fSrSlHsLlGXrrrrrrrr-amide | 23 |
| | | acetyl-------fSRslHSllGXrrrrrrrr-amide | 24 |
| | | acetyl-------FARSLHSLLGXrrrrrrrr-amide | 25 |
| | | acetyl-------FSASLHSLLGXrrrrrrrr-amide | 26 |
| | | acetyl-------FSRALHSLLGXrrrrrrrr-amide | 27 |
| | | acetyl-------FSRSLASLLGXrrrrrrrr-amide | 28 |
| | | acetyl-------FSRSLHALLGXrrrrrrrr-amide | 29 |
| | | acetyl-------F_RSLHSLLGXrrrrrrrr-amide | 30 |
| | | acetyl-------FS_SLHSLLGXrrrrrrrr-amide | 31 |
| | | acetyl-------FSR_LHSLLGXrrrrrrrr-amide | 32 |
| | | acetyl-------FSRSL_SLLGXrrrrrrrr-amide | 33 |
| | | acetyl-------FSRSLH_LLGXrrrrrrrr-amide | 34 |
| | | acetyl-------F__SLHSLLGXrrrrrrrr-amide | 35 |
| | | acetyl-------f_rslhsllGXrrrrrrrr-amide | 36 |
| | | acetyl-------FXSLHSLLGXrrrrrrrr-amide | 37 |
| | | acetyl-------FSRSLHSLLGX(CGNKRTAC)-amide | 38 |
| | | acetyl---FSRSLHSLLGXAKVKDEPQRRSARLSAKPAPPKPEPPPKKAPAKK-amide | 39 |
| | Nur77/short | acetyl---F__L_LLGXrrrrrrrr-amide | 40 |
| | Nur77/short D | acetyl---f__l_llGXrrrrrrrr-amide | 41 |
| | Nur77/1 Ant | acetyl---FSRSLHSLLC—CRQIKIWFQNRRMKWKK-amide | 42 |
| | Nur77/Ant (D) | acetyl---fsrslhsllc—crqvkvwfqnrrmkwkk-amide | 43 |
| | p53 peptide | acetyl---FSD_LWKLL-GXrrrrrrrr-amide | 44 |

TABLE 1-continued

Exemplary pro-apoptotic modulators of Bcl-2

Pro-apoptotic modulator of Bcl-2

| Previous Name | Current Name | Sequence | SEQ ID NO: |
|---|---|---|---|
| | Nur77 (embedded2) | acetyl-NFQHALQEVLQALKQVQAR-C—C-rrrrrrrr-amide | 45 |
| | Nur77/1 (D/L) | acetyl---fSrSlHsLl-GXrrrrrrrr-amide | 46 |
| | Nur77/1 (DD/LL) | acetyl---fSRslHSll-GXrrrrrrrr-amide | 47 |
| Nur77/1 Penetratin | NuBCP-9-Penetratin | acetyl---FSRSLHSLL-(C—C)RQIKIWFQNRRMKWKK-amide | 48 |
| | Nur77/1 (D)Penetratin(D) | acetyl---fsrslhsll-(c—c)rqvkvwfqnrrmkwkk-amide | 49 |
| | Nur77/1 Transportan10 | acetyl---FSRSLHSLL-(C—C)AGYLLGKINLKALAALAKKIL-amide | 50 |
| | Nur77/1(D) Transportan10(D) | acetyl---fsrslhsll-(c—c)agyllgkvnlkalaalakkvl-amide | 51 |
| | Nur77/1(L/D) Transportan10 (L/D): | acetyl---FsRsLhSlL-(c-C)aGyLlGkInLkAlAaLaKkIl-amide | 52 |
| | Nur77/1 (LLDD) Transportan10 (LLDD) | acetyl---FSrSLHslL-(C-c)aGYllGKvnLKalAalaKkvl-amide | 53 |
| | NuBCP-9-Transportan | acetyl---FSRSLHSLL-CCGWTLNSAGYLLGKINKALAALAKKIL-amide | 54 |

Single letter code is used for L-amino acids (capitalized), while D-amino acids are lower case. Substituted and added amino acids are in bold. r is aminoacid Arginine. X is 6-aminohexanoic acid. The C—X bond is formed from the reaction of a C-terminal Cys thiol group with a chloracetylated aminohexanoyl group. C—C bond is formed by the oxidation of two cysteine amino acids to form a disulfide bond. Brackets ( ) indicate that the two cysteines oxidize to form a disulfide loop.

In one embodiment, the analog shares at least about 50%, at least about 60%, at least about 70%, at least about 80%, at least about 90%, sequence identity with the peptides listed above.

Peptides which bind the Bcl-2 pocket can be identified by a Bcl-2 competition binding assay. The assay is based on fluorescence polarization. The assay can rapidly measure Bcl-2 receptor-ligand interaction without using filter binding, electrophoresis, or precipitation steps. Fluorescence polarization gives a direct, instantaneous equilibrium measure of the bound/free ratio between ligand and receptor molecules.

Peptides, peptide analogs, peptidomimetics and small molecules which bind Bcl-2 and induce a Bcl-2 conformational change that is indicative of its pro-apoptotic form can be identified using CD spectroscopy.

The cell permeability of a conjugate can be verified by directly or indirectly labeling the conjugate with a detectable label which can be visualized inside a cell with the aid of microscopy. For example, a fluorescein derivative of the conjugate can be made by methods well known to those skilled in the art for conjugating fluorescein molecules to peptides. The fluorescein conjugate is incubated with the relevant target cells in vitro. The cells are harvested and fixed, then stained with Streptavidin-fluorescein and observed in the dark under confocal microscopy. Internalization of the exogenous molecule to which the carrier is conjugated is apparent by fluorescence.

For peptide conjugates, the peptide portion can be a recombinant peptide, a natural peptide, or a synthetic peptide. The peptide can also be chemically synthesized, using, for example, solid phase synthesis methods.

I. Definitions and General Parameters

The following definitions are set forth to illustrate and define the meaning and scope of the various terms used to describe the invention herein.

As used herein, "pharmaceutically or therapeutically acceptable carrier" refers to a carrier medium which does not interfere with the effectiveness of the biological activity of the active ingredients and which is not toxic to the host or patient.

As used herein, "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers can have an optical rotation that is so slight that it is undetectable with present instrumentation. The compounds described herein can have one or more asymmetrical carbon atoms and therefore include various stereoisomers. All stereoisomers are included within the scope of the present invention.

As used herein, "therapeutically- or pharmaceutically-effective amount" as applied to the disclosed compositions refers to the amount of composition sufficient to induce a desired biological result. That result can be alleviation of the signs, symptoms, or causes of a disease, or any other desired alteration of a biological system. For example, the result can involve a decrease and/or reversal of cancerous cell growth.

As used herein, "homology" or "identity" or "similarity" refers to sequence similarity between two peptides or between two nucleic acid molecules. Homology can be determined by comparing a position in each sequence which can be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. An "unrelated" or "non-homologous" sequence shares less than about 40% identity, though preferably less than about 25% identity, with one of the sequences described herein.

As used herein, the term "inhibitor" is interchangeably used to denote "antagonist". Both these terms define compositions which have the capability of decreasing certain enzyme activity or competing with the activity or function of a substrate of said enzyme.

As used herein "peptide" indicates a sequence of amino acids linked by peptide bonds.

The term "peptidomimetic" means that a peptide according to the invention is modified in such a way that it includes at least one non-coded residue or non-peptidic bond.

Such modifications include, e.g., alkylation and, more specifically, methylation of one or more residues, insertion of or replacement of natural amino acid by non-natural amino acids, and replacement of an amide bond with other covalent bond. A peptidomimetic can optionally comprise at least one bond which is an amide-replacement bond such as urea bond, carbamate bond, sulfonamide bond, hydrazine bond, or any other covalent bond. The design of appropriate "peptidomimetic" can be computer assisted.

The term "spacer" denotes a chemical moiety whose purpose is to link, covalently, a cell-permeability moiety and a peptide or peptidomimetic. The spacer can be used to allow distance between the cell-permeability moiety and the peptide, or it is a chemical bond of any type. Linker denotes a direct chemical bond or a spacer.

The term "core" refers to the peptidic segment or moiety of the pro-apoptotic modulator of Bcl-2 which comprises peptide or peptidomimetic and is optionally attached to a cell-permeability enhancer.

The term "permeability" refers to the ability of an agent or substance to penetrate, pervade, or diffuse through a barrier, membrane, or a skin layer. "Cell permeability" or a "cell-penetration" moiety refers to any molecule known in the art which is able to facilitate or enhance penetration of molecules through membranes. Non-limiting examples include: hydrophobic moieties such as lipids, fatty acids, steroids and bulky aromatic or aliphatic compounds; moieties which can have cell-membrane receptors or carriers, such as steroids, vitamins and sugars, natural and non-natural amino acids and transporter peptides. Examples for lipid moieties which can be used are: Lipofectamine; Transfectace; Transfectam; Cytofectin; DMRIE; DLRIE; GAP-DLRIE; DOTAP; DOPE; DMEAP; DODMP; DOPC; DDAB; DOSPA; EDLPC; EDMPC; DPH; TMADPH; CTAB; lysyl-PE; DC-Cho; -alanyl cholesterol; DCGS; DPPES; DCPE; DMAP; DMPE; DOGS; DOHME; DPEPC; Pluronic; Tween; BRIJ; plasmalogen; phosphatidylethanolamine; phosphatidylcholine; glycerol-3-ethylphosphatidylcholine; dimethyl ammonium propane; trimethyl ammonium propane; diethylammonium propane; triethylammonium propane; dimethyldioctadecylammonium bromide; a sphingolipid; sphingomyelin; a lyso-lipid; a glycolipid; a sulfatide; a glycosphingolipid; cholesterol; cholesterol ester; cholesterol salt; oil; N-succinyldioleoylphosphatidylethanolamine; 1,2-dioleoyl-sn-glycerol; 1,3-dipalmitoyl-2succinylglycerol; 1,2-dipalmitoyl-sn-3-succinylglycero; 1-hexadecyl-2-palmitoylglycerophosphatidylethanolamine; palmitoylhomocysteine; N,N'-Bis(do-decyaminocarbonylmethylene)-N,N'-bis((-N,N,N-trimethylammoniumethyl-aminocarbonylmethylene)ethylenediamine tetraiodide; N,N" Bis (hexadecylaminocarbonylmethylene)-N,N',N"-tris((-N,N, N-trimethylammonium-ethylaminocarbonylmethylenediethylenetriaminehexaiodide; N,N'-Bis(dodecylaminocarbonylmethylene)-N,N"-bis((-N, N,N-trimethylammoniumethylamino-carbonylmethylene) cy-clohexylene-1,4-diaminetetra-iodide; 1,7,7-tetra-((N,N, N,N-tetramethylammoniu methylamino-carbonylmethylene)-3-hexadecylaminocarbonyl methylene-1,3,7-triaazaheptane heptaiodide; N,N,N',N'-tetra((—N,N,N-trimethylammonium-ethylaminocarbonylmethylene)-N'-(1, 2-dioleoylglycero-3-phosphoethanolaminocarbonyl methylene)diethylenetriamine tetraiodide; dioleoylphosphatidyl ethanolamine; a fatty acid; a lysolipid; phosphatidylcholine; phosphatidylethanolamine; phosphatidylserine; phosphatidylglycerol; phosphatidylinositol; a sphingolipid; a glycolipid; a glucolipid; a sulfatide; a glycosphingolipid; phosphatidic acid; palmitic acid; stearic acid; arachidonic acid; oleic acid; a lipid bearing a polymer; a lipid bearing a sulfonated saccharide; cholesterol; tocopherol hemisuccinate; a lipid with an ether-linked fatty acid; a lipid with an ester-linked fatty acid; a polymerized lipid; diacetyl phosphate; stearylamine; cardiolipin; a phospholipid with a fatty acid of 6-8 carbons in length; a phospholipid with asymmetric acyl chains; 6-(5cholesten-3b-yloxy)-1-thio-b-D-galactopyranoside; digalactosyldiglyceride; 6-(5-cholesten-3b-yloxy)hexyl-6-amino-6-deoxy-1-thio-b-D-galactopyranoside; 6-(5-cholesten-3b-yloxy)hexyl-6-amino-6-deoxyl-1-thio-a-D-mannopyranoside; 12-(((7'-diethylamino-coumarin-3-yl) carbonyl)methylamino)-octadecanoic acid; N-[12-(((7'-diethylaminocoumarin-3-yl)carbonyl)methyl-amino) octadecanoyl];-2-aminopalmitic acid; cholesteryl(4'-trimethyl-ammonio)butanoate; N-succinyldioleoylphosphatidylethanolamine; 1,2-dioleoyl-sn-glycerol; 1,2-dipalmitoyl-sn-3-succinyl-glycerol; 1,3-dipalmitoyl-2-succinylglycerol; 1-hexadecyl-2-palmitoylglycero-phosphoethanolamine; palmitoylhomocysteine; cyclic 9-amino-acid peptide as described in Laakkonen et al. 2002 *Nature Med* 8:751-755; a peptide described in Porkka et al. 2002 *PNAS USA* 99:7444-7449; and polymers of L- or D-arginine as described in Mitchell et al. 2000 *J Peptide Res* 56:318-325.

As used herein, "cancer" and "cancerous" refer to any malignant proliferation of cells in a mammal.

As used herein, "neurodegenerative disease" is a condition which affects brain function and is a result of deterioration of neurons. The neurodegenerative diseases are divided into two groups: a) conditions causing problems with movements, and conditions affecting memory and conditions related to dementia. Neurodegenerative diseases include, for example, Huntington's disease, spinocerebellar ataxias, Machado-Joseph disease, Spinal and Bulbar muscular atrophy (SBMA or Kennedy's disease), Dentatorubral Pallidoluysian Atrophy (DRPLA), Fragile X syndrome, Fragile XE mental retardation, Friedreich ataxia, myotonic dystrophy, Spinocerebellar ataxias (types 8, 10 and 12), spinal muscular atrophy (Werdnig-Hoffman disease, Kugelberg-Welander disease), Alzheimer's disease, amyotrophic lateral sclerosis, Parkinson's disease, Pick's disease, and spongiform encephalopathies. Additional neurodegenerative diseases include, for example, age-related memory impairment, agyrophilic grain dementia, Parkinsonism-dementia complex of Guam, auto-immune conditions (e.g., Guillain-Barre syndrome, Lupus), Biswanger's disease, brain and spinal tumors (including neurofibromatosis), cerebral amyloid angiopathies, cerebral palsy, chronic fatigue syndrome, corticobasal degeneration, conditions due to developmental dysfunction of the CNS parenchyma, conditions due to developmental dysfunction of the cerebrovasculature, dementia—multi infarct, dementia—subcortical, dementia with Lewy bodies, dementia of human immunodeficiency virus (HIV), dementia lacking distinct histology, Dementia Pugilistica, diseases of the eye, ear and vestibular systems involving neurodegeneration (including macular degeneration and glaucoma), Down's syndrome, dyskinesias (Paroxysmal), dystonias, essential tremor, Fahr's syndrome, fronto-temporal dementia and Parkinsonism linked to chromosome 17 (FTDP-17), frontotemporal lobar degeneration, frontal lobe dementia, hepatic encephalopathy, hereditary spastic paraplegia, hydrocephalus, pseudotumor cerebri and other conditions involving CSF dysffunction, Gaucher's disease, Hallervorden-Spatz disease, Korsakoffs syndrome, mild cognitive impairment, monomeric amyotrophy, motor neuron diseases, multiple system atrophy, multiple sclerosis and other demyelinating conditions (e.g., leukodystrophies), myalgic encephalomyelitis, myoclonus, neurodegeneration induced by chemicals, drugs and toxins, neurological manifestations of AIDS including AIDS dementia, neurological/cognitive manifestations and consequences of bacterial and/or viral infections, including but not restricted to enteroviruses, Niemann-Pick disease, non-Guamanian motor neuron disease with neurofibrillary tangles, non-ketotic hyperglycinemia, olivo-ponto cerebellar atrophy, oculopharyugeal muscular dystrophy, neurological manifestations of Polio myelitis including non-paralytic polio and post-polio-syndrome, primary lateral sclerosis, prion diseases including Creutzfeldt-Jakob disease (including variant form), kuru, fatal familial insomnia, Gerstmann-Straussler-Scheinker disease and other transmissible spongiform encephalopathies, prion protein cerebral amyloid angiopathy, postencephalitic Parkinsonism, progressive muscular atrophy, progressive bulbar palsy, progressive subcortical gliosis, progressive supranuclear palsy, restless leg syndrome, Rett syndrome, Sandhoff disease, spasticity, sporadic fronto-temporal dementias, striatonigral degeneration, subacute sclerosing panencephalitis, sulphite oxidase deficiency, Sydenham's chorea, tangle only dementia, Tay-Sach's disease, Tourette's syndrome, vascular dementia, Wilson disease, Alexander disease, Alper's disease, ataxia telangiectasia, Canavan disease, Cockayne syndrome, Krabbe disease, multiple system atrophy, Pelizaeus-Merzbacher Disease, primary lateral sclerosis, Refsum's disease, Sandhoff disease, Schilder's disease, Steele-Richardson-Olszewski disease, tabes dorsalis.

When two compounds are administered in combination or used in combination therapy according to the invention the term "combination" in this context means that the drugs are given contemporaneously, either simultaneously or sequentially. This term is exchangeable with the term "coadministration" which in the context of this invention is defined to mean the administration of more than one therapeutic in the course of a coordinated treatment to achieve an improved clinical outcome. Such coadministration can also be coextensive, that is, occurring during overlapping periods of time.

In addition to peptides consisting only of naturally-occurring amino acids, peptidomimetics or peptide analogs are also considered. Peptide analogs are commonly used in the pharmaceutical industry as non-peptide drugs with properties analogous to those of the template peptide. These types of non-peptide compounds are termed "peptide mimetics" or "peptidomimetics" (see, e.g., Luthman et al. 1996 *A Textbook of Drug Design and Development*, 14:386-406, 2nd Ed., Harwood Academic Publishers; Grante 1994 *Angew Chem Int Ed Engl* 33:1699-1720; Fauchere 1986 *Adv Drug Res* 15:29; Evans et al. 1987 *J Med Chem* 30:229). Peptide mimetics that are structurally similar to therapeutically useful peptides can be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —$CH_2$ NH—, —$CH_2$ S—, —$CH_2$—$CH_2$—, —CH=CH—(cis and trans), —$COCH_2$—, —CH(OH)$CH_2$—, and —$CH_2$ SO—, by methods known in the art and further described in the following references: Spatola, 1983, *In: Chemistry and Biochemistry of Amino Acids, Peptides, and Proteins*, B. Weinstein, eds., Marcel Dekker, New York, p.267; Hudson et al. 1979 *Int J Pept Prot Res* 14:177-185 (1979) (—$CH_2$NH—, $CH_2$ $CH_2$—); Spatola et al. 1986 *Life Sci* 38:1243-1249 (—$CH_2$—S); Hann 1982 *J Chem Soc Perkins Trans I*, 307-314 (—CH—CH—, cis and trans); Almquist et al. 1980 *J Med Chem* 23:1392-1398 (—$COCH_2$—); Jennings-White et al. 1982 *Tetrahedron Lett* 23:2533 (—$COCH_2$—); Szelke, et al. European Appln. EP 45665 (1982) (—CH(OH)$CH_2$—); Holladay et al. 1983 *Tetrahedron Lett* 24:4401-4404 (—C(OH)$CH_2$—); and Hruby, 1982 *Life Sci* 31:189-199 (—$CH_2$—S—); each of which is incorporated herein by reference. A particularly preferred non-peptide linkage is —$CH_2$NH—. Such peptide mimetics can have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivatization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) can be used to generate more stable peptides. In addition, constrained peptides comprising a consensus sequence or a substantially identical consensus sequence variation can be generated by methods known in the art (Rizo, et al. 1992 *Annu Rev Biochem* 61:387, incorporated herein by reference); for example, by adding internal cysteine residues capable of forming intramolecular disulfide bridges which cyclize the peptide.

Synthetic or non-naturally occurring amino acids refer to amino acids which do not naturally occur in vivo but which, nevertheless, can be incorporated into the peptide structures described herein. Preferred synthetic amino acids are the D-α-amino acids of naturally occurring L-α-amino acid as well as non-naturally occurring D- and L-α-amino acids represented by the formula $H_2NCHR^5 COOH$ where $R^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5)-alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —$C(O)R^2$ where $R^2$ is selected from the group consisting of hydrogen, hydroxy, lower alkyl, lower alkoxy, and —$NR^3R^4$ where $R^3$ and $R^4$ are independently selected from the group consisting of hydrogen and lower alkyl, (g) —$S(O)_nR^6$ where n is an integer from 1 to 2 and $R^6$ is lower alkyl and with the proviso that $R^5$ does not define a side chain of a naturally occurring amino acid.

Other preferred synthetic amino acids include amino acids wherein the amino group is separated from the carboxyl group by more than one carbon atom such as beta (β)-alanine, gamma (γ)-aminobutyric acid, and the like.

Particularly preferred synthetic amino acids include, by way of example, the D-amino acids of naturally occurring L-amino acids, L-(1-naphthyl)-alanine, L-(2-naphthyl)-alanine, L-cyclohexylalanine, L-2-aminoisobutyric acid, the sulfoxide and sulfone derivatives of methionine (i.e., HOOC—$(H_2NCH)CH_2 CH_2$—$S(O)_nR^6$) where n and $R^6$ are as defined above as well as the lower alkoxy derivative of methionine (i.e., HOOC—$(H_2NCH)CH_2 CH_2$—$OR^6$ where $R^6$ is as defined above).

II. Overview

Compounds that bind to Bcl-2-family members and alter their function in apoptosis are also provided. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor.

The examples described herein demonstrate that the nuclear-to-mitochondrial pathway of Nur77 can be extended to lung and breast cancer cells. In addition, it is shown that Bcl-2 acts as a mitochondrial receptor of Nur77 through their physical interaction. In response to various apoptotic stimuli, the expression of the Nur77 protein is increased and its localization is altered from nuclear to cytoplasmic, more specifically to the outer member of mitochondria. This association with the mitochondria is the result of binding to the Bcl-2, whose normal function is the inhibition of apoptosis, particularly the inhibition of the release of cytochrome c from the mitochondria. High expression of Nur77/ΔDBD (a form of Nur77 without its DNA-binding domain) induced cytochrome c release and apoptosis only in cells expressing Bcl-2, indicating that Nur77 modulates the function of Bcl-2 from anti-apoptotic to pro-apoptotic, without cleaving the Bcl-2 protein.

Further data show that Nur77 induces a conformational change in Bcl-2 which can cause the function of Bcl-2 to be modified from an anti-apoptotic to a pro-apoptotic protein. Mutational analysis indicated that the C-terminal domain of Nur77, which contains several α-helices, is responsible for interacting with Bcl-2. The C-terminal domain, DC3, and a shortened C-terminal domain, DC1, was sufficient for interacting with Bcl-2 and inducing apoptotic potential of Bcl-2. When analyzing the Bcl-2 domains involved in the interaction, it was observed that mutations in the hydrophobic pocket of Bcl-2 did not affect its interaction with Nur77. Moreover, the N-terminal domain of Bcl-2, containing the loop region and BH4 domain, was able to interact with Nur77/ΔDBD. Deletion of BH4 domain from Bcl-2 did not affect the interaction of Nur77/ΔDBD with Bcl-2, implying that the loop region of Bcl-2 was responsible for interaction. In addition, DC1 and BH3-only Bcl-Gs did not compete for binding to Bcl-2. Instead, Bcl-Gs enhanced the binding of DC1 to Bcl-2. Thus, Bcl-2 was found to interact with Nur77 in a manner that is different from its interaction with Bcl-2-family proteins containing only the BH3 domain.

Specific interaction of Nur77 with Bcl-2 is essential for Nur77 to target mitochondria and results in conversion of Bcl-2 from an anti-apoptotic to a pro-apoptotic molecule. Concomitantly, the conformation of Bcl-2 is changed by Nur77 resulting in the exposure of the otherwise hidden BH3 domain. Thus, embodiments of the invention include peptides derived from the specific Bcl-2-interacting domain of Nur77, such as DC3, which mimic its effect. Embodiments also include homologous sequences from functionally related proteins. EThese embodiments include peptide analogs, peptidomimetics and small molecules designed to mimic the binding properties of these peptides. Peptides, peptide analogs, peptidomimetics, and small molecules that specifically interact with Bcl-2 will effectively induce apoptosis of cancer cells, thus restricting tumor growth. In addition, the results provide a molecular basis for developing various agents for treating cancers and other therapeutic applications.

III. Preparation of Peptides and Peptide Mimetics

Preferred peptides can be synthesized using any method known in the art, including peptidomimetic methodologies. These methods include solid phase as well as solution phase synthesis methods. The conjugation of the peptidic and permeability moieties can be performed using any methods known in the art, either by solid phase or solution phase chemistry. Non-limiting examples for these methods are described herein. Some of the preferred compounds disclosed herein can conveniently be prepared using solution phase synthesis methods. Other methods known in the art to prepare compounds like those described herein, can be used and are within the scope of the present invention.

The amino acids used are those which are available commercially or are available by routine synthetic methods. Certain residues can require special methods for incorporation into the peptide, and either sequential, divergent or convergent synthetic approaches to the peptide sequence are useful in this invention. Natural coded amino acids and their derivatives are represented by three-letter codes according to IUPAC conventions.

When there is no indication, the L isomer was used. The D isomers are indicated by lower case font.

Conservative substitutions of amino acids as known to those skilled in the art are within the scope of the present invention. Conservative amino acid substitutions includes replacement of one amino acid with another having the same type of functional group or side chain e.g., aliphatic, aromatic, positively charged, negatively charged. These substitutions can enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

| | |
|---|---|
| Aromatic | Phenylalanine |
| | Tryptophan |
| | Tyrosine |
| Ionizable: Acidic | Aspartic acid |
| | Glutamic Acid |
| Ionizable: Basic | Arginine |
| | Histidine |
| | Lysine |
| Nonionizable Polar | Asparagine |
| | Glutamine |
| | Serine |
| | Cysteine |
| | Threonine |
| Nonpolar (Hydrophobic) | Alanine |
| | Glycine |
| | Isoleucine |
| | Leucine |
| | Methionine |
| | Proline |
| | Valine |
| Sulfur Containing | Cysteine |
| | Methionine |

The following is a list of non limiting examples of non-coded amino acids: Abu refers to 2-aminobutyric acid, Ahx6 refers to aminohexanoic acid, Ape5 refers to aminopentanoic acid, ArgOl refers to argininol, βAla refers to β-Alanine, Bpa refers to 4-Benzoylphenylalanine, Bip refers to Beta (4-biphenyl)-alanine, Dab refers to diaminobutyric acid, Dap refers to Diaminopropionic acid, Dim refers to Dimethoxyphenylalanine, Dpr refers to Diaminopropionic acid, Hol refers to homoleucine, HPhe refers to Homophenylalanine, GABA refers to gamma aminobutyric acid, GlyNH$_2$ refers to Aminoglycine, Nle refers to Norleucine, Nva refers to Norvaline, Orn refers to Ornithine, PheCarboxy refers to para carboxy Phenylalanine, PheC1 refers to para chloro Phenylalanine, PheF refers to para fluoro Phenylalanine, PheMe refers to pare methyl Phenylalanine, PheNH2 refers to pare amino Phenylalanine, PheNO2 refers to para nitro Phenylalanine, Phg refers to Phenylglycine, Thi refers to Thienylalanine.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyldiimidazole, various active esters, e.g., esters of N-hydroxyphthalimide or N-hydroxy-succinimide, and the various cleavage reagents, e.g., trifluoroacetic acid (TEA), HCl in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures (see Merrifield, 1963 *J Amer Chem Soc* 85:2149-54; and 1965 *Science* 50:178-85). Additional information about the solid phase synthesis procedure can be had by reference to the treatise by Steward and Young (Solid Phase Peptide Synthesis, W. H. Freeman & Co., San Francisco, 1969, and the review chapter by Merrifield in Advances in Enzymology 32:221-296, F. F. Nold, Ed., Interscience Publishers, New York, 1969; and Erickson and Merrifield, The Proteins 2:255 et seq. (ea. Neurath and Hill), Academic Press, New York, 1976. The synthesis of peptides by solution methods is described in Neurath et al., eds. (The Proteins, Vol. II, 3d Ed., Academic Press, NY (1976)).

Crude peptides can be purified using preparative high performance liquid chromatography. The amino terminus can be blocked according, for example, to the methods described by Yang et al. 1990 *FEBS Lett* 272:61-64.

Peptide synthesis includes both manual and automated techniques employing commercially available peptide synthesizers. The peptides described herein can be prepared by chemical synthesis and biological activity can be tested using the methods disclosed herein.

The peptides described herein can be synthesized in a manner such that one or more of the bonds linking amino acid residues are non-peptide bonds. These non-peptide bonds can be formed by chemical reactions well known to those skilled in the art. In yet another embodiment of the invention, peptides comprising the sequences described above can be synthesized with additional chemical groups present at their amino and/or carboxy termini, such that, for example, the stability, bio-availability, and/or inhibitory activity of the peptides is enhanced. For example, hydrophobic groups such as carbobenzoxyl, dansyl, or t-butyloxycarbonyl groups, can be added to the peptides' amino terminus. Likewise, an acetyl group or a 9-fluorenylmethoxy-carbonyl group can be placed at the peptides' amino terminus. Additionally, the hydrophobic group, t-butyloxycarbonyl, or an amido group, can be added to the peptides' carboxy terminus.

In addition, the peptides can be engineered to contain additional functional groups to promote cell uptake. For example, carbohydrate moieties such as glucose or xylose can be attached to the peptide, such as by attachment to the hydroxyl function of a serine or threonine amino acid of the peptide.

Further, the peptides of the invention can be synthesized such that their stearic configuration is altered. For example, the D-isomer of one or more of the amino acid residues of the peptide can be used, rather than the usual L-isomer. Still further, at least one of the amino acid residues of the peptide can be substituted by one of the well known non-naturally occurring amino acid residues. Alterations such as these can serve to increase the stability, bioavailability and/or inhibitory action of the peptides.

A. Solid Phase Synthesis

The peptides disclosed herein can be prepared by classical methods known in the art, for example, by using standard solid phase techniques. The standard methods include exclusive solid phase synthesis, partial solid phase synthesis methods, fragment condensation, classical solution synthesis, and even recombinant DNA technology (see, e.g., Merrifield 1963 *J Am Chem Soc* 85:2149). On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO- BEADS SX-1™ by Bio Rad Laboratories (Richmond, Calif.) and the preparation of the hydroxymethyl resin is described by Bodonszky et al. 1966 *Chem Ind* (London) 38:1597. The benzhydrylamine (BHA) resin has been described by Pietta and Marshall 1970 *Chem Comm* 650, and is commercially available from Beckman Instruments, Inc. (Palo Alto, Calif.) in the hydrochloride form.

Thus, the compounds disclosed herein can be prepared by coupling an alpha-amino protected amino acid to the chloromethylated resin with the aid of, for example, a cesium bicarbonate catalyst, according to the method described by Gisin, 1973 *Helv Chim Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc and Fmoc are preferred protecting groups. The side-chain protecting group remains intact during coupling and is not split off during the deprotection of the amino-terminus protecting group or during coupling. The side-chain protecting group must be removable upon the completion of the synthesis of the final peptide and under reaction conditions that will not alter the target peptide.

The side-chain protecting groups for Tyr include tetrahydropyranyl, tert-butyl, trityl, benzyl, Cbz, Z—Br—Cbz, and 2,5-dichlorobenzyl. The side-chain protecting groups for Asp include benzyl, 2,6-dichlorobenzyl, methyl, ethyl, and cyclohexyl. The side-chain protecting groups for Thr and Ser include acetyl, benzoyl, trityl, tetrahydropyranyl, benzyl, 2,6-dichlorobenzyl, and Cbz. The side-chain protecting group for Thr and Ser is benzyl. The side-chain protecting groups for Arg include nitro, Tosyl (Tos), Cbz, adamantyloxycarbonyl mesitoylsulfonyl (Mts), or Boc. The side-chain protecting groups for Lys include Cbz, 2-chlorobenzyloxycarbonyl (2Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by Stewart and Young, *Solid Phase Peptide Syntheses* (2nd Ed., Pierce Chemical Company, 1984).

B. Synthetic Amino Acids

These procedures can also be used to synthesize peptides in which amino acids other than the 20 naturally occurring, genetically encoded amino acids are substituted at one, two, or more positions of any of the compounds described herein. For instance, naphthylalanine can be substituted for tryptophan, facilitating synthesis. Other synthetic amino acids that can be substituted into the peptides include L-hydroxypropyl, L-3,4-dihydroxy-phenylalanyl, amino acids such as L-α-hydroxylysyl and D-α-methylalanyl, L-α-methylalanyl, β amino acids, and isoquinolyl. D amino acids and non-naturally occurring synthetic amino acids can also be incorporated into the peptides.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides by phosphorylation (see, e.g., Bannwarth et al. 1996 *Bioorg Med Chem Letters* 6:2141-2146), and other methods for making peptide derivatives of the compounds disclosed herein are described in Hruby et al. 1990 *Biochem J* 268:249-262. Thus, the peptide compounds can also serve as a basis to prepare peptide mimetics with similar biological activity.

C. Terminal Modifications

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis (see, e.g., Morgan et al. 1989 *Ann Rep Med Chem* 24:243-252). The following describes methods for preparing peptide mimetics modified at the N-terminal amino group, the C-terminal carboxyl group, and/or changing one or more of the amido linkages in the peptide to a non-amido linkage. It being understood that two or more such modifications can be coupled in one peptide mimetic structure (e.g., modification at the C-terminal carboxyl group and inclusion of a —CH$_2$-carbamate linkage between two amino acids in the peptide).

1. N-Terminal Modifications

The peptides typically are synthesized as the free acid but, as noted above, could be readily prepared as the amide or ester. One can also modify the amino and/or carboxy terminus of the peptide compounds to produce other compounds. Amino terminus modifications include methylation (i.e., —NHCH$_3$ or —NH(CH$_3$)$_2$), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (see, e.g., Murray et al. 1995 *Burger's Medicinal Chemistry and Drug Discovery*, 5th Ed., Vol. 1, Wolf, ed., John Wiley and Sons, Inc.). Specifically, the N-terminal amino group can then be reacted as follows:

a) to form an amide group of the formula RC(O)NH— where R is as defined above by reaction with an acid halide (e.g., RC(O)Cl) or symmetric anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—; or b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane) (see, for example, Wollenberg et al., U.S. Pat. No. 4,612,132 which is incorporated herein by reference in its entirety). It is understood that the succinic group can be substituted with, for example, C$_2$-C$_6$ alkyl or —SR substituents which are prepared in a conventional manner to provide for substituted succinimide at the N-terminus of the peptide. Such alkyl substituents are prepared by reaction of a lower olefin (C$_2$—C) with maleic anhydride in the manner described by Wollenberg et al., supra and —SR substituents are prepared by reaction of RSH with maleic anhydride where R is as defined above; or c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—Cl in a suitable inert diluent (e.g., dichloromethane) preferably containing a tertiary amine to scavenge the acid generated during the reaction; or d) to form a sulfonamide group by reaction with an equivalent amount or an excess (e.g., 5 equivalents) of R—S(O)$_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes); or e) to form a carbamate group by reaction with an equivalent amount or an excess (e.g., 5 equivalents) of R—OC(O)Cl or R—OC(O)OC$_6$H$_4$-p-NO$_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); or f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

2. C-Terminal Modifications

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR$^3$, R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O) NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides herein, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the peptide compounds, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in their binding activity. Nonproteinaceous polymers suitable for use include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weights of about 5,000 daltons, 10,000 daltons and 20,000 daltons.

The peptide compounds can be derivatized with or coupled to such polymers using, but not limited to, any of the methods set forth in Zallipsky, 1995 *Bioconjugate Chem* 6:150-165 and Monfardini et al. 1995 *Bioconjugate Chem* 6:62-69, all of which are incorporated by reference in their entirety herein.

In a presently preferred embodiment, the peptide compounds are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the peptide compounds can be either branched or unbranched. (see, e.g., Monfardini et al. 1995 *Bioconjugate Chem* 6:62-69). PEGs are commercially available from Shearwater Polymers, Inc. (Huntsville, Ala.), Sigma Chemical Co. and other companies. Such PEGs include, but are not limited to, monomethoxypolyethylene glycol (MePEG-OH), monomethoxypolyethylene glycolsuccinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM).

Briefly, in one exemplar embodiment, the hydrophilic polymer which is employed, e.g., PEG, is preferably capped at one end by an unreactive group such as a methoxy or ethoxy group. Thereafter, the polymer is activated at the other end by reaction with a suitable activating agent, such as cyanuric halides (e.g., cyanuric chloride, bromide or fluoride), diimadozle, an anhydride reagent (e.g., a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound disclosed or taught herein to produce a peptide compound derivatized with a polymer. Alternatively, a functional group in the peptide compounds can be activated for reaction with the polymer, or the two groups can be joined in a concerted coupling reaction using known coupling methods. It will be readily appreciated that the peptide compounds can be derivatized with PEG using a myriad of reaction schemes known to and used by those of skill in the art.

In addition to derivatizing the peptide compounds with a hydrophilic polymer (e.g., PEG), it has been discovered that other small peptides, e.g., other peptides or ligands that bind to a receptor, can also be derivatized with such hydrophilic polymers with little, if any, loss in biological activity (e.g., binding activity, agonist activity, antagonist activity, etc.). It has been found that when these small peptides are derivatized with a hydrophilic polymer, their solubility and circulation half-lives are increased and their immunogenicity is decreased. Again, quite surprisingly, the foregoing can be accomplished with little, if any, loss in biological activity. In fact, in preferred embodiments, the derivatized peptides have an activity that is 0.1 to 0.01-fold that of the unmodified peptides. In more preferred embodiments, the derivatized peptides have an activity that is 0.1 to 1-fold that of the unmodified peptides. In even more preferred embodiments, the derivatized peptides have an activity that is greater than the unmodified peptides.

Peptides suitable for use in this embodiment generally include those peptides, i.e., ligands that bind to members of the Bcl-2 receptor family. Such peptides typically comprise about 150 amino acid residues or less and, more preferably, about 100 amino acid residues or less (e.g., about 10-12 kDa), even more preferably about 10 amino acids or less. Hydrophilic polymers suitable for use herein include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have average molecular weights of about 5,000 daltons, 10,000 daltons and 20,000 daltons. The peptide compounds can be derivatized with using the methods described above and in the cited references.

D. Backbone Modifications

Other methods for making peptide derivatives of the compounds described herein are described in Hruby et al. 1990 *Biochem J* 268:249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis (see Morgan et al. 1989 *Ann Rep Med Chem* 24:243-252, incorporated herein by reference). These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —CH$_2$-carbamate linkage, a phosphonate linkage, a —CH$_2$-sulfonamide linkage, a urea linkage, a secondary amine (—CH$_2$NH—) linkage, and an alkylated peptidyl linkage [—C(O)NR$^6$—where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O) NR— linkage in the peptide with a —CH$_2$-carbamate linkage (—CH$_2$ OC(O)NR—), then the carboxyl (—COOH) group of a suitably protected amino acid is first reduced to the —CH$_2$ OH group which is then converted by conventional methods to a —OC(O)Cl functionality or a para-nitrocarbonate —OC (O)O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC(O) NR— linkage. For a more detailed description of the formation of such —CH$_2$-carbamate linkages, see Cho et al., 1993, *Science* 261:1303-1305.

Similarly, replacement of an amido linkage in the peptide with a phosphonate linkage can be achieved in the manner set forth in U.S. patent application Ser. Nos. 07/943,805, 08/081, 577 and 08/119,700, the disclosures of which are incorporated herein by reference in their entirety.

Replacement of an amido linkage in the peptide with a —CH$_2$-sulfonamide linkage can be achieved by reducing the carboxyl (—COOH) group of a suitably protected amino acid to the —CH$_2$ OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(O)$_2$ Cl functional group which replaces the carboxyl group of the otherwise suitably protected amino acid. Use of this suitably protected amino acid analogue in peptide synthesis provides for inclusion of an —CH$_2$ S(O)$_2$ NR— linkage which replaces the amido linkage in the peptide thereby providing a peptide mimetic. For a more complete description on the conversion of the carboxyl group of the amino acid to a —CH$_2$ S(O)$_2$ Cl group, see, for example, Weinstein, *Chemistry & Biochemistry of Amino Acids, Peptides and Proteins*, Vol. 7, pp. 267-357, Marcel Dekker, Inc., New York (1983) which is incorporated herein by reference.

Replacement of an amido linkage in the peptide with a urea linkage can be achieved in the manner set forth in U.S. patent application Ser. No. 08/147,805, which is incorporated herein by reference.

Secondary amine linkages wherein a CH$_2$NH linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$ CH$_2$ NHCH$_2$ COOH which is then used in N-protected form in the next coupling reaction. The preparation of such analogues by reduction of the carbonyl group of the amido linkage in the dipeptide is well known in the art (see, e.g., Remington, 1994 *Meth Mol Bio* 35:241-247).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

One can also cyclize the peptides described herein, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

E. Disulfide Bond Formation

The compounds described herein can exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues can also be substituted with a homocysteine.

Other embodiments of this invention provide for analogs of these disulfide derivatives in which one of the sulfurs has been replaced by a CH$_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The compounds can be cyclized or dimerized via displacement of the leaving group by the sulfur of the cysteine or homocysteine residue. See, e.g., Andreu et al. 1994 *Meth Mol Bio* 35:91-169; Barker et al. 1992 *J Med Chem* 35:2040-2048; and Or et al. 1991 *J Org Chem* 56:3146-3149, each of which is incorporated herein by reference.

Alternatively, the peptides can be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in Maniatis (Molecular Cloning, Cold Spring Harbor Laboratories, 1982), and in Sambrook (Molecular Cloning, Cold Spring Harbor Laboratories, Second Ed., 1989), and in Ausubel (Current Protocols in Molecular Biology, Wiley and Sons, 1987), which are incorporated by reference.

The peptides can be labeled, for further use as biomedical reagents or clinical diagnostic reagents. For example, a peptide of the invention can be conjugated with a fluorescent reagent, such as a fluorescein isothiocyanate (FITC), tetramethylrhodamine isothiocyanate (TRITC), or other fluorescent. The fluorescent reagent can be coupled to the peptide through the peptide N-terminus or free amine side chains by any one of the following chemistries, where R is the fluorescent reagent:

Alternatively, the peptide can be radiolabeled by peptide radiolabeling techniques well-known to those skilled in the art.

IV. Methods for Screening Peptides, Analogs, and Small Molecules that Modulate Bcl-2-Family Member Protein Activity The assays described herein are designed to identify compounds that interact with (e.g., bind to) Bcl-2 and other members of the Bcl-2-family of proteins, and modify their ability to regulate apoptosis. This regulation can be by mimicking Nur77, by inducing an equivalent conformation change, by enhancing the Nur77 effect or by inhibiting the Nur77 effect.

The compounds which can be screened include, but are not limited to peptides, fragments thereof, and other organic compounds (e.g., peptidomimetics) that bind to the Bcl-2-family member and either mimic the activity triggered by the natural regulatory ligand (e.g., Nur77), enhance the activity triggered by the natural regulatory ligand or inhibit the activity triggered by the natural ligand; as well as peptides, antibodies or fragments thereof, and other organic compounds that mimic the binding domain of the Bcl-2-family member and bind to and "neutralize" natural ligand.

Such compounds include, but are not limited to, peptides such as, for example, soluble peptides, including but not limited to members of random peptide libraries; (see, e.g., Lam et al. 1991 *Nature* 354:82-84; Houghten et al. 1991 *Nature* 354:84-86), and combinatorial chemistry-derived molecular libraries made of D- and/or L-configuration amino acids, phosphopeptides (including, but not limited to, members of random or partially degenerate, directed phosphopeptide libraries; see, e.g., Songyang et al. 1993 *Cell* 72:767-778), antibodies including, but not limited to, polyclonal, monoclonal, humanized, anti-idiotypic, chimeric or single chain antibodies, and FAb, $F(ab')_2$ and FAb expression library fragments, and epitope-binding fragments thereof, and small organic or inorganic molecules.

Computer modeling and searching technologies permit identification of compounds, or the improvement of already identified compounds that can modulate Bcl-2-family member activity. Having identified such a compound or composition, the active sites or regions are identified. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which can increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential Bcl-2-family member modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Bcl-2 and related proteins will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al. 1988 *Acta Pharm Fennica* 97:159-166; McKinaly and Rossmann 1989 *Annu Rev Pharmacol Toxicol* 29:111-122; Perry and Davies, *OSAR: Quantitative Structure-Activity Relationships in Drug Design*, pp. 189-193, Alan R. Liss, Inc. (1989); Lewis and Dean 1989 *Proc R Soc Lond* 236:125-140 and 141-162; and, with respect to a model receptor for nucleic acid components, Askew et al. 1989 *J Am Chem Soc* 111: 1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

One could also screen libraries of known compounds, including natural products or synthetic chemicals, and biologically active materials, including proteins, for compounds which exhibit binding properties similar to those of Nur77.

One could also screen libraries of known compounds, including natural products or synthetic chemicals, and biologically active materials, including proteins, for compounds which enhance or inhibit the activity of or binding of Nur77 to Bcl-22 or related Bcl-2 family members.

Once identified, these compounds can be subjected to assays such as those described in the examples to identify whether the compounds increase apoptosis or decrease apoptosis in cells.

Compounds identified via assays such as those described herein can be useful, for example, in inducing or inhibiting apoptosis.

V. In Vitro Screening Assays for Compounds that Bind to Bcl-2-Family Member Proteins In vitro systems can be designed to identify compounds capable of interacting with (e.g., binding to) Bcl-2-family members. Compounds identified can be useful, for example, in modulating the activity of wild type and/or mutant Bcl related proteins; can be useful in elaborating the biological function of the Bcl related proteins; can be utilized in screens for identifying compounds that disrupt normal Bcl-2-family member interactions; or can in themselves disrupt such interactions.

The principle of the assays used to identify compounds that bind to the Bcl-2-family member involves preparing a reaction mixture of the protein and the test compound under conditions and for a time sufficient to allow the two components to interact and bind, thus forming a complex which can be removed and/or detected in the reaction mixture.

The screening assays can be conducted in a variety of ways. For example, one approach would involve anchoring the Bcl-2 related protein, polypeptide, peptide or fusion protein or the test substance to a solid phase, and detecting complexes of Bcl-2 related protein bound to test compounds anchored on the solid phase. In one embodiment, the Bcl-2 related reactant can be anchored to a solid surface and the test compound, which is not anchored, can be labeled, either directly or indirectly. Bound compound(s) could then be detected by various methods such as mass spectrometry after elution from the bound protein. In another embodiment, the binding specificity of test compounds can be tested using a competition assay as follows: a) Bcl-2 or related Bcl-2 family member is anchored to a solid phase; b) immobilized Bcl-2 or related Bcl-2 family member is incubated with Nur77 peptide labeled with a fluorescent tag or other reporter molecule, in the presence or absence of compounds being tested; c) after incubation under suitable conditions, the solid phase is washed to remove unbound reactants; d) the amount of labeled Nur77 peptide bound to the solid phase is measured for each reaction; and e) the amount of labeled Nur77 peptide bound in the presence of various test compounds is compared with the amount of labeled Nur77 peptide bound in the absence of test compounds, and the ability of each test compound to compete for Bcl-2 or related Bcl-2 family member binding sites is determined.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, can be directly labeled or indirectly labeled with a labeled anti-Ig antibody).

Alternatively, a reaction can be conducted in a liquid phase, the reaction products separated from unreacted components, and complexes detected, e.g., using an immobilized antibody specific for the Bcl related protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with Bcl-2-family members or compounds that enhance or inhibit the interaction of Bcl-2 or related Bcl-2 family members with Nur77 or Nur77 peptide. To this end, cell lines that express Bcl related proteins, or cell lines (e.g., COS cells, CHO cells, fibroblasts, etc.) that have been genetically engineered to express Bcl-2 related proteins (e.g., by transfection or transduction of DNA) can be used.

VI. Structure-Based Drug Design

To aid in the characterization and optimization of compounds which can alter the activity of Bcl-2-family proteins, structure-based drug design has become a useful tool. Solution nuclear magnetic resonance (NMR) techniques can be used to map the interactions between the BH3 domain of the Bcl-2-family protein and chemical compounds that target these anti-apoptotic proteins. NMR chemical shift perturbation is an efficient tool for rapid mapping of interaction interfaces on proteins. Structure-activity relationships (SAR) can be obtained by using nuclear magnetic resonance (NMR), using the method known as "SAR by NMR" (Shuker et al. 1996 *Science* 274:1531; Lugovskoy et al. 2002 *J Am Chem Soc* 124:1234). SAR by NMR can be used to identify, optimize and link together small organic molecules that bind to proximal subsites of a protein to produce high-affinity ligands.

In using NMR to structurally characterize protein-protein and ligand-protein interactions, isotope labeling can result in increased sensitivity and resolution, and in reduced complexity of the NMR spectra. The three most commonly used stable isotopes for macromolecular NMR are $^{13}$C, $^{15}$N and $^{2}$H. Isotope labeling has enabled the efficient use of heteronuclear multi-dimensional NMR experiments, providing alternative approaches to the spectral assignment process and additional structural constraints from spin-spin coupling. Uniform isotope labeling of the protein enables the assignment process through sequential assignment with multidimensional triple-resonance experiments and supports the collection of conformational constraints in de novo protein structure determinations (Kay et al. 1990 *J Magn Reson* 89:496; Kay et al. 1997 *Curr Opin Struct Biol* 7:722). These assignments can be used to map the interactions of a ligand by following chemical-shift changes upon ligand binding. In addition, intermolecular NOE (nuclear Overhauser effect) derived intermolecular distances can be obtained to structurally characterize protein-ligand complexes.

In addition to uniform labeling, selective labeling of individual amino acids or labeling of only certain types of amino acids in proteins can result in a dramatic simplification of the spectrum and, in certain cases, enable the study of significantly larger macromolecules. For example, the methyl groups of certain amino acids can be specifically labeled with $^{13}$C and $^{1}$H in an otherwise fully $^{2}$H-labeled protein. This results in well resolved heteronuclear [$^{13}$C, $^{1}$H]-correlation spectra, which enables straightforward ligand-binding studies either by chemical shift mapping or by protein methyl-ligand inter-molecular NOEs, thus providing key information for structure-based drug design in proteins as large as 170 kDa (Pellecchia et al. 2002 *Nature Rev Drug Discovery* 1:211). 2D [$^{13}$C, $^1$H]-HMQC (heteronuclear multiple quantum coherence) and $^{13}$C-edited [$^1$H,$^1$H]-NOESY NMR experiments on a ligand-receptor complex can be used to detect binding, determine the dissociation constant for the complex, and provide a low-resolution model based on the available three-dimensional structure of the target, thus revealing the relative position of the ligand with respect to labeled side-chains.

Thus, NMR can be used to identify molecules that induce apoptosis. Compounds can be screened for binding to labeled Bcl-XL, for example. Such labels include $^{15}$N and $^{13}$C. The interaction between the compound and Bcl-XL, and therefore its ability to induce apoptosis, are determined via NMR.

VII. Gene Therapy

Nucleic acid encoding Nur77, and deletions, truncations and variations thereof, as well as any other peptides identified by the methods above can be used in gene therapy. In gene therapy applications, genes are introduced into cells in order to achieve in vivo synthesis of a therapeutically effective product, for example the replacement of a defective gene. "Gene therapy" includes both conventional gene therapy where a lasting effect is achieved by a single treatment, and the administration of gene therapeutic agents, which involve the one time or repeated administration of a therapeutically effective DNA or mRNA. Antisense RNAs and DNAs can be used as therapeutic agents for blocking the expression of certain genes in vivo. It has been shown that short antisense oligonucleotides can be imported into cells where they act as inhibitors, despite their low intracellular concentrations caused by their restricted uptake by the cell membrane (Zamecnik et al. 1986 *PNAS USA* 83:4143-4146). The oligonucleotides can be modified, e.g., by substituting their negatively charged phosphodiester groups by uncharged groups.

There are a variety of techniques available for inducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include, but are not limited to, the use of liposomes, electroporation, microinjection, cell fusion, DEAE-dextran, and calcium phosphate precipitation method. The currently preferred in vivo gene transfer techniques include transfection with viral (typically retroviral) vectors and viral coat protein-liposome mediated transfection (Dzau et al., 1993, *Trends in Biotechnology* 11, 205-210). In some situations it is desirable to provide the nucleic acid source with an agent that targets the target cell, such as an antibody specific for a cell surface membrane protein or the target cell, or a ligand for a receptor on the target cell. Where liposomes are employed, proteins which bind to a cell surface membrane protein associated with endocytosis can be used for targeting and/or to facilitate uptake, e.g. capsid proteins or fragments thereof that are tropic for a particular cell type, antibodies for proteins which undergo internalization in cycling, and proteins that target intracellular localizations and enhance intracellular half-life. The technique of receptor-mediated endocytosis is described, e.g., by Wu et al. 1987 *J Biol Chem* 262:4429-4432 and Wagner et al. 1990 *PNAS USA* 87:3410-3414. For review of gene therapy protocols see Anderson et al. 1992 *Science* 256:808-813.

Given the teachings set forth herein, the skilled artisan can select among various vectors and other expression/delivery elements depending on such factors as the site and route of administration and the desired level and duration of expression.

For example, naked plasmid DNA can be introduced into muscle cells, for example, by direct injection into the tissue. (Wolff et al., 1989, *Science* 247:1465).

DNA-Lipid Complexes—Lipid carriers can be associated with naked DNA (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold 1989 *Nature* 337:387). Intravenous injection of cationic lipid-plasmid complexes into mice has been shown to result in expression of the DNA in lung (Brigham et al. 1989 *Am J Med Sci* 298:278). See also, Osaka et al. 1996 *J Pharm Sci* 85:612-618; San et al. 1993 *Human Gene Therapy* 4:781-788; Senior et al. 1991 *Biochim Biophys Acta* 1070:173-179; Kabanov and Kabanov 1995 *Bioconjugate Chem* 6:7-20; Remy et al. 1994 *Bioconjugate Chem* 5:647-654; Behr 1994 *Bioconjugate Chem* 5:382-389; Behr et al. 1989 *PNAS USA* 86:6982-6986; and Wyman et al. 1977 *Biochem* 36:3008-3017.

Adenovirus-based vectors for the delivery of transgenes are well known in the art and can be obtained commercially or constructed by standard molecular biological methods. Recombinant adenoviral vectors containing exogenous genes for transfer are, generally, derived from adenovirus type 2 (Ad2) and adenovirus type 5 (Ad5). They can also be derived from other non-oncogenic serotypes. See, e.g., Horowitz, "*Adenoviridae and their Replication*" in *Virology*, 2d Ed., Fields et al. eds., Raven Press Ltd., New York (1990) incorporated herein by reference.

It has been shown that Nur77 peptides specifically interact with Bcl-2-family receptors, resulting in the conversion of these molecules from anti-apoptotic to pro-apoptotic. These studies provide a molecular basis for developing various anti-cancer drugs and other therapeutic agents.

VII. Pharmacology

In one embodiment, methods for treating cancer by inducing apoptosis of cancer cells in an afflicted individual are provided. Accordingly, one or more inducers of apoptosis of the invention, targeting an intracellular death antagonist (e.g., Nur77 peptide or peptidomimetic) is administered to a patient in need of such treatment. A therapeutically effective amount of the drug can be administered as a composition in combination with a pharmaceutical vehicle. In other embodiments of the invention the apoptosis modulator targets a death antagonist associated with virally infected cells or self-reacting lymphocytes to comprise a treatment for viral infection or autoimmune disease.

For a review of apoptosis in the pathogenesis of disease, see Thompson, 1995 *Science* 267:1456-1462.

In particular, pro-apoptotic modulators of Bcl-2 or related Bcl-2 family members can be used to treat any condition characterized by the accumulation of cells which are regulated by Bcl-2 or related Bcl-2 family members. By "regulated by Bcl-2" with respect to the condition of a cell is meant that the balance between cell proliferation and apoptotic cell death is controlled, at least in part, by Bcl-2 or related Bcl-2 family members. For the most part, the cells express or over-express Bcl-2 or related Bcl-2 family members. Enhancement of Bcl-2 or related Bcl-2 family members expression has been demonstrated to increase the resistance of cells to almost any apoptotic signal (Hockenbery et al. 1990 *Nature* 348:334;

Nunez et al. 1990 *Immunol* 144:3602; Vaux et al. 1988 *Nature* 335:440; Hockenbery et al. 1993 *Cell* 75:241; Ohmori et al. 1993 *Res Commun* 192:30; Lotem et al. 1993 *Cell Growth Differ* 4:41; Miyashita et al. 1993 *Blood* 81:115). Principally, the proliferative disorders associated with the inhibition of cell apoptosis include cancer, autoimmune disorders and viral infections. Overexpression of Bcl-2 or related Bcl-2 family members specifically prevents cells from initiating apoptosis in response to a number of stimuli (Hockenbery et al. 1990 *Nature* 348:334; Nunez et al. 1990 *J Immunol* 144:3602; Vaux et al. 1988 *Nature* 335:440; Hockenbery et al. 1993 *Cell* 75:241). The induction of genes that inhibit Bcl-2 or related Bcl-2 family members can induce apoptosis in a wide variety of tumor types, suggesting that many tumors continually rely on Bcl-2 or related gene products to prevent cell death. Expression of Bcl-2 or related Bcl-2 family members has been associated with a poor prognosis in at least prostatic cancer, colon cancer and neuroblastoma (McDonnell et al. 1992 Cancer Res 52:6940; Hague et al. 1994 *Oncogene* 9:3367; Castle et al. 1993 *Am J Pathol* 143:1543). Bcl-2 or the related gene has been found to confer resistance to cell death in response to several chemotherapeutic agents (Ohmon et al. 1993 *Res Commun* 192:30; Lotem et al. 1993 *Cell Growth Differ* 4:41; Miyashita et al. 1993 *Blood* 81:115).

Physiologic cell death is important for the removal of potentially autoreactive lymphocytes during development and for the removal of excess cells after the completion of an immune response. Failure to remove these cells can result in autoimmune disease. A lupus-like autoimmune disease has been reported in transgenic mice constitutively overexpressing Bcl-2 or related Bcl-2 family members in their B cells (Strasser et al. 1991 *PNAS USA* 88:8661). Linkage analysis has established an association between the Bcl-2 locus and autoimmune diabetes in non-obese diabetic mice (Garchon et al. 1994 *Eur J Immunol* 24:380). The compositions described herein which comprise inhibitors of Bcl-2 function can be used to induce apoptosis of self-reactive lymphocytes. By "self-reactive" is meant a lymphocyte which participates in an immune response against antigens of host cells or host tissues.

Compositions comprising pro-apoptotic modulators of Bcl-2 or related Bcl-2 family members can be used in the treatment of viral infection, to induce apoptosis of virally infected cells. Viruses have developed mechanisms to circumvent the normal regulation of apoptosis in virus-infected cells, and these mechanisms have implicated Bcl-2 or related Bcl-2 family members. For example, the E1B 19-kDa protein is instrumental in the establishment of effective adenoviral infection. The apoptosis-blocking ability of E1B can be replaced in adenoviruses by Bcl-2 (Boyd et al. 1994 *Cell* 79:341). Genes of certain other viruses have been shown to have sequence and functional homology to Bcl-2 (Neilan et al. 1993 *J Virol* 67:4391; Henderson et al. 1993 *PNAS USA* 90:8479). The viral gene LMP-1 specifically upregulates Bcl-2 providing a survival advantage over latently infected cells (Henderson et al. 1991 *Cell* 65:1107). Sindbis infection is dependent on the host cell's expression of Bcl-2 (Levine et al. 1993 *Nature* 361:739).

Apart from other considerations, the fact that the novel active ingredients of the compositions described herein are peptides, peptide analogs or peptidomimetics, dictates that the formulation be suitable for delivery of these type of compounds. Clearly, peptides are less suitable for oral administration due to susceptibility to digestion by gastric acids or intestinal enzymes. The preferred routes of administration of peptides are intra-articular, intravenous, intramuscular, subcutaneous, intradermal, or intrathecal. A more preferred route is by direct injection at or near the site of disorder or disease. However, some of the compounds disclosed herein were proved to be highly resistance to metabolic degradation in addition to having the ability to cross cell membrane. These properties make them potentially suitable for oral administration. Pharmaceutical compositions as described herein can be manufactured by processes well known in the art, e.g., by means of conventional mixing, dissolving, granulating, grinding, pulverizing, dragee-making, levigating, emulsifying, encapsulating, entrapping or lyophilizing processes.

Toxicity and therapeutic efficacy of the pro-apoptotic modulators of Bcl-2 described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in humans. The dosage can vary depending upon the dosage form employed and the route of administration utilized. The exact formulation, route of administration and dosage can be chosen by the individual physician in view of the patient's condition (e.g., Fingl et al. 1975, in "The Pharmacological Basis of Therapeutics", Ch. 1 Al; and Remington's Pharmaceutical Sciences, by Joseph P. Remington, Mack Pub. Co. 1985).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The targeted cell can be solitary and isolated from other like cells (such as a single cell in culture or a metastatic or disseminated neoplastic cell in viva), or the targeted cell can be a member of a collection of cells (e.g., within a tumor). Preferably, the cell is a neoplastic cell (e.g., a type of cell exhibiting uncontrolled proliferation, such as cancerous or transformed cells). Neoplastic cells can be isolated (e.g., a single cell in culture or a metastatic or disseminated neoplastic cell in vivo) or present in an agglomeration, either homogeneously or, in heterogeneous combination with other cell types (neoplastic or otherwise) in a tumor or other collection of cells. Where the cell is within a tumor, some embodiments described herein provide a method of retarding the growth of the tumor by administering pro-apoptotic modulator of Bcl-2 to the tumor and subsequently administering a cytotoxic agent to the tumor.

By virtue of the cytopathic effect on individual cells, the inventive method can reduce or substantially eliminate the number of cells added to the tumor mass over time. Preferably, the inventive method effects a reduction in the number of cells within a tumor, and, most preferably, the method leads to the partial or complete destruction of the tumor (e.g., via killing a portion or substantially all of the cells within the tumor).

Where the targeted cell is associated with a neoplastic disorder within a patient (e.g., a human), some embodiments of the invention provide a method of treating the patient by first administering a pro-apoptotic modulator of Bcl-2 or related Bcl-2 family members to the patient ("pretreatment") and subsequently administering a cytotoxic agent to the patient. This approach is effective in treating mammals bearing intact or disseminated cancer. For example, where the cells are disseminated cells (e.g., metastatic neoplasia), the cytopathic effects of the inventive method can reduce or substantially eliminate the potential for further spread of neoplastic cells throughout the patient, thereby also reducing or minimizing the probability that such cells will proliferate to form novel tumors within the patient. Furthermore, by retarding the growth of tumors including neoplastic cells, the inventive method reduces the likelihood that cells from such tumors will eventually metastasize or disseminate. Of course, when the inventive method achieves actual reduction in tumor size (and especially elimination of the tumor), the method attenuates the pathogenic effects of such tumors within the patient. Another application is in high-dose chemotherapy requiring bone marrow transplant or reconstruction (e.g., to treat leukemic disorders) to reduce the likelihood that neoplastic cells will persist or successfully regrow.

In many instances, the pretreatment of cells or tumors with pro-apoptotic modulator of Bcl-2 or related Bcl-2 family members before treatment with the cytotoxic agent effects an additive and often synergistic degree of cell death. In this context, if the effect of two compounds administered together in vitro (at a given concentration) is greater than the sum of the effects of each compound administered individually (at the same concentration), then the two compounds are considered to act synergistically. Such synergy is often achieved with cytotoxic agents able to act against cells in the Go-Go phase of the cell cycle.

Any period of pretreatment can be employed. For example, in therapeutic applications, such pretreatment can be for as little as about a day to as long as about 5 days or more; the pretreatment period can be between about 2 and about 4 days (e.g., about 3 days). Following pretreatment, a cytotoxic agent is administered. However, in other embodiments, a glucocorticoid (e.g., cortisol, dexamethasone, hydrocortisone, methylprednisolone, prednisolone, prednisone, etc.), diphenhydramine, rantidine, antiemetic-ondasteron, or ganistron can be adjunctively administered, and such agents can be administered with the pro-apoptotic modulator of Bcl-2 or related Bcl-2 family members. The cytotoxic agent can be administered either alone or in combination with continued administration of the pro-apoptotic modulator of Bcl-2 or related Bcl-2 family members following pretreatment. While, according to certain embodiments, treatment ceases upon administration of the cytotoxic agent, it can be administered continuously for a period of time (e.g., periodically over several days) as desired.

Any cytotoxic agent can be employed in the context of the invention, and as mentioned, many cytotoxic agents suitable for chemotherapy are known in the art. Such an agent can be, for example, any compound mediating cell death by any mechanism including, but not limited; to, inhibition of metabolism or DNA synthesis, interference with cytoskeletal organization, destabilization or chemical modification of DNA, apoptosis, etc. For example, the cytotoxic agent can be an antimetabolite (e.g., 5-fiourouricil (5-FU), methotrexate (MTX), fludarabine, etc.), an anti-microtubule agent (e.g., vincristine, vinblastine, taxanes (such as paclitaxel and docetaxel), etc.), an alkylating agent (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, camptothecins, etc.), or other cytotoxic agents (e.g., dexamethasone). The choice of cytotoxic agent depends upon the application of the inventive method. For research, any potential cytotoxic agent (even a novel cytotoxic agent) can be employed to study the effect of the toxin on cells or tumors pretreated with vitamin D (or a derivative). For therapeutic applications, the selection of a suitable cytotoxic agent will often depend upon parameters unique to a patient; however, selecting a regimen of cytotoxins for a given chemotherapeutic protocol is within the skill of the art.

For in vivo application, the appropriate dose of a given cytotoxic agent depends on the agent and its formulation, and it is well within the ordinary skill of the art to optimize dosage and formulation for a given patient. Thus, for example, such agents can be formulated for administration via oral, subcutaneous, parenteral, submucosal, intravenous, or other suitable routes using standard methods of formulation. For example, carboplatin can be administered at daily dosages calculated to achieve an AUC ("area under the curve") of from about 4 to about 15 (such as from about 5 to about 12), or even from about 6 to about 10. Typically, AUC is calculated using the Calvert formula, based on the glomerular filtration rate of creatinine (e.g., assessed by analyzing a plasma sample) (see, e.g., Martino et al. 1999 *Anticancer Res* 19:5587-91). Paclitaxel can be employed at concentrations ranging from about 50 mg/ml to about 100 mg/ml (e.g., about 80 mg/ml). Where dexamethasone is employed, it can be used in patients at doses ranging between about 1 mg to about 10 mg (e.g., from about 2 mg to about 8 mg), and more particularly from about 4 mg to about 6 mg, particularly where the patient is human. The dosage of the tyrosine kinase inhibitor is from 1 g/kg to 1 g/kg of body weight per day. According to one embodiment, the dosage of the tyrosine kinase inhibitor is from 0.01 mg/kg to 100 mg/kg of body weight per day. The optimal dosage of the tyrosine kinase inhibitor will vary, depending on factors such as type; and extent of progression of the cancer, the overall health status of the patient, the potency of the tyrosine kinase inhibitor, and route of administration. Optimization of the tyrosine kinase dosage is within ordinary skill in the art.

The pharmaceutical compositions disclosed herein can be most preferably used for prevention and treatment of malignancies selected from the group of hormone-refractory-prostate cancer; prostate cancer (Zin et al 2001 *Clin Cancer Res* 7:2475-9); breast cancer (Perez-Tenorio and Stal 2002 *Brit J Cancer* 86:540-45, Salh et al. 2002 *Int J Cancer* 98:148-54); ovarian cancer (Liu et al. 1998 *Cancer Res* 15:2973-7); colon cancer (Semba at al. 2002 *Clin Cancer Res* 8:1957-63); melanoma and skin cancer (Walderman, Wecker and Diechmann 2002 *Melanoma Res* 12:45-50); lung cancer (Zin et al. 2001 *Clin Cancer Res* 7:2475-9); and hepatocarcinoma (Fang et al. 2001 *Eur J Biochem* 268:45 1 3-9).

Additional specific types of cancers that can be treated using this invention include acute myelogenous leukemia, bladder, cervical, cholangiocarcinoma, chronic myelogenous leukemia, colorectal, gastric sarcoma, glioma, leukemia, lymphoma, multiple myeloma, osteosarcoma, pancreatic, stomach, or tumors at localized sites including inoperable tumors or in tumors where localized treatment of tumors would be beneficial, and solid tumors.

According to one preferred embodiment, the pro-apoptotic modulators of Bcl-2 can be administered in circumstances where the underlying cancer resists treatment with other chemotherapeutics or irradiation, due to the action of Bcl-2 blocking apoptosis.

Another embodiment of the invention provides a method of treating prostate cancer within a patient by administrating pro-apoptotic modulator of Bcl-2 or related Bcl-2 family members, and possibly a glucocorticoid, to the patient. Any pro-apoptotic modulator of Bcl-2 and glucocorticoid can be employed in accordance with this aspect of the invention, many of which are discussed elsewhere herein and others are generally known in the art. Moreover, pro-apoptotic modulator of Bcl-2 or related Bcl-2 family members and the glucocorticoid are delivered to the patient by any appropriate method, some of which are set forth herein. Thus, they can be formulated into suitable preparations and delivered subcutaneously, intravenously, orally, etc., as appropriate. Also, for example, the glucocorticoid is administered to the patient concurrently, prior to, or after the administration of the pro-apoptotic modulator of Bcl-2 or related Bcl-2 family members. One effective dosing schedule is to deliver between about 5 μg and about 25 g/kg, pro-apoptotic modulator of Bcl-2 or related Bcl-2 family members daily on alternative days (e.g., between 2 and 4 days a week, such as Mon-Wed-Fri or Tues-Thus-Sat, etc.), and also between about 1 mg/kg and 20 mg/kg dexamethasone to a human patient also on alternative days. In such a regimen, the alternative days on which pro-apoptotic modulator of Bcl-2 or related Bcl-2 family members and on which the glucocorticoid are administered can be different, although preferably they are administered on the same days. Even more preferably, the glucocorticoid is administered once, by itself, prior to concurrent treatment. Of course, the treatment can continue for any desirable length of time, and it can be repeated, as appropriate to achieve the desired end results. Such results can include the attenuation of the progression of the prostate cancer, shrinkage of such tumors, or, desirably, remission of all symptoms. However, any degree of effect is considered a successful application of this method. A convenient method of assessing the efficacy of the method is to note the change in the concentration of prostate-specific antigen (PSA) within a patient. Typically, such a response is gauged by measuring the PSA levels over a period of time of about 6 weeks.

Desirably, the method results in at least about a 50% decrease in PSA levels after 6 weeks of application, and more desirably at least about 80% reduction in PSA. Of course, the most desirable outcome is for the PSA levels to decrease to about normal levels.

Another embodiment of the invention provides a method of treating breast cancer within a patient by administrating the non-naturally occurring pro-apoptotic modulator of Bcl-2 or related Bcl-2 family members alone or in combination with any other treatment regimen for breast cancer. Treatments for breast cancer are well known in the art and continue to be developed. Treatments include but are not limited to surgery, including axillary dissection, sentinel lymph node biopsy, reconstructive surgery, surgery to relieve symptoms of advanced cancer, lumpectomy (also called breast conservation therapy), partial (segmental) mastectomy, simple or total mastectomy, modified radical mastectomy, and radical mastectomy; hormone therapy using a drug such as tamoxifen, which blocks the effects of estrogen; aromatase inhibitors, which stop the body from making estrogen; immunotherapy, e.g., using HERCEPTIN™ (trastuzumab), an anti-HER2 humanized monoclonal antibody developed to block the HER2 receptor; bone marrow transplantation; peripheral blood stem cell therapy; bisphosphonates; additional chemotherapy agents; radiation therapy; acupressure; and acupuncture. Particularly preferred chemotherapy agents for use in combination with the non-naturally-occurring compounds or peptides of the present invention include doxorubicin, paclitaxel, fluorouracil, cyclophosphamide, and tamoxifen. Any combination of therapies may be used in conjunction with the present invention.

In some embodiments, the pro-apoptotic modulators of Bcl-2 or related Bcl-2 family members can be used in the form of a pharmaceutically acceptable salt.

Suitable acids which are capable of forming salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

Pharmaceutically acceptable vehicles for delivery of the pro-apoptotic modulators of Bcl-2 or related Bcl-2 family members include physiologically tolerable or acceptable diluents, excipients, solvents, or adjuvants, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions can also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) can be used. The compositions can be prepared in conventional forms, either as liquid solutions or suspensions, solid forms suitable for solution or suspension in liquid prior to injection, or as emulsions.

Compositions containing the pro-apoptotic modulators of Bcl-2 or related Bcl-2 family members can be administered by any convenient route which will result in delivery of the conjugate to cells expressing the intracellular target. Modes of administration include, for example, orally, rectally, parenterally (intravenously, intramuscularly, intraarterially, or subcutaneously), intracistemally, intravaginally, intraperitoneally, locally (powders, ointments or drops), or as a buccal or nasal spray or aerosol.

The pharmaceutical compositions are most effectively administered parenterally, preferably intravenously or subcutaneously. For intravenous administration, they can be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small, other preferred routes of administration are intranasal, sublingual, and the like. Intravenous or subcutaneous administration can comprise, for example, injection or infusion.

The effective amount and method of administration of the pro-apoptotic modulators of Bcl-2 or related Bcl-2 family members will vary based upon the sex, age, weight and disease stage of the patient, whether the administration is therapeutic or prophylactic, and other factors apparent to those skilled in the art. Based upon the in vitro studies described herein, a suitable dosage is a dosage which will attain a tissue concentration of from about 1 to about 100 µM, more preferably from about 10 to about 75 µM. It is contemplated that lower or higher concentrations would also be effective. The tissue concentration can be derived from peptide conjugate blood levels. Such a dosage can comprise, for example, from about 0.1 to about 100 mg/kg.

Those skilled in the art will derive appropriate dosages and schedules of administration to suit the specific circumstances and needs of the patient. Doses are contemplated on the order of from about 1 to about 500, preferably from about 10 to about 100, most preferably from about 30 to about 80, mg/kg of body weight. The pro-apoptotic modulator of Bcl-2 or related Bcl-2 family members can be administered by injection daily, over a course of therapy lasting two to three weeks, for example. Alternatively, the agent can be administered by continuous infusion, such as via an implanted subcutaneous pumps, as is well-known in cancer therapy.

The pro-apoptotic modulators of Bcl-2 or related Bcl-2 family members according described herein can be labeled with a fluorescent, radiographic or other visually detectable label and utilized in in vitro studies to identify cells expressing an intracellular target, or to identify the location of the target inside of such cells. For example, a pro-apoptotic modulator of Bcl-2 or related Bcl-2 family members can be synthesized with an attached biotin molecule and incubated with cells suspected of expressing the target. The cells are then incubated with streptavidin-fluorescein. Cells expressing the intracellular target will bind the biotin conjugate, and the streptavidin-fluorescein complex. The result is a pattern of fluorescence inside the cell. In particular, a pro-apoptotic modulator of Bcl-2 or related Bcl-2 family members which binds the Bcl-2 protein or related Bcl-2 family members can be utilized to identify tumor cells which express Bcl-2 or related Bcl-2 family members. Assessment of Bcl-2 expression has prognostic value, as tumors expressing high levels of Bcl-2 or related Bcl-2 family members are likely to be chemoresistant and/or radiation resistant.

Selected compounds described herein are peptide-based substrate mimetic pro-apoptotic modulators of Bcl-2 that are stable in plasma for 6-24 hours, slowly metabolized by hepatic cells and are membrane permeable. The pro-apoptotic modulators of Bcl-2 induce apoptosis in cancer cells in the same concentrations that cell death is induced, while no cytotoxic death is observed at these concentrations by cell cycle analysis.

In addition, additional indications that can be treated using the pharmaceutical compositions described herein include any condition involving undesirable or uncontrolled cell proliferation Such indications include restenosis, benign tumors, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Specific types of restenotic lesions that can be treated include coronary, carotid, and cerebral lesions. Specific types of benign tumors that can be treated include hemangiomas, acoustic neuromas, neurofibroma, trachomas and pyogenic granulomas.

Treatment of cell proliferation due to insults to body tissue during surgery can be possible for a variety of surgical procedures, including joint surgery, bowel surgery, and keloid scarring. Diseases that produce fibrotic tissue include emphysema. Repetitive motion disorders that can be treated include carpal tunnel syndrome. An example of cell proliferative disorders that can be treated is a bone tumor.

Abnormal angiogenesis that can be treated include those abnormal angiogenesis accompanying rheumatoid arthritis, psoriasis, diabetic retinopathy, and other ocular angiogenic diseases such as retinopathy of prematurity (detrimental fibroplastic), macular degeneration, corneal graft rejection, neuromuscular glaucoma and Ouster Webber syndrome.

The proliferative responses associated with organ transplantation that can be treated include those proliferative responses contributing to potential organ rejections or associated complications. Specifically, these proliferative responses can occur during transplantation of the heart, lung, liver, kidney, and other body organs or organ systems.

IX. Assays for Detection of Apoptosis:

The compounds described herein can be tested in cells for induction of apoptosis of cancer cell lines. Apoptosis is assayed at least by two methods in each cell line. Cells are seeded at the appropriate plates for each method, treated with or without the inhibitory compounds for different time points and analyzed by one of the methods described below.

a. Annexin-V Staining

This assay identifies the early event of phosphatidyl-serine presentation on cell membrane. Cells are assayed for apoptosis using the Annexin-V.

Cells are seeded in 6-well plates ($0.3 \times 10^6$/well), and washed twice with PBS, 24 hrs after treatment with the inhibitory compounds, and resuspended in Annexin-V binding buffer (10 mM HEPES/NaOH pH 7.4, 140 mM NaCl and 2.5 mM $CaCl_2$). Annexin-V is diluted 1:40 and added to each sample with 0.2 nM Propidium Iodide (PI). $0.5 \times 10^6$ cells are taken per sample and analyzed by FACS.

b. Caspases Activity.

This assay indicates very early events of apoptosis. Caspases (1, 8, 9, 5, 7, 3, 6, 4, and 2) activity is assayed according to the manufacturer's instructions using the CaspaTag Caspase activity kit (Intergene), 24 hrs after treatment with the inhibitory compounds of the invention. Briefly, $10^6$ of suspended cells/sample are labeled with 10 µL of 30× working dilution FAM peptide-FMK-Fluorescein and incubated for 1 hr at 37° C. under 5%$CO_2$. Samples are washed 3 times with 1× working dilution wash buffer and the cell pellets are resuspended with 700 µl of the same buffer. 2 µl of 0.2 nM propidium iodide solution is added and caspases activity is determined by FACS analysis.

c. DNA fragmentation Measurement.

DNA fragmentation is a late event in the apoptosis cascade. DNA fragmentation is measured according to the manufacturer's instructions using the In situ cell death detection kit (Roche), 72 hrs after treatment with the compounds of the invention. Briefly, $2 \times 10^6$ of adherent cells/sample are trypsinized, washed twice with PBS, and replated in 96 well plates. Then, the samples are fixed with 2% paraformaldehyde in PBS at room temperature for 1 hr, washed with PBS and resuspended with permeabilization solution for 2 min on ice. Cells are washed twice with PBS, and labeled with TUNEL reaction mixture containing labeling solution and TdT enzyme solution for 1 hr at 37° C. Samples are washed again with PBS and analyzed by FACS.

X. Growth Inhibition Assays:

Selected compounds, which were found active in the enzyme-inhibition assays are screened for their ability to inhibit growth of tumor cell lines. Screening for inhibitory compounds is done, initially, at concentration of 50 µM.

Active compounds from the first screening are further tested at different concentrations (50, 25, 12.5, 6.25, 3.125 and 1.56 μM) in order to determine their $IC_{50}$. Growth inhibition is tested using two methods: A. staining of viable cells with methylene blue, B. incorporation of $^3$H-thymidine. For both methods cells are grown in 96-well plates for 24 hours, before tested compounds are added. The assays are done in triplicate for one to six days.

a. Staining Viable Cells with Methylene Blue

Cells are fixed by 0.5% glutardialdehyde followed by staining with 1% methylene blue in borate buffer (Sigma) for one hour. Cells are then washed a few times with distilled water, air dried and the color is extracted by adding 0.1 M HCl for one hour at 37° C. Quantitation of color intensity is performed by measurement of the optical density at 600 nm by ELISA reader.

b. Incorporation of 3H-thymidine:

At the appropriate time in culture loci of $^3$H-thymidine (stock of 5 Ci/mmole, Amersham) is added to each well containing 100 μl of medium for 5 hours. At the end of the incubation the cells are washed a few times with PBS using a cell harvester (Packard, USA), air dried for a few hours and 50 μl of scintillation liquid is added. The radioactivity is counted using a microplate counter, for example, Packard Top Count.

Fifty percent inhibitory concentration ($IC_{50}$) values are calculated using nonlinear regression in one site competition model with GraphPad Prism version 3.03 Windows (Graph-Pad Software, San Diego, USA)

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art.

Accordingly, it is intended to embrace all such modifications and variations that fall within the spirit and broad scope of the appended claims.

EXAMPLES

Example 1

The following examples describe the processes used to identify and characterize peptides that target Bcl-2-family members and regulate their apoptotic functions.

Figure 5:
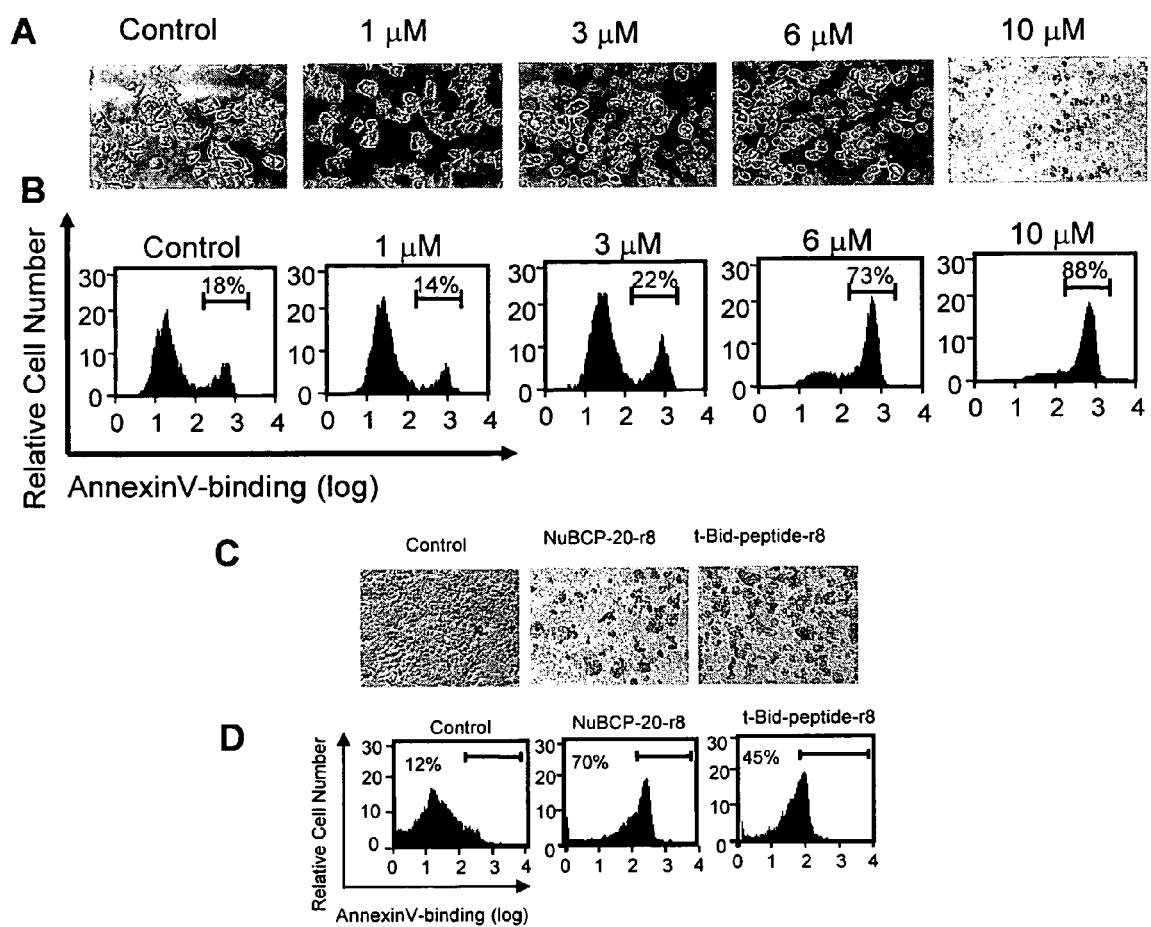
FIG. 5A is a series of photographs showing inhibitory effect of various concentrations of Nur77-peptide on cell growth.
FIG. 5B is a series of graphs showing apoptotic effect of various concentrations of Nur77-peptide.
FIG. 5C is a series of photographs showing a comparison of growth inhibitory effects of NuBCP peptide and t-Bid peptide.
FIG. 5D is a series of graphs showing a comparison of apoptotic effects of NuBCP-20-r8-peptide and t-Bid peptide.

Peptides from DC3 fragment of Nur77, known to interact with Bcl-2, were synthesized and conjugated with the cell-penetrating-peptide (CPP), D-Arg octamer (r8) (FIG. 1A) as described below. Amongst these, a peptide with 20 amino acids (480 to 499) (NuBCP-20-r8) exhibited potent apoptotic effects in various cancer cell lines. In ZR-75-1 breast cancer cells, significant apoptosis (>80%) was observed by <10 μM NuBCP-20, whereas normal primary mammary epithelial cells were resistant (FIGS. 1B, C, FIG. 5A, B).

To identify the minimal-length of NuBCP required for inducing apoptosis, NuBCP-20 was subjected to serial deletion analysis (FIG. 1D) as described below. A Nur77 peptide with only 9 amino acids, NuBCP-9-r8, was found to potently induce apoptosis. NuBCP-9 is considerably shorter than the shortest BH3 peptide that binds Bcl-2. Further deletion from either its N-terminal or C-terminal end or substituting Ala for NuBCP-9 terminal amino acids (NuBCP-9/AA-r8) completely abolished its apoptotic effect. NuBCP-9 linked to other CPPs, penetratin or transportan-10 (Jones, S. W. et al. 2005 Br J Pharmacol 145:1093-102) as well as r8 by a disulfide bond showed a similar degree of apoptosis (FIG. 1E). Since disulfide bonds are rapidly reduced in cells, the apoptotic effect of NuBCP-9 was not due to the conjugated CPPs. The NuBCP-20-r8 was more potent than BH3 peptides derived from pro-apoptotic Bcl-2 family member t-Bid (FIGS. 1F, 5C, D).

To probe the stereochemical requirements for NuBCP-induced apoptosis, the L-amino acids were substituted with D-amino acids. When H460 lung cancer cells were exposed to the D-analog of NuBCP-9 (D-NuBCP-9-r8), apoptosis was retained and even slightly enhanced compared with NuBCP-9-r8 (FIG. 1F). In contrast, the D-enantiomer of Bad-BH3 peptide did not bind Bcl-2 and was not apoptotic (FIG. 1F), demonstrating a clear difference in the mode of action of the NuBCP and Bad-BH3 peptide.

Figure 2:
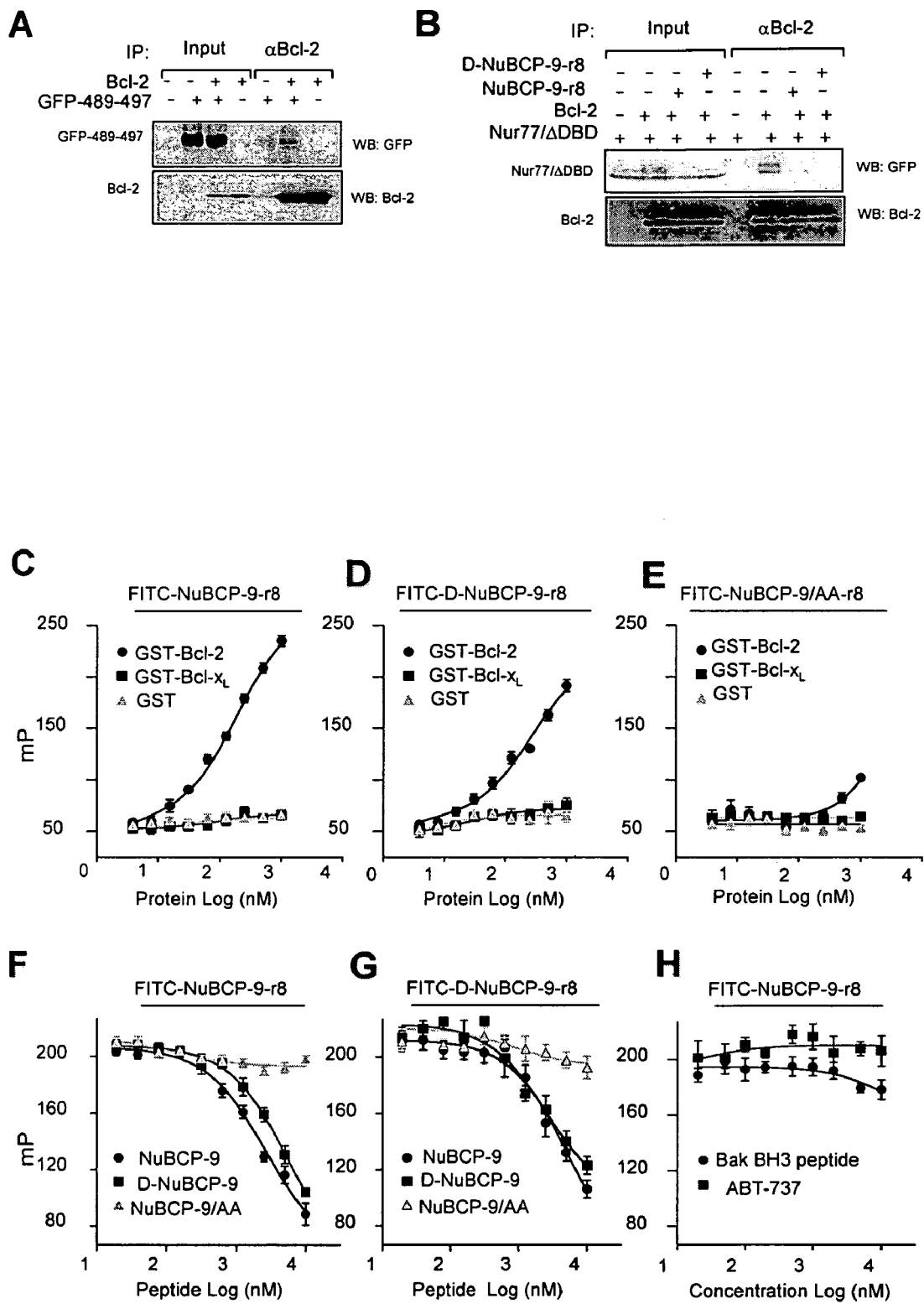
FIG. 2A is a photograph of a gel showing that GFP-Nur77/489-497 (GFP-NuBCP-9) is precipitated by anti-Bcl-2 antibody only when Bcl-2 was coexpressed.
FIG. 2B is a photograph of gel showing that Nur77 lacking its DNA-binding domain (DBD), Nur77/ΔDBD bound strongly with Bcl-2 and the binding was abrogated in the presence of NuBCP-9-r8 or D-NuBCP-9-r8. The bars represent means±SD from 3-4 experiments.
FIGS. 2C-2E are graphs showing fluorescence polarization (FP) assay of NuBCPs binding to Bcl-2.
FIG. 2F-H are graphs showing FP competition assay.
Figure 6:
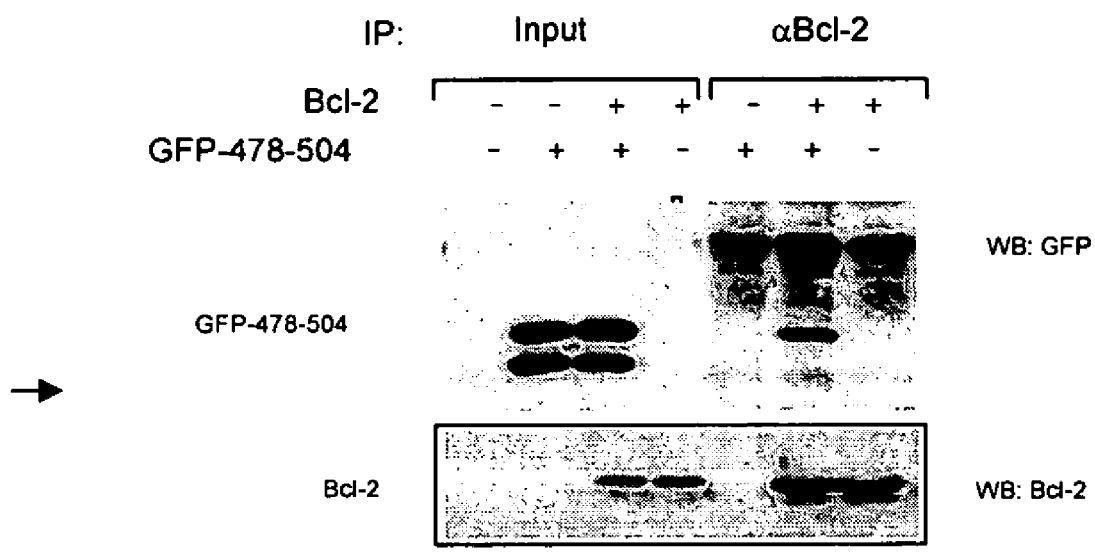
FIG. 6 is a photograph of an immunoprecipitation gel showing binding of NuBCP-20-r8-peptide with Bcl-2.
Figure 7:
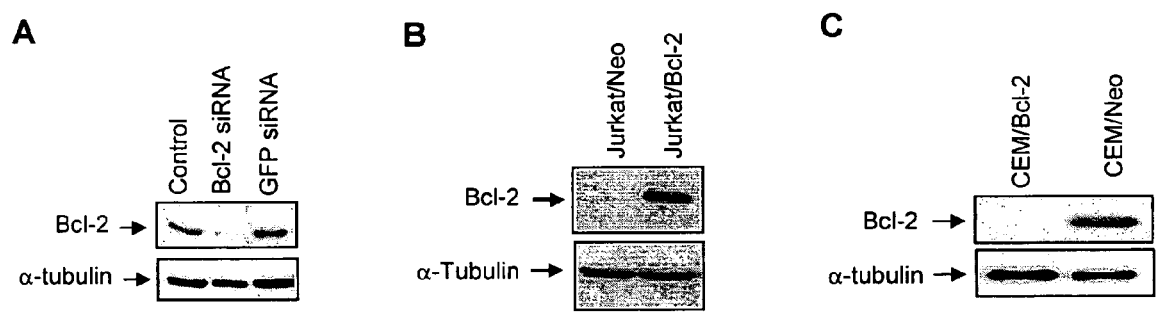
FIG. 7A is a photograph of an immunoblot gel showing inhibition of Bcl-2 expression by Bcl-2 siRNA.
FIG. 7B is photograph of a gel showing stable expression of Bcl-2 in Jurkat/Neo and Jurkat cells stably expressing Bcl-2.
FIG. 7C is a photograph of a gel showing expression of Bcl-2 in CEM and CEM cells stably expressing Bcl-2.

To determine whether NuBCPs bound to Bcl-2, DNA sequences encompassing NuBCP-9 (Nur77/489-497) were cloned into a vector containing the green fluorescence protein (GFP). Like NuBCPs, the GFP-Nur77/489-497 fusion was apoptotic. When transfected into HEK293T cells, it was precipitated by anti-Bcl-2 antibody only when Bcl-2 was co-expressed (FIG. 2A), which was inhibited by addition of NuBCP, but not Smac-peptide-r8. To study whether D-NuBCP-9 interacted with Bcl-2, a competition assay was used as described below. Nur77 lacking its DNA-binding-domain (DBD), Nur77/ΔDBD, bound strongly with Bcl-2, and the binding was abrogated when NuBCP-9-r8 or D-NuBCP-9-r8 was present (FIG. 2B). The GFP-Nur77/489-497 fusion colocalized extensively with RFP-Mito, a red fluorescence protein (RFP) fused with a classical mitochondria-targeting sequence. FITC-D-NuBCP-9-r8 also displayed extensive colocalization with RFP-Mito. Similar results were obtained with NuBCP-20 (FIG. 6). Thus, NuBCP-9 and its D-enantiomer, similar to Nur77, bind Bcl-2 and target mitochondria, which is a repository for Bcl-2 where apoptosis is triggered.

Fluorescence polarization (FP) analysis was used to determine whether NuBCPs interacted directly with Bcl-2. Nur77 did not bind Bcl-$X_L$ and served as a control. GST-Bcl-2, but not GST-Bcl-$X_L$ or GST, induced a concentration-dependent FP of FITC-NuBCP-9-r8 and FITC-D-NuBCP-9-r8, while FITC-NuBCP-9/AA-r8 was little affected (FIG. 2C-E). In addition, unconjugated NuBCP-9 and D-NuBCP-9 competed for binding of FITC-L-NuBCP-9-r8 or FITC-D-NuBCP-9-r8, whereas NuBCP-9/AA did not (FIG. 2F-H). Thus, NuBCP-9 and D-NuBCP-9 bind directly and competitively to Bcl-2. The site on Bcl-2 targeted by NuBCPs is distinct from BH3 peptides, as shown by the failure of either a BH3 peptide or a highly potent chemical inhibiter (ABT-737) that targets the BH3-binding site to reduce FITC-NuBCP-9-r8 binding (FIG. 2F-H).

Figure 3:
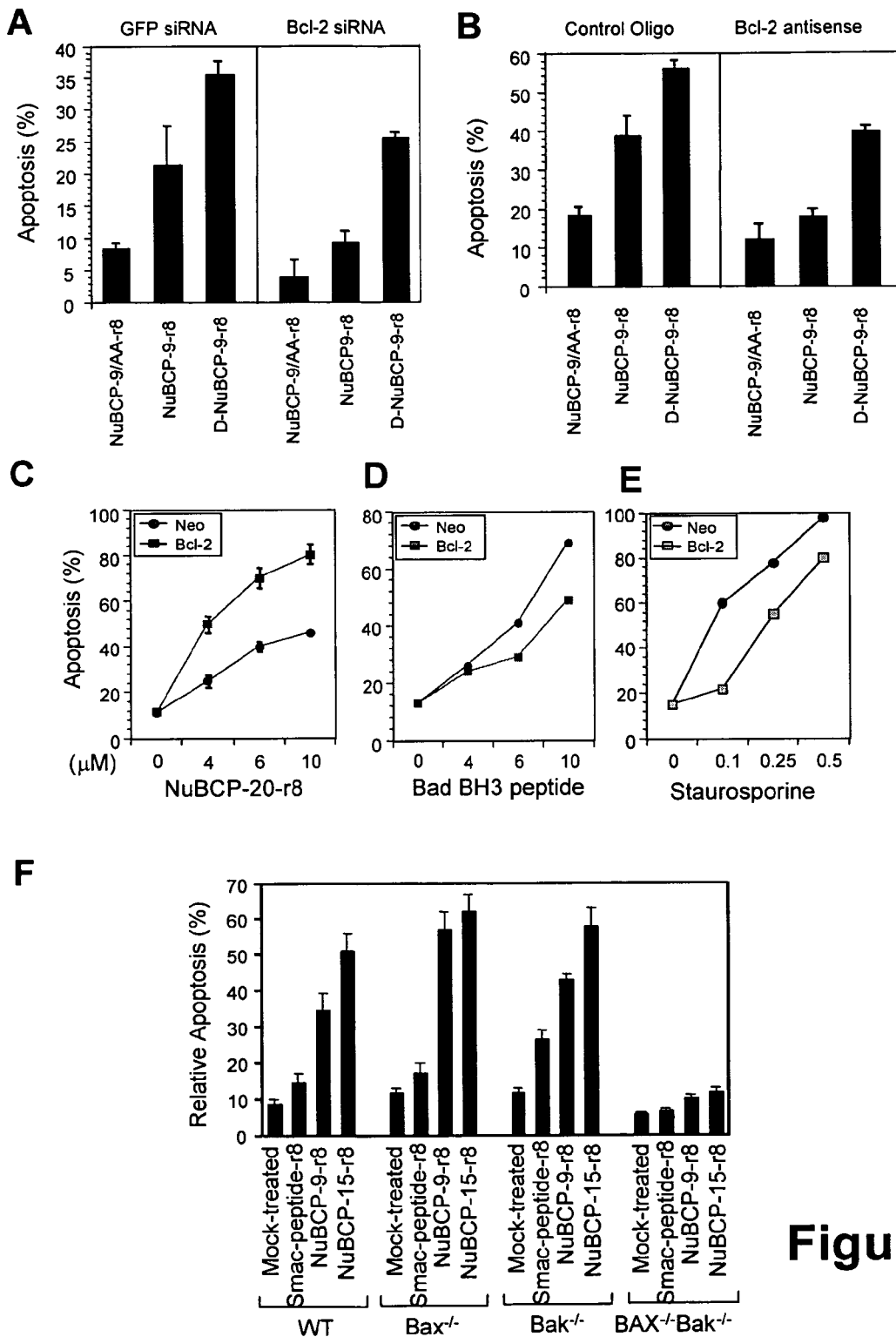
FIG. 3A is a bar graph showing that Bcl-2 siRNA suppressed apoptosis induced by Nur77 peptides.
FIG. 3B is a bar graph showing that Bcl-2 antisense oligonucleotides suppressed apoptosis induced by Nur77 peptides.
FIGS. 3C-E are graphs showing that stable expression of Bcl-2 enhances apoptosis by NuBCP. The bars represent means±SD from 3-4 experiments
FIG. 3F is a bar graph showing that Bax and Bak are required for apoptotic effect of NuBCP. The bars represent means±SD from 3-4 experiments.

A hallmark of Nur77 is its induction of apoptosis in a Bcl-2-dependent manner. Therefore experiments were performed to examine whether NuBCP-9-induced apoptosis was dependent on Bcl-2. Transfection of Bcl-2 siRNA, but not control GFP siRNA, reduced Bcl-2 levels (FIG. 7A) and inhibited the apoptotic effects of NuBCP-9-r8 and D-NuBCP-9-r8 in H460 lung cancer cells (FIG. 3A). Exposure of cells to Bcl-2 antisense oligonucleotides also attenuated their apoptotic function (FIG. 3B). In contrast, stable expression of Bcl-2 in Jurkat or CEM cells strongly enhanced NuBCP-induced cell death (FIGS. 3C-E, 7A-C, 8A-D). For comparison, apoptosis induced by Bad BH3 peptide or staurosporine was attenuated by overexpression of Bcl-2 in these cells, demonstrating the dual role of Bcl-2. The NuBCP-induced apoptosis requires Bax or Bak, as the peptides similarly induced apoptosis of wild-type, Bax$^{-/-}$, and Bak$^{-/-}$ mouse embryonic fibroblasts (MEFs), but lacked death activity in double knockout MEFs (FIG. 3F).

Nur77 binding to Bcl-2 resulted in exposure of the Bcl-2 BH3 domain, a characteristic of Bcl-2 pro-apoptotic state. Such a Bcl-2 conformation is recognized by an anti-Bcl-2 antibody raised against the Bcl-2 BH3 domain. To determine whether NuBCP-9 induced a Bcl-2 conformational change, flow cytometric assays were conducted which HEK293T cells transfected with Bcl-2 were exposed to NuBCPs and subsequently stained with the anti-Bcl-2/BH3 antibody. Fluorescence microscopy showed that the antibody failed to stain Bcl-2 in control cells, reflecting the anti-apoptotic conformation of Bcl-2, in which its BH3 domain epitope is buried. By contrast, cells exposed to NuBCP-9-r8 or D-NuBCP-9-r8 were strongly stained. Thus, both peptides were able to induce a pro-apoptotic Bcl-2 conformation. Consistent with its inability to induce apoptosis, NuBCP-9/AA-r8 failed to induce Bcl-2 immunostaining.

Figure 4:
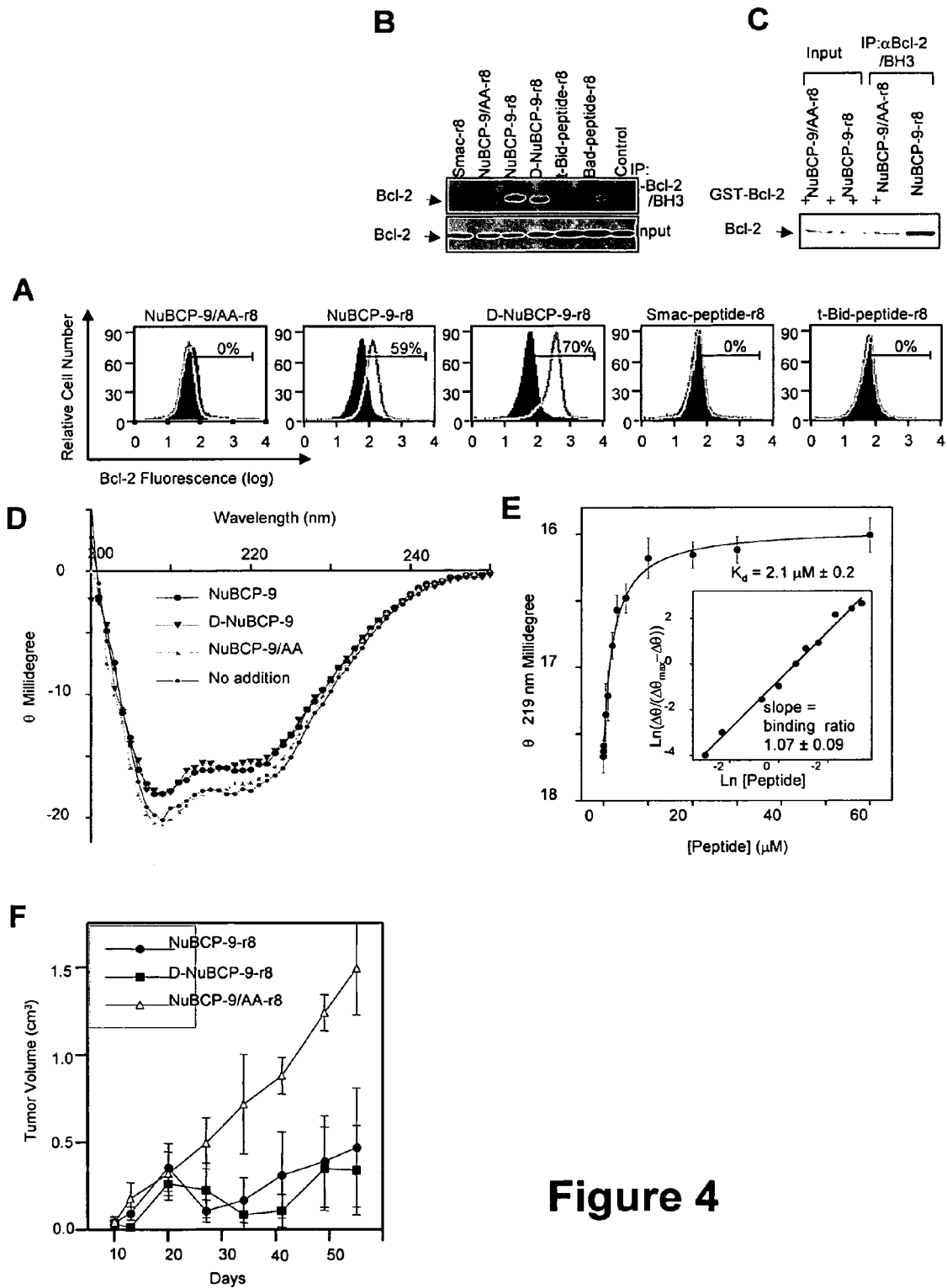
FIG. 4A is a series of graphs showing that NuBCPs induce Bcl-2 conformational change in vitro. Bcl-2 fluorescence from peptide-treated cells (white histogram) was compared to that from the non-treated cells (shaded histogram). Numbers represent % of treated cells showing increased Bcl-2 immunofluorescence compared to the auto-fluorescence of the non-treated cells from the same experiment.
FIG. 4B is a photograph of a gel showing that the anti-Bcl-2/BH3 antibody precipitated endogenous Bcl-2 in cells treated with L-NuBCP-9-r8 or D-NuBCP-9-r8.
FIG. 4C is a photograph of a gel showing that incubation with NuBCP-9-r8 resulted in a strong precipitation of GST-Bcl-2 protein by the anti-Bcl-2/BH3 antibody.
FIG. 4D is a graph showing circular dichroism (CD) spectra for the binding of the NuBCP peptides (30 μM) to GST-Bcl-2 (2 μM).
FIG. 4E is a non-linear regression analysis of the CD spectra showing the binding of NuBCP-9 with Bcl-2 is saturating and stoichiometric with a Kd=2.1±0.2 μM.
FIG. 4F is a graph showing Inhibition of tumor growth by NuBCPs.
Figure 8:
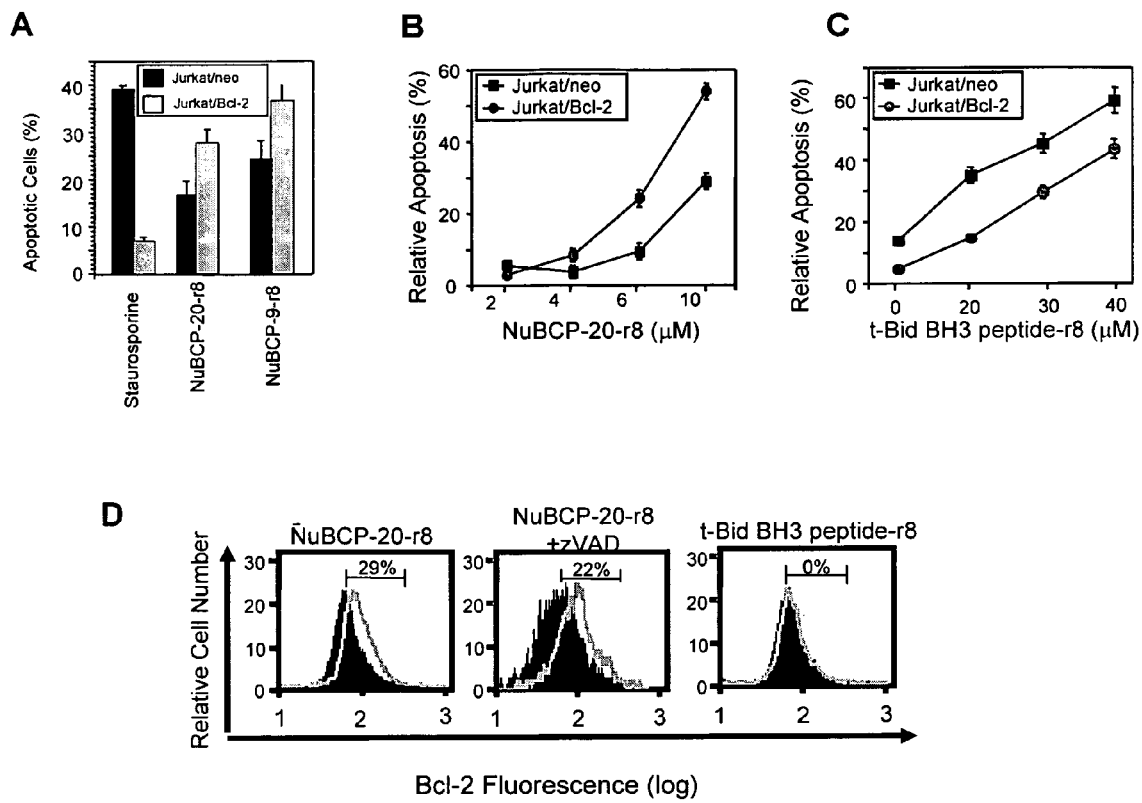
FIG. 8A is a bar graph showing that Bcl-2 potentiates the apoptotic effect of NuBCP in Jurkat cells.
FIGS. 8B and C are graphs showing that NuBCP-20-r8 and t-Bid BH3-r8 peptides induce apoptosis in Jurkat cells.
FIG. 8D is a series of graphs showing that various NuBCP peptides induce Bcl-2 conformational change which is not the consequence of apoptosis. Bcl-2 fluorescence from peptide-treated cells (light histogram) was compared to that from the non-treated cells (shaded histogram). Numbers represent % of treated cells showing Bcl-2 immunofluorescence compared to the auto-fluorescence of the non-treated cells from the same experiment.

Flow cytometry analysis also revealed a strong Bcl-2 immunofluorescence in cells exposed to L-NuBCP-9-r8 or D-NuBCP-9-r8, but not NuBCP-9/AA-r8, when stained by the anti-Bcl-2/BH3 antibody (FIG. 4A). In contrast, cells exposed to apoptosis-inducing t-Bid-BH3 peptide or Smac-peptide-r8 did not show any Bcl-2 immunofluorescence. NuBCP-9-r8-induced Bcl-2 immunofluorescence was observed in the presence of the caspase inhibitor zVAD, excluding the involvement of caspases in the Bcl-2 conformational change (FIG. 8D). The effect of NuBCPs on Bcl-2 conformation was further examined by immunoprecipitation assays (FIG. 4B), showing that the anti-Bcl-2/BH3 antibody precipitated endogenous Bcl-2 in cells treated with L-NuBCP-9-r8 or D-NuBCP-9-r8, but not NuBCP-9/AA-r8, t-Bid-BH3-peptide-r8, or Bad-BH3-peptide-r8.

Figure 9:
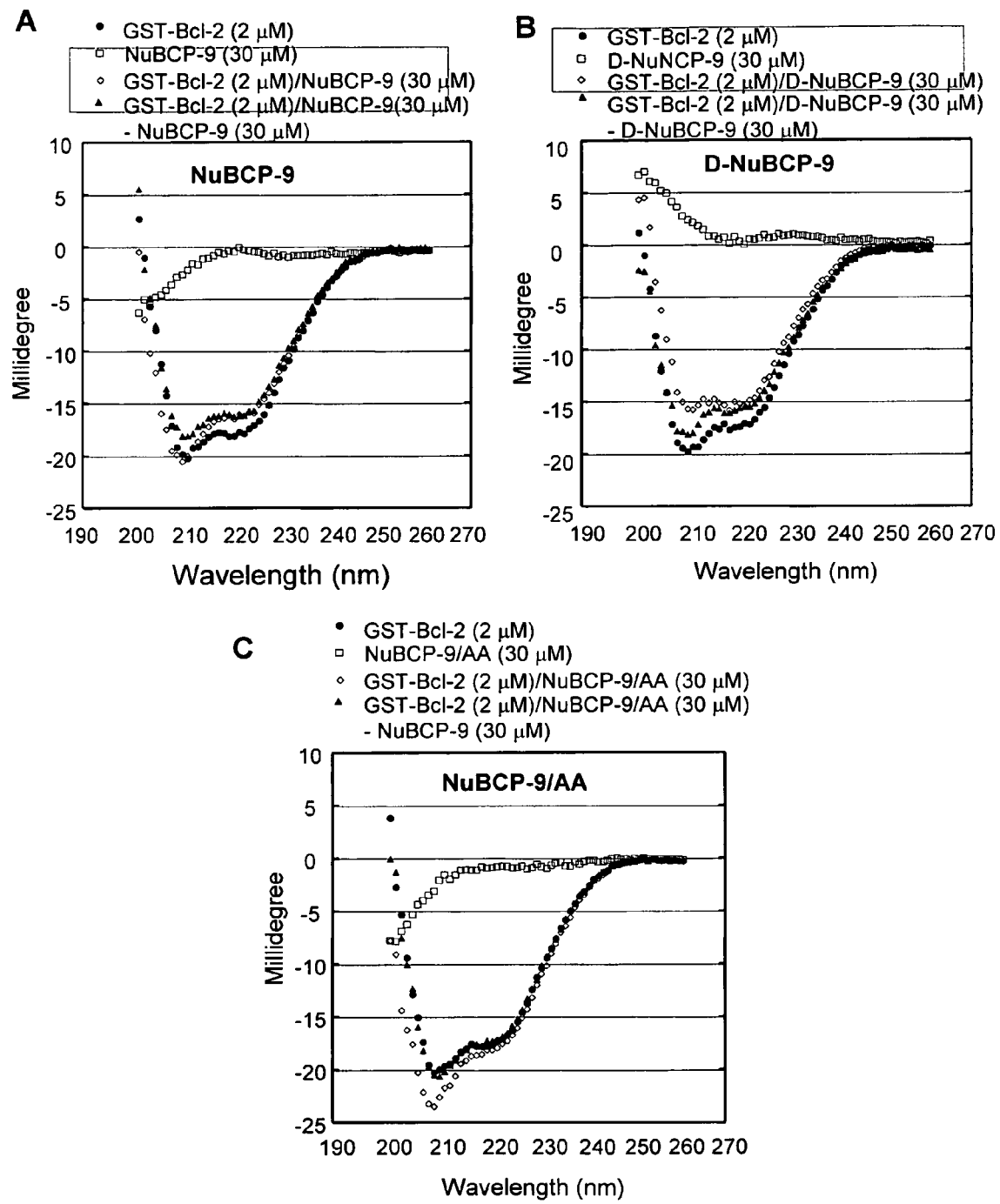
FIGS. 9A-C are graphs showing CD spectra for binding NuBCPs to GST-Bcl-2.
Figure 10:
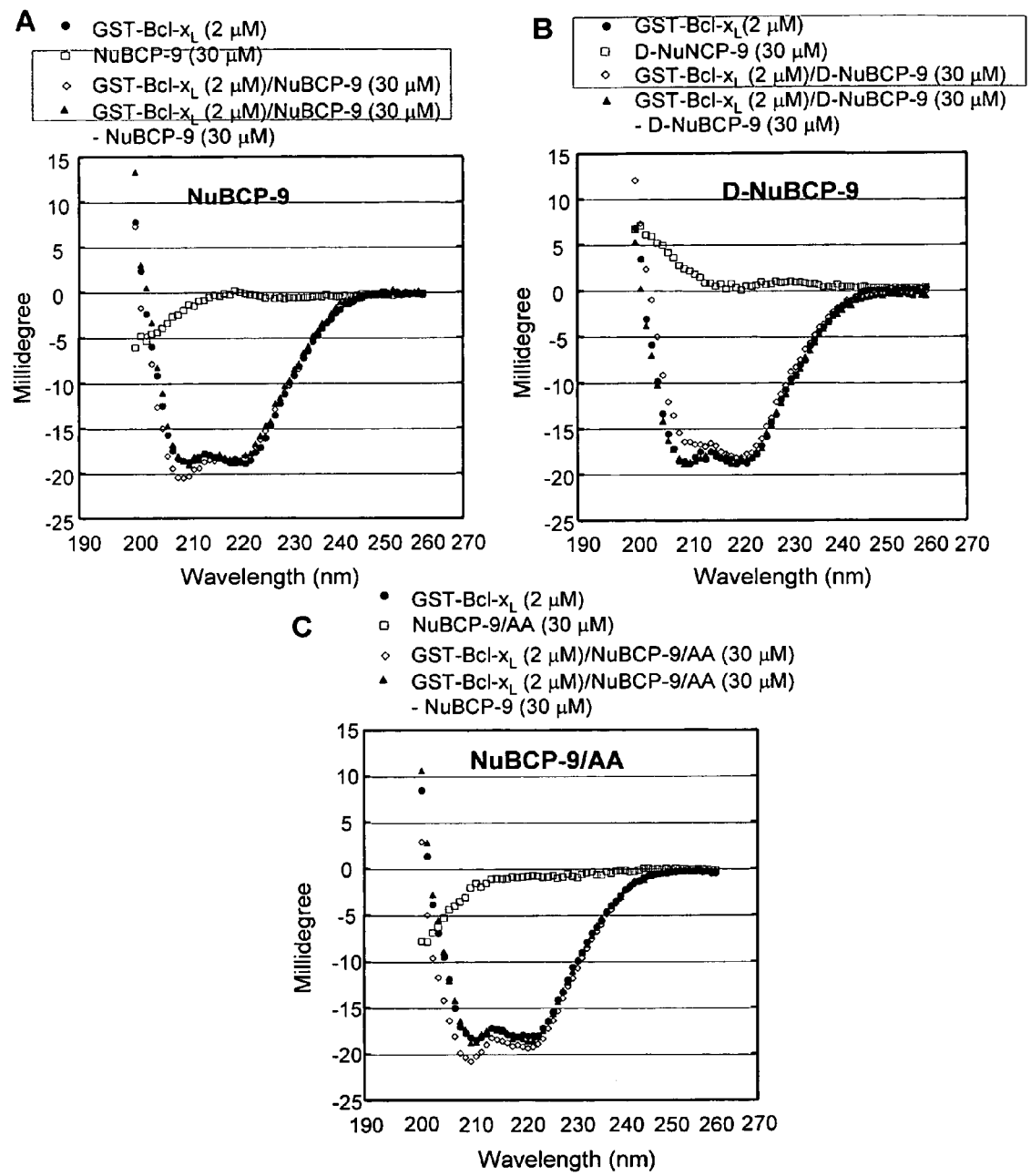
FIG. 10A-C are graphs showing CD spectra for binding NuBCPs to GST-Bcl-xL.
Figure 11:
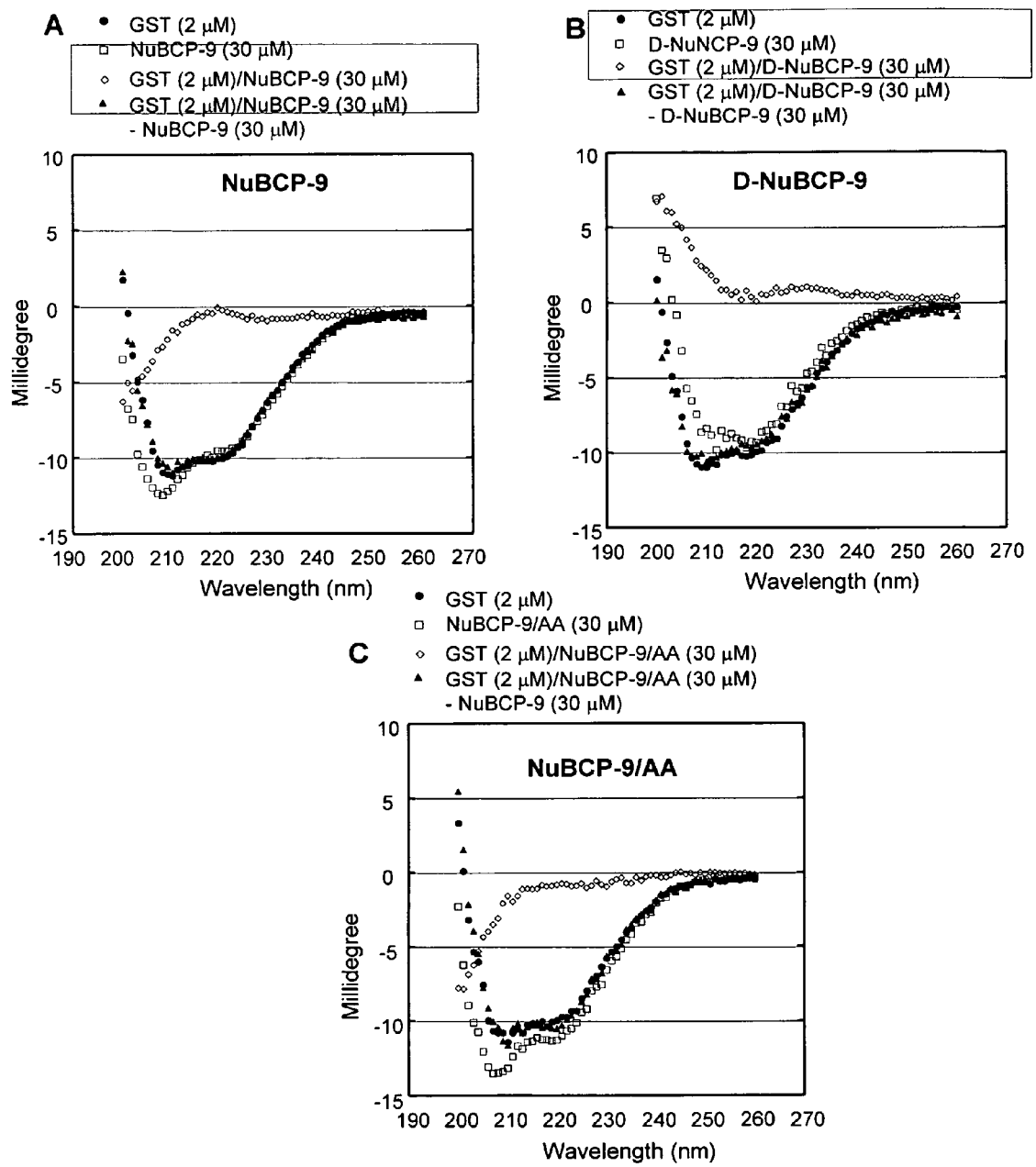
FIG. 11A-C are graphs showing CD spectra for binding NuBCPs to GST.

We then explored whether the Bcl-2 conformational change by Bcl-2 was a direct consequence of Nur77 binding. Experiments were performed to determine whether NuBCPs could induce a conformational change of bacterially expressed Bcl-2. To this end, the ability of purified GST-Bcl-2 protein to react with anti-Bcl-2/BH3 antibody in the presence of NuBCP was analyzed by immunoprecipitation assay. Incubation with NuBCP-9-r8 but not NuBCP-9/AA-r8, resulted in a strong precipitation of GST-Bcl-2 protein by the anti-Bcl-2/BH3 antibody (FIG. 4C), demonstrating a direct role of NuBCP binding in Bcl-2 conformational change. This was further supported by circular dichroism (CD) analysis, revealing similar changes in GST-Bcl-2 protein spectra, when incubated with NuBCP-9 or D-NuBCP-9, but not NuBCP-9/AA (FIG. 4D). Binding was saturating and stoichiometric with a Kd=2.1±0.2 µM (FIG. 4E), in agreement with FP assays. In contrast, NuBCP-9, D-NuBCP-9 and NuBCP-9/AA had no effect on CD spectra for GST or Bcl-$X_L$ (FIGS. 9-11). Thus, the NuBCP-induced Bcl-2 conformational change observed in cells can be accounted for by direct binding of NuBCPs to Bcl-2.

The competitive FPA assays described above demonstrates how the FITC-NuBCP-9-r8 peptide can be used to identify NuBCP peptide analogs that compete with NuBCP-9-r8 for binding to Bcl-2 or Bcl-2 related proteins. This same assay can also be used to identify peptidomimetics and small molecule mimics or antagonists of Nur77 or functionally related proteins such as Nor1 or Not (also Nurr1). Mimics can be distinguished from antagonists using CD analysis described above to detect the presence or absence of a conformational change. Nur77 mimics would induce a conformational change in Bcl-2 similar to that observed for NuBCP-9 while antagonists would not compete with NuBCP-9-r8 for binding to Bcl-2 but not induce a conformational change. Mimics would identify compounds that could act as pro-apoptic compounds whereas antagonists could block the pro-apoptotic effects of Nur77 or functionally equivalent proteins such as Nor1 and Not. Compounds that mimic Nur77 could be used for treating cancers characterized by elevated levels of Bcl-2 while compounds that antagonize Nur77 or functionally related proteins could be used to treat neurodegenerative diseases that are characterized by converting Bcl-2 to its pro-apoptotic form.

Figure 12:
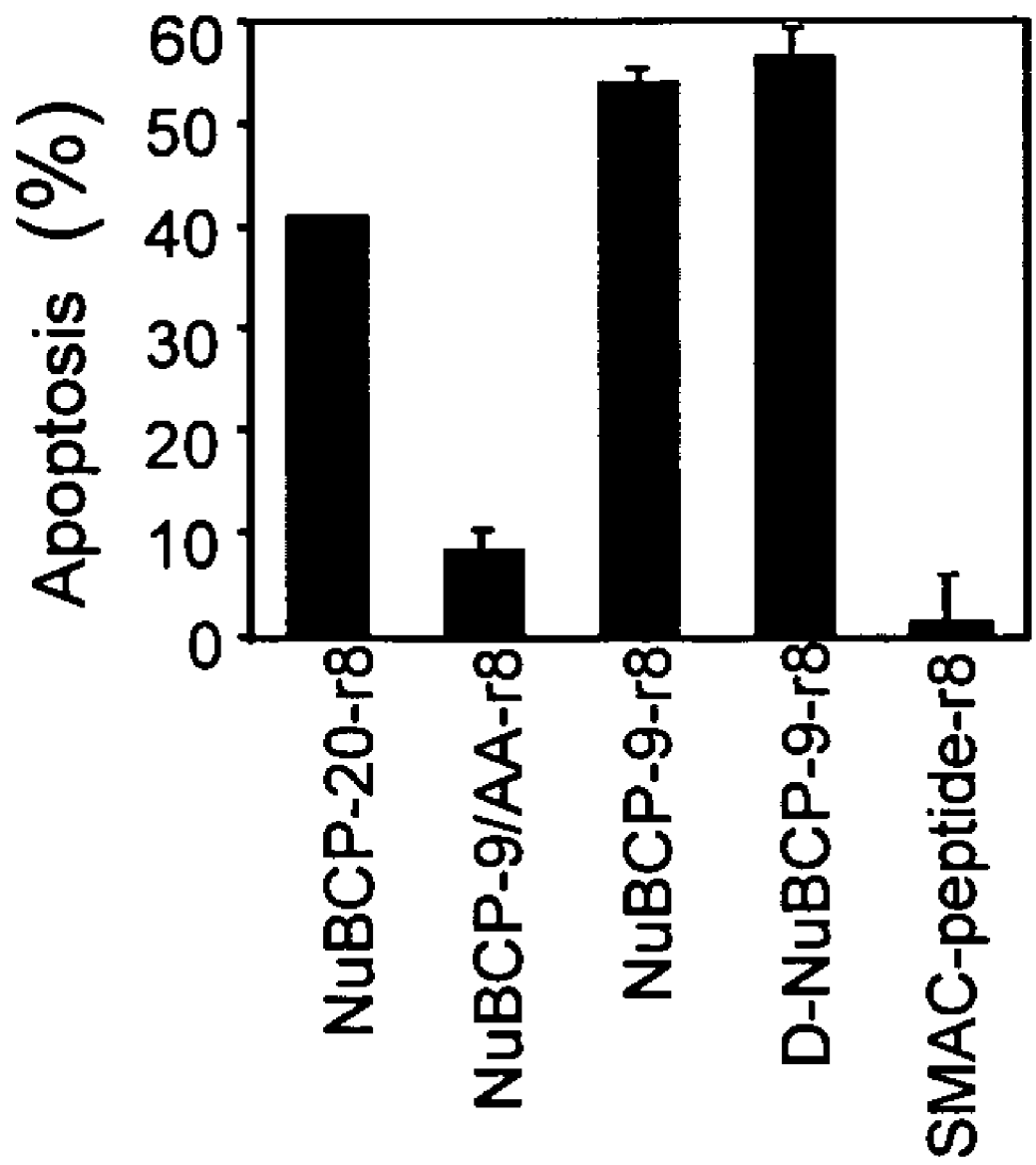
FIG. 12 is a bar graph showing induction of apoptosis of MDA-MB435 breast cancer cells in vitro by NuBCP peptides.

To further evaluate NuBCPs, their effects on the growth of tumors formed in SCID mice were examined by methods described below. MDA-MB435 breast cancer cells, which are sensitive to NuBCPs (FIG. 12) and rapidly form tumors in SCID mice, were used. Comparison with control (NuBCP-9/AA-r8) peptide showed that the injection of either L-NuBCP-9-r8 or D-NuBCP-9-r8 dramatically suppressed the growth of tumors (FIG. 4F), and potently induced apoptosis of tumor cells in vivo. Apoptosis of tumor cells was associated with a Bcl-2 conformational change, as revealed by extensive overlapping of TUNEL staining with Bcl-2 immunofluorescence stained by anti-Bcl-2/BH3 antibody. Together, these results demonstrate that NuBCPs effectively inhibit tumor growth in mice through apoptosis induction by inducing a Bcl-2 conformational change.

Figure 13:
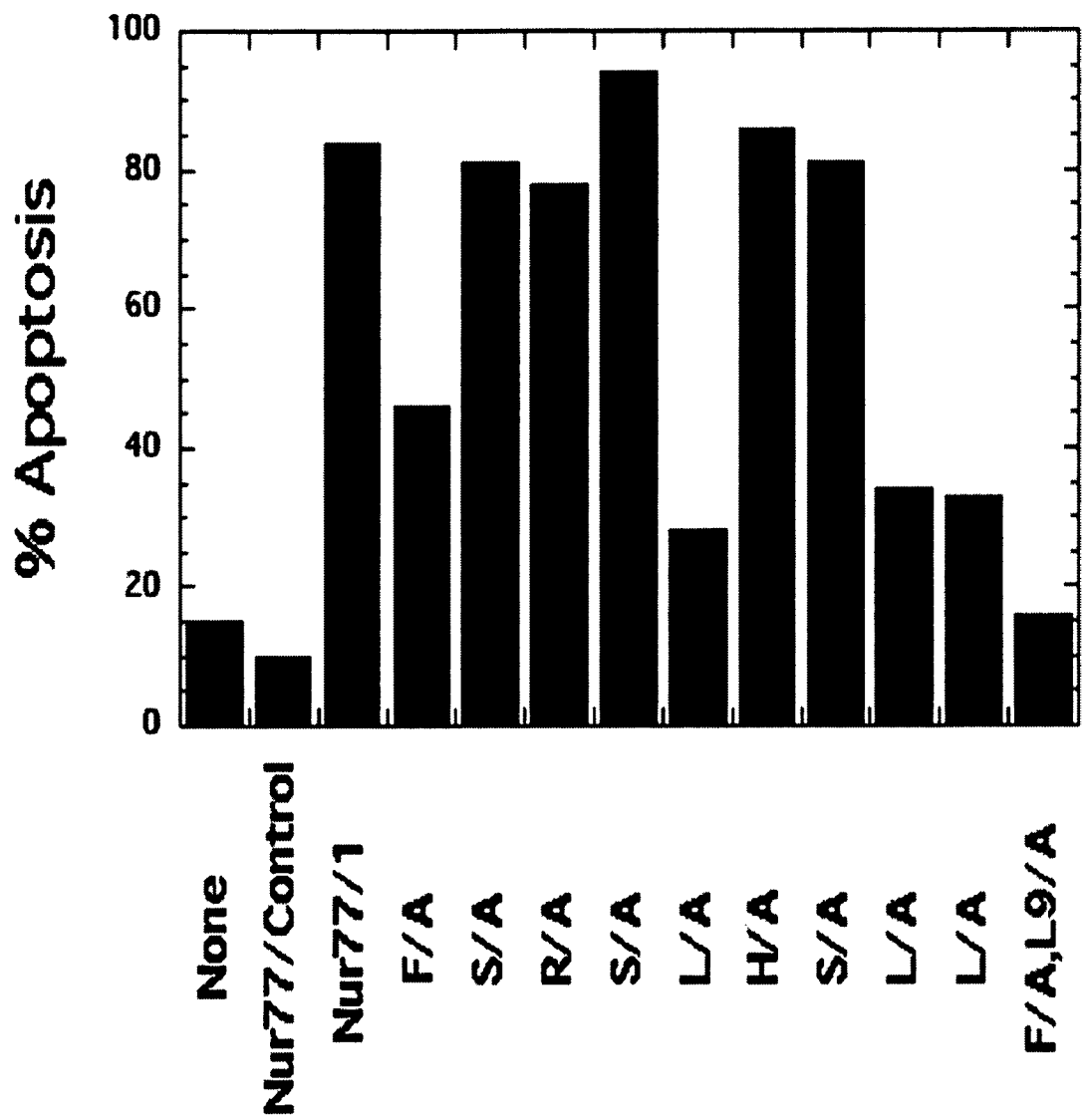
FIG. 13 is a bar graph showing that replacement of Phe489, Leu493, Leu497 and Leu498 amino acids in NuBCP-9-r8 peptide with alanine largely impaired, while simultaneous substitutions of Phe489 and Leu497 completely abolished, the apoptotic effect of NuBCP-9-r8.

Alanine scan of Nur77/1 peptide using H460 lung cancer cells. To characterize amino acid residues in the Nur77-9 peptide critical for its activity, each amino acid was substituted with alanine as follows: acetyl-ASRSLHSLLGXmmrrrr-amide (SEQ ID NO: 61); acetyl-FSRSAHSLLGXrrrrrrrr-amide (SEQ ID NO: 62); acetyl-FSRSLHSALGXrrrrrrrr-amide (SEQ ID NO: 63); acetyl-FSRSLHSLAGXrrrrrrrr-amide (SEQ ID NO: 64). Analysis of these mutant Nur77-9 peptides showed that Phe489, Leu493, Leu497 and Leu498 were critical. Replacement of these amino acids with alanine largely impaired, while simultaneous substitutions of Phe489 and Leu497 completely abolished, the apoptotic effect of Nur77-9 (FIG. 13).

Figure 14:
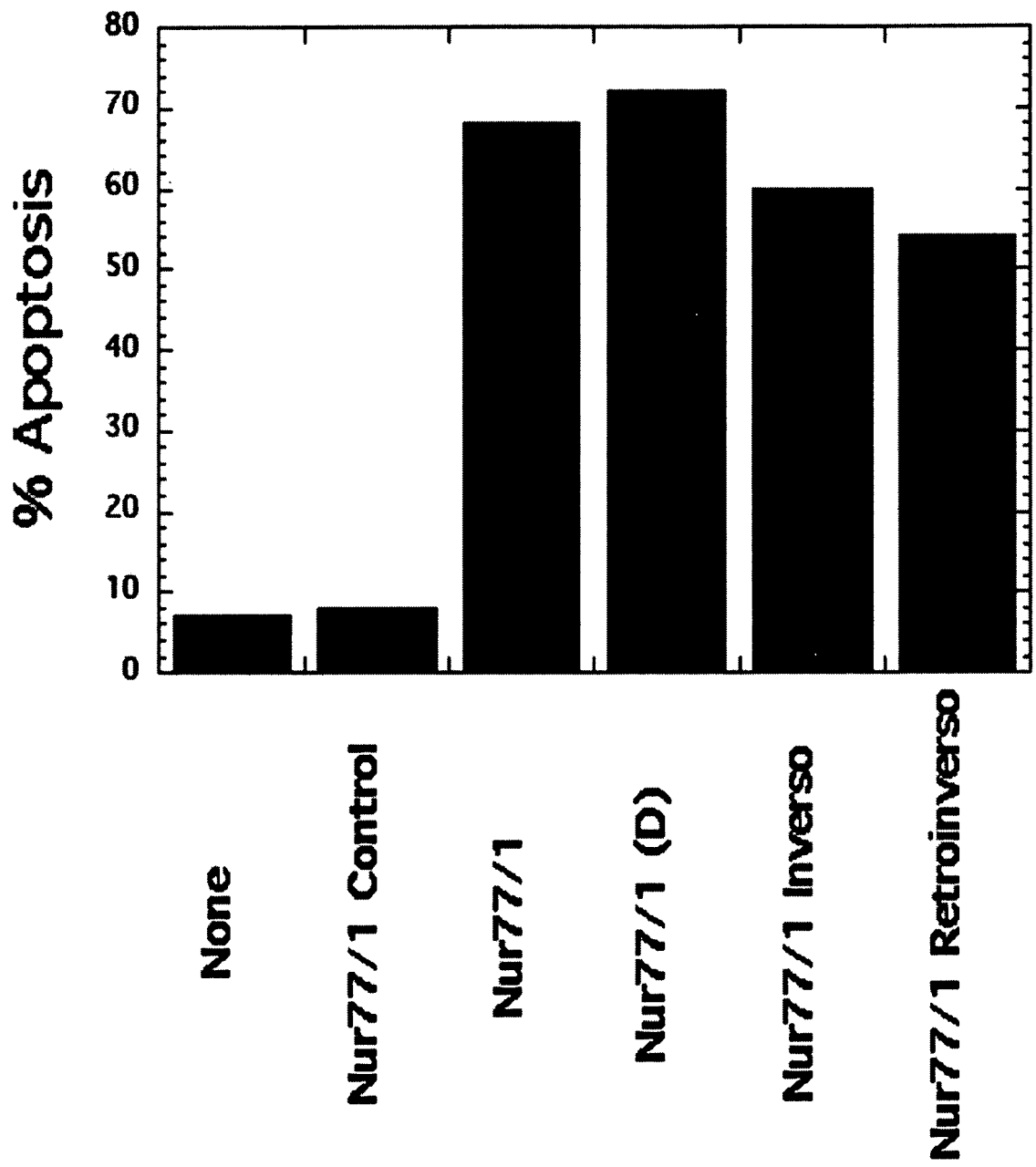
FIG. 14 is a bar graph showing induction of apoptosis by reverse Nur77 peptides.

Induction of apoptosis by reverse Nur77 peptides. To further explore the sequence requirements for apoptosis, we reversed the Nur77-9 sequence and also made the corresponding D-enantiomer of the Nur77-9 reverse sequence. Both the reverse (inverso) sequence and the corresponding D-enantiomer (retroinverso) sequence were apoptotic (FIG. 14).

Figure 16:
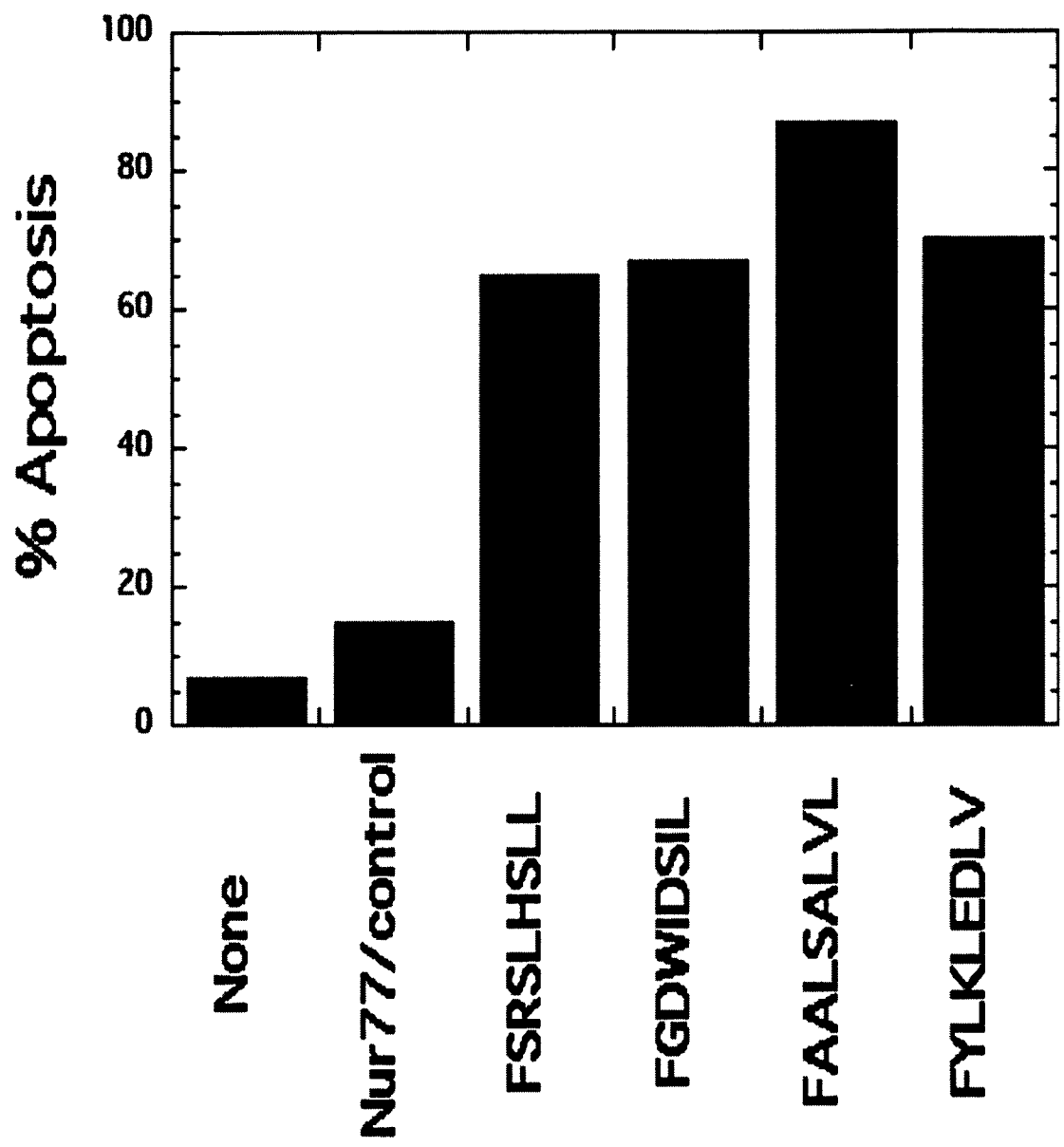
FIG. 16 is a bar graph showing induction of apoptosis by Nur77-DC3 derived peptides (FGDWIDSIL, SEQ ID NO: 16, FSRSLHSLL, SEQ ID NO: 9, FAALSALVL, SEQ ID NO: 17, and FYLKLEDLV, SEQ ID NO: 18).

Induction of apoptosis by Nur77-DC3 derived peptides. A Nur77 fragment, DC-3 (FIG. 15, SEQ ID NO: 60), which corresponds to a portion of the Nur77 ligand-binding domain (LBD), binds Bcl-2, resulting in its conformational change and apoptosis. The fragment displays four sequences including one found in Nur77-9 (SEQ ID NO: 9) that share a common motif, F Xaa$_n$ L Xaa$_n$ L Xaa$_n$ L, wherein n is between 0 and 3, Xaa is any amino acid, and Leu can be replaced by a hydrophobic amino acid. Each of the additional Nur77 DC3 sequences: FGDWIDSIL (SEQ ID NO: 16), FAALSALVL (SEQ ID NO: 17), FYLKLEDLV (SEQ ID NO: 18) when extended with GXrrrrrrrr are apoptotic (FIG. 16).

Figure 17:
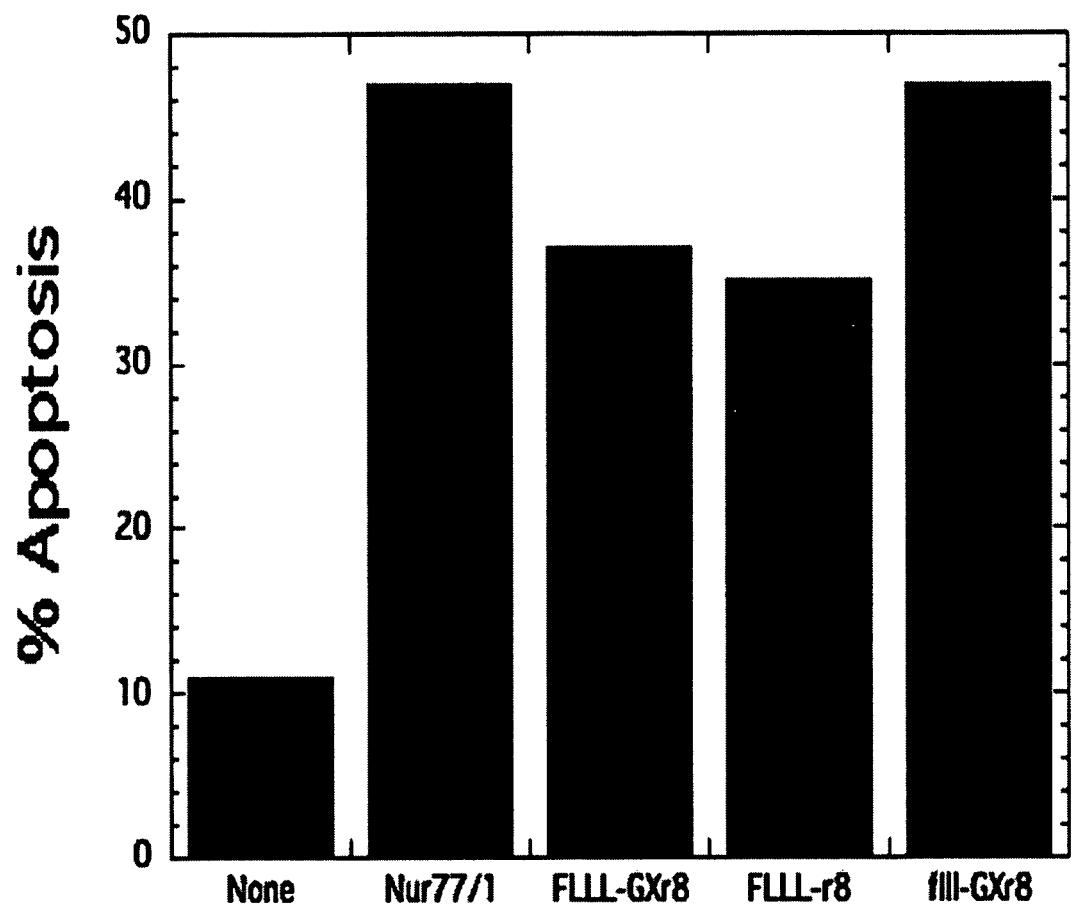
FIG. 17 is a bar graph showing induction of apoptosis by short Nur77 peptides.

Induction of apoptosis by short Nur77 peptides. In addition, any alanine substitutable interior amino acid (Xaa) can be removed, i.e. SRS and HS can be deleted one by one or in any combination thereof. For example, each of the alanine-substitutable amino acids can be removed to give FLLL (SEQ ID NO: 40) which is apoptotic. These studies identify a short Nur77 9-mer peptide that mimics the converter activity of the Nur77 protein (FIG. 17). This demonstrates that small molecule drugs would be useful for converting Bcl-2 from a protector to a killer of breast cancer cells which could reverse the drug and gamma-irradiation resistance of breast cancers.

Figure 18:
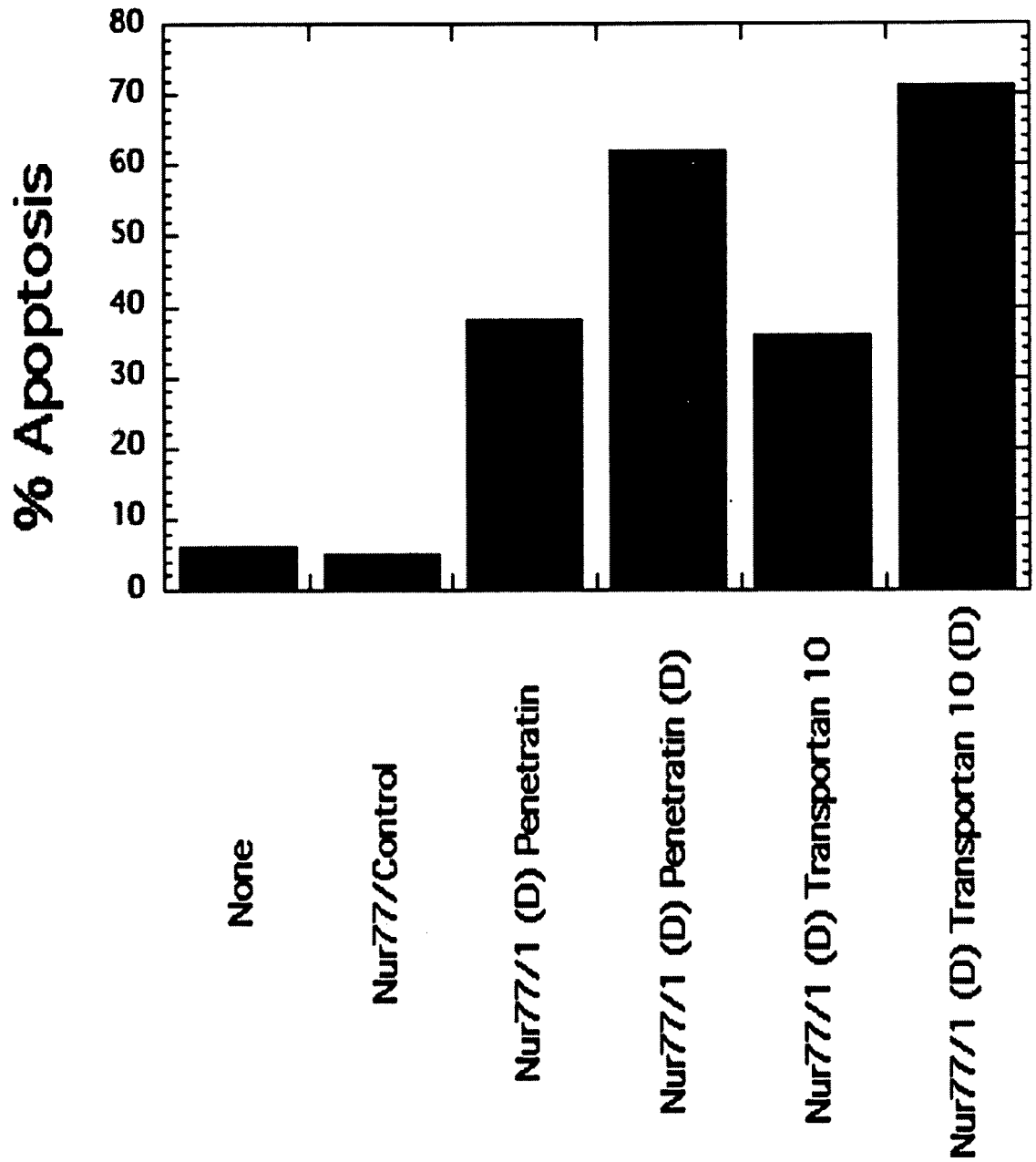
FIG. 18 is a bar graph showing that Nur77 peptides linked to various cell penetrating peptides are apoptotic.

Nur77 peptide linked to various cell penetrating peptides are apoptotic. The pro-apoptotic modulator of Bcl-2 can be linked to various cell penetrating peptide sequences including the penetratin sequence (RQIKIWFQNRRMKWKK, SEQ ID NO: 65, and the transportan 10 sequence (AGYLLGKINLKALAALAKKIL, SEQ ID NO: 66). Both the Nur77 sequence and the cell penetrating sequences can exist in the L form, D form or mixed D/L or DDLL forms to induce apoptosis (FIG. 18). Thus the Nur77 D-peptide can be linked to a D-transportan peptide and is apoptotic.

All of the D-peptides were protease resistant, an important property for in vivo use. FAM-labeled Nur77/1 (D) Transportan 10 (D) is proteolytically stable for up to one day in mouse serum and upon intravenous injection in a mouse is proteolytically stable during the course of its excretion.

Figure 19:
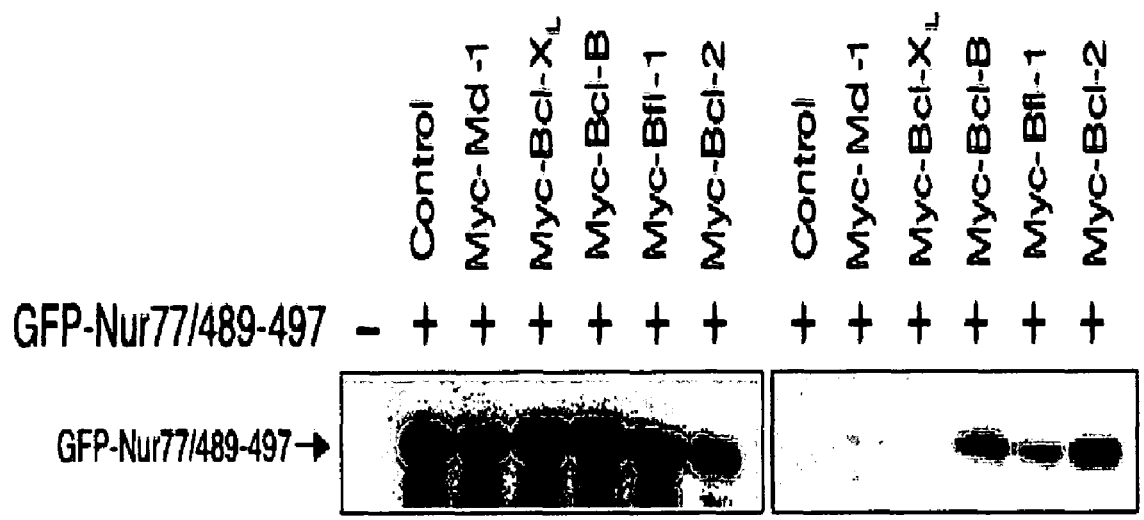
FIG. 19 is a photograph of an immunoblot gel showing that Nur77 peptide binds anti-apoptotic Bcl-2 family members.

Nur77 peptide binds anti-apoptotic Bcl-2 family members. Nur77-peptide binds Bcl-B, Bfl-1, and Bcl-2, but not Mcl-1 and Bcl-xL. DNA sequences corresponding with NuBCP-9 (Nur77/489-497) were cloned as a GFP fusion. The expression vector for the GFP-Nur77/489-497 fusion was transfected into HEK293T cells together with or without the indicated expression vector for myc-tagged Bcl-2 family member. Cell lysates were prepared and analyzed for interaction of Nur77/489-497 with Bcl-2 family members by co-immunoprecipitation assay using anti-Myc antibody. Immunoprecipitates were then separated on SDS/PAGE and immunoblotted using anti-GFP antibody. The results showed that GFP-Nur77/489-497 interacts with Bcl-B, Bfl-1, and Bcl-2, but not with Bcl-$X_L$ and Mcl-1 (FIG. 19).

Materials and Methods

Plasmids—Plasmids encoding Nur77 and Nur77/ΔDBD (Li, et al. 2000 Science 289:1159-1164), Bcl-2, Bcl-Gs, L216E-Bcl-Gs, Bcl-2/Aloop (Cheng et al. 1997 Science 278: 1966-1968), Bax, and Bcl-$X_L$ (Guo, et al. 2001 J Biol Chem 276:2780-2785), have been described previously. To construct plasmids encoding N168, DC3, DC1, Nur77/ΔDBD/DC1, Nur77/ΔDBD/A471-488, and Bcl-2/1-80, appropriate Nur77 or Bcl-2 fragments were prepared either by restriction enzyme digestion or amplified by polymerase chain reaction (PCR) by well known methods. The resulting Nur77 fragments were then cloned into pGFP-N2 vector (Clontech, USA).

Nur77/ΔDBD/L487A mutants were cloned by substituting Leu487 with Ala by PCR site-directed mutagenesis on the Nur77/ΔDBD template. Bcl-2/Y108K, Bcl-2/L137A, Bcl-2/G145A, and Bcl-2/R146 were constructed by substituting Tyr108, Leu137, Gly145 and Arg146 with Lys, Ala, Ala, and Glu, respectively, by PCR site-directed mutagenesis using the Bcl-2 cDNA as a template. Bcl2/ΔBH1, Bcl-2/ΔBH2, Bcl-2/ΔBH3, Bcl-2/ΔBH4, Bcl-2/ΔTM are deletions of 132-160, 189-204, 90-114, 7-30, 205-239 amino acids in Bcl-2 (Hanada et al. 1995 J Biol Chem 270:11962-11969). All mutations were confirmed by DNA sequencing.

Bcl-2 siRNAs and antisense oligonucleotides—The target siRNA SMARTpools for Bcl-2 and Bak and the siRNA oligonucleotide for Nur77 (5'-CAG UCC AGC CAU GCU CCU dTdT) (SEQ ID NO: 67) were purchased from Dharmacon Research Inc. Target or control siRNA were transfected at a final concentration of 200 nM into cells at 40% confluency using Oligofectamine reagent (Invitrogen) according to the manufacturer's recommendations. After 48 h, cells were analyzed. Bcl-2 antisense oligonucleotide targeting Bcl-2 and negative control oligonucleotides were obtained from Calbiochem. They (2.5 µM) were transfected into cells at 60% confluency for 36 h before analysis.

Peptide synthesis. Peptides were synthesized on MBHA resin using Fmoc synthesis and DIC/HOBt coupling with an Advanced Chem Tech 350 and 396 multiple peptide synthesizer. All peptides except FITC-peptides were acetylated on their N-termini and all were amidated on their C-termini. Standard deprotection conditions were used for all peptides except those with Pbf-protected D-arginine octamers which were treated for 6 hr. Peptides were purified by HPLC on C18 columns and confirmed by MALDI mass analysis. Disulfide linked peptides were prepared as described (Giriat, I. & Muir, T. W. 2003 J Am Chem Soc 125:7180-1). Peptides with C-terminal cysteines were covalently linked to chloroacetylated N-aminocaproic acid in a displacement reaction.

Nur77/Bcl-2 interaction assays—Reporter gene assays using NurRE-tk-CAT in CV-1 cells, and GST pull-down assay were described previously (Li, et al. 2000 Science 289: 1159-1164). For the mammalian two-hybrid assays, CV-1 cells were co-transfected with pcDNA-Gal4TAD-Nur77 or pcDNA-Gal4TAD-Nur77/ΔDBD and pcDNA-Gal4 DBD-Bcl-2/ΔTM along with a luciferase reporter gene driven by four copies of the Gal-4-binding site. The cells were harvested and reporter gene activity was measured. For Co-IP assays, HEK293T cells were transiently transfected with various expression plasmids using a modified calcium phosphate precipitation method (Wu et al, 1997) in the presence of caspase inhibitors (zVAD-fmk) to prevent degradation of Nur77 protein due to apoptosis. Cells were suspended in lysis buffer (50 mM Tris-HCl, PH7.4; 150 mM NaCl; 20 mM EDTA; 1% NP-40; 1 mM PMSF; 50 µg/ml Leupeptin; 20 mg/ml Aprotinin; 0.1 mM $Na_3VO_4$; and 1 mM DTT). Cells extracts were cleared by incubation with the Protein A/G plus Agarose beads (Santa Cruz) and then incubated with appropriate antibody and 30 µl of Protein A or G plus Agarose beads overnight at 4° C. Beads were then washed and boiled in Laemmli gel-loading solution before performing SDS-PAGE/immunoblotting using the following polyclonal or monoclonal antibodies: monoclonal mouse anti-GFP (Medical and Biological Laboratories), monoclonal mouse anti-HA (Roche Molecular Biochemicals), monoclonal mouse anti-FLAG (Sigma), monoclonal mouse anti-Myc (Santa Cruz), polyclonal rabbit anti-Nur77 (Active Motif), or monoclonal mouse anti-Bcl-2 (Santa Cruz). Immunoreactive products were detected by chemiluminescence with an enhanced chemiluminescence system (ECL) (Amersham).

Subcellular localization assays—Cells were seeded onto cover-slips in 6-well plates overnight, then transiently transfected with GFP-fusion expression plasmids. After 16 hours, cells were washed with PBS and fixed in 4% paraformaldehyde. For mitochondrial staining, cells were then incubated with anti-Hsp60 goat IgG (Santa Cruz, USA), followed by anti-goat IgG conjugated with Cy3 (Sigma). For cyt c staining, cells were incubated with monoclonal anti-cyt c IgG (PharMingen), followed by anti-mouse IgG conjugated with Cy5 (Amersham). Fluorescent images were collected and analyzed using a MRC-1024 MP laser-scanning confocal microscope (Bio-Rad). Subcellular fractionation assays were performed as described (Li, et al. 2000 Science 289:1159-1164). Briefly, cells ($1 \times 10^7$ cells) suspended in 0.5 ml hypotonic buffer (5 mM Tris-HCl, pH 7.4, 5 mM KCl, 1.5 mM $MgCl_2$, 0.1 mM EGTA, pH 8.0, and 1 mM DTT) were homogenized and cell extracts were centrifuged at 500×g for 5 min. The resulting supernatant was centrifuged at 10,000×g for 30 min at 4° C. to obtain the HM fraction. HM fraction was resuspended in 100 µl lysis buffer (10 mM Tris, pH 7.4, 150 mM NaCl, 1% Triton X-100, 5 mM EDTA, pH 8.0) for immunoblotting analysis.

Apoptosis assays—For nuclear morphological change analysis, cells were trypsinized, washed with PBS, fixed with 3.7% paraformaldehyde, and stained with DAPI (4,6-diamidino-2-phenylindole) (50 µg/ml) to visualize the nuclei by UV-microscopy. The percentages of apoptotic cells were determined by counting 300 GFP-positive cells, scoring cells having nuclear fragmentation and/or chromatin condensation.

Fluorescence polarization (FP) assays. GST-Bcl-2, GST-Bcl-$X_L$, or GST protein was briefly incubated with FITC-conjugated peptide with or without competitors in Greiner Fluotrac 600 96-well microplates. Fluorescence polarization was recorded using an Analyst HT 96-384 microplate reader (Molecular Devices, Sunnyvale, Calif.) with excitation wavelength set at 485 nm and dynamic polarizer for emission at 530 nm.

Circular dichroism (CD) spectroscopy. Stock solutions of 3 mM peptide in 30% acetonitrile/water were added to 0.5 mL of 2 µM purified GST-proteins in PBS, pH 7.6. CD spectra were obtained in a 0.2 cm pathlength cell at 20° C. using an AVIV 62 DS spectropolarimeter for a wavelength range from 200 to 260 nm with a step size of 1 nm averaged for 5 sec. Three spectra were corrected for background and averaged for each sample. The Kd was determined using nonlinear regression analysis for a one-site-binding model ($\chi2>0.98$). Stoichiometry was determined from a Zhou plot (Jones, G. et al. 2002 *Tet. Let.* 43 :6079-6082).

Cell culture. H460 lung cancer cells were maintained in RPMI 1640 medium supplemented with 10% fetal bovine serum (FBS). HEK293T embryonic kidney cells were grown in DME medium supplemented with 10% FBS. Jurkat and Jurkat cells stably expressing Bcl-2 were kindly provided by Dr. John Reed, and they were maintained in RPMI1640 medium.

Confocal microscopy. Cells were seeded on chamber slides overnight and treated with apoptotic agents in medium containing 0.5% FBS. After treatments cells were fixed in PBS containing 3.7% paraformaldehyde for 10 min and washed twice with PBS. Cells were then permeabilized with 0.1% triton X-100 in PBS for 5 min. Fixed cells were pre-incubated for 30 min in PBS containing 5% BSA at room temperature.

Transient transfection assays. Cells ($1 \times 10^5$ cells/well) seeded in 24-well plates were transiently transfected using a modified calcium phosphate precipitation procedure.

Immunoblotting. Cell lysates were boiled in SDS sample buffer, resolved by SDS-polyacrylamide gel electrophoresis, and transferred to nitrocellulose. After transfer, the membranes were blocked in 5% milk in TBST (10 mM Tris-HCl, pH.8.0, 150 mM NaCl, 0.05% Tween 20) containing antibody. The membranes were washed three times with TBST, then incubated for 1 hr at room temperature in 5% milk in TBST containing horseradish peroxidase-linked anti-immunoglobulin. After 3 washes in TBST, immunoreactive products were detected by chemiluminescence with an enhanced chemiluminescence system (ECL, Amersham).

Animal studies. Female SCID mice (6-week-old) (Tacomic) were injected with $10^6$ MDA-MB435 breast carcinoma cells. Tumors were palpable on day 7. On days 10 and 13, test peptides (620 µg in 50 µL PBS) were injected into the tumor areas of 5 mice. Tumor volumes ($1 \times w^2$) were determined using calipers. No weight changes were observed. Established tumors in control mice were injected with test peptides and tumor tissues were excised and sectioned after 3 days. Tissues were fixed (10% buffered formalin), then rapidly paraffin-embedded. Apoptosis was detected by the TUNEL assay.

Example 2

The FITC-NuBCP-9-r8 peptide is used in competitive FPA assays to identify peptidomimetics and small molecule mimics or antagonists of Nur77 or functionally related proteins such as Nor1 or Not (also Nurr1) that compete with NuBCP-9-r8 for binding to Bcl-2 or Bcl-2 related proteins. Mimics are distinguished from antagonists using CD analysis described above which detects the presence or absence of a conformational change. Nur77 mimics induce a conformational change in Bcl-2 similar to that observed for NuBCP-9 while antagonists compete with NuBCP-9-r8 for binding to Bcl-2 but not induce a conformational change. Mimics are used to identify compounds that act as pro-apoptic compounds whereas antagonists block the pro-apoptotic effects of Nur77 or functionally equivalent proteins such as Nor1 and Not. Compounds that antagonize Nur77 or functionally related proteins are used to treat neurodegenerative diseases that are characterized by converting Bcl-2 to its pro-apoptotic form.

Example 3

A patient diagnosed with breast cancer is selected for treatment with the D-NuBCP-9-r8 peptide. The patient is given a therapeutically effective intravenous dose of the peptide at regular intervals over a six week period. Following the end of the treatment period it is observed that the breast cancer has regressed.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A compound comprising:
   a peptide consisting of the sequence of SEQ ID NO:60 or mutation or fragment thereof, wherein the peptide is pro-apoptotic; and
   a cell-penetrating-peptide, wherein said compound induces apoptosis of mammalian cells expressing Bcl-2 or Bcl-2 related proteins.

2. The compound of claim 1, wherein said cell-penetrating peptide comprises transportan 10.

3. The compound of claim 1, wherein said cell-penetrating peptide consists of penetratin (SEQ ID NO: 65).

4. The compound of claim 1, wherein the pro-apoptotic fragment consists of the amino acid sequence Phe Gly Asp Trp Ile Asp Ser Ile Leu (SEQ ID NO:16).

5. The compound of claim 1, wherein the pro-apoptotic fragment consists of the amino acid sequence Phe Ser Arg Ser Leu His Ser Leu Leu (SEQ ID NO:9).

6. The compound of claim 1, wherein the pro-apoptotic fragment consists of the amino acid sequence Phe Ala Cys Leu Ser Ala Leu Val Leu (amino acid residues 37-45 of SEQ ID NO:60).

7. The compound of claim 1, wherein the pro-apoptotic fragment consists of the amino acid sequence Phe Tyr Leu Lys Leu Glu Asp Leu Val (SEQ ID NO:18).

8. The compound of claim 1, wherein the mutation is an amino acid deletion.

9. The compound of claim 1, wherein the mutation is an amino acid insertion.

10. The compound of claim 1, wherein the mutation is a conservative amino acid substitution.

11. The compound of claim 1, wherein the mutation is an amino acid substitution with Alanine.

12. The compound of claim 1, wherein the mutation is an amino acid substitution with a non-naturally occurring amino acid.

13. The compound of claim 1, wherein the compound comprises one or more D-amino acids.

* * * * *